United States Patent
Warrell, Jr. et al.

(10) Patent No.: US 10,093,658 B2
(45) Date of Patent: Oct. 9, 2018

(54) BIFUNCTIONAL COMPOUNDS AND USE FOR REDUCING URIC ACID LEVELS

(71) Applicant: Acquist LLC, Westfield, NJ (US)

(72) Inventors: Raymond P. Warrell, Jr., Westfield, NJ (US); John J. Piwinski, Lebanon, NJ (US)

(73) Assignee: Acquist LLC, Westfield, NJ (US)

( * ) Notice: Subject to any disclaimer, the term of this patent is extended or adjusted under 35 U.S.C. 154(b) by 0 days.

(21) Appl. No.: 15/545,429

(22) PCT Filed: Jan. 20, 2016

(86) PCT No.: PCT/US2016/014107
§ 371 (c)(1),
(2) Date: Jul. 21, 2017

(87) PCT Pub. No.: WO2016/118611
PCT Pub. Date: Jul. 28, 2016

(65) Prior Publication Data
US 2018/0002315 A1   Jan. 4, 2018

Related U.S. Application Data

(60) Provisional application No. 62/106,313, filed on Jan. 22, 2015.

(51) Int. Cl.
*C07D 403/12* (2006.01)
*C07D 239/62* (2006.01)
*C07D 413/12* (2006.01)

(52) U.S. Cl.
CPC ......... *C07D 403/12* (2013.01); *C07D 239/62* (2013.01); *C07D 413/12* (2013.01)

(58) Field of Classification Search
CPC ........................... C07D 403/12; C07D 239/62
See application file for complete search history.

(56) References Cited

U.S. PATENT DOCUMENTS

| | | | |
|---|---|---|---|
| 4,034,093 A | 7/1977 | Klemm |
| 4,239,762 A | 12/1980 | Kramer |
| 4,602,912 A | 7/1986 | De Sousa |
| 4,634,707 A | 1/1987 | Brewer |
| 4,636,508 A | 1/1987 | Brewer |
| 4,762,830 A | 8/1988 | Sturm |
| 4,879,276 A | 11/1989 | Brewer |
| 4,880,811 A | 11/1989 | Warrell, Jr. |
| 6,335,332 B1 | 1/2002 | Ambrogio |
| 7,119,201 B2 | 10/2006 | Reiter |
| 9,428,466 B2 | 8/2016 | Warrell |
| 2009/0264401 A1 | 10/2009 | Gill |

FOREIGN PATENT DOCUMENTS

| | | |
|---|---|---|
| WO | 88/10114 A1 | 12/1988 |
| WO | 91/13623 A1 | 9/1991 |
| WO | 2015/073317 A1 | 5/2015 |
| WO | 2015/123003 A1 | 8/2015 |
| WO | 2016/118611 A1 | 7/2016 |

OTHER PUBLICATIONS

CAS Abstract U.S. Pat. No. 4,634,707 (1987), 2 pages.
CAS Registry No. 1349276-03-4 (2011), 1 page.
International Search Report and Written Opinion in PCT/US2017/038522, dated Oct. 3, 2017, 20 pages.
Non-Final Office Action dated Oct. 5, 2017, in U.S. Appl. No. 15/118,243, 21 pages.
International Preliminary Report on Patentability in PCT/US2016/014107, dated Aug. 3, 2017, 7 pages.
International Search Report and Written Opinion in PCT/US15/12370, dated Apr. 17, 2015, 10 pages.
International Search Report and Written Opinion in PCT/US2016/014107, dated May 17, 2016, 11 pages.
PCT Preliminary Report on Patentability in PCT/US2015/012370 dated Aug. 25, 2016, 7 pages.
Lebedyeva, et al., "Reaction of barbituric acid with organic azides and phosphonium ylides", Central European Journal of Chemistry, vol. 11, No. 6, 2013, pp. 1019-1022.
International Search Report and Written Opinion in Intl. Appl. No. PCT/US2017/038525, dated Aug. 22, 2017, 16 pgs.
International Search Report and Written Opinion in PCT/US2017/040836, dated Sep. 12, 2017, 15 pages.
Partial Search Report in PCT Application No. PCT/US2017/038522, dated Aug. 15, 2017, 2 pgs.

*Primary Examiner* — Golam M Shameem
(74) *Attorney, Agent, or Firm* — Servilla Whitney LLC

(57) ABSTRACT

Bifunctional compounds that increase uric acid excretion and reduce uric acid production, and monofunctional compounds that either increase uric acid excretion or reduce uric acid production. Methods of using these compounds for reducing uric acid levels in blood or serum, for treating disorders or uric acid metabolism, and for maintaining normal uric acid levels in blood or serum are provided. Pharmaceutical compositions comprising the bifunctional and monofunctional compounds are also provided.

17 Claims, 20 Drawing Sheets

BIFUNCTIONAL COMPOUNDS AND USE FOR REDUCING URIC ACID LEVELS

CROSS REFERENCE TO RELATED APPLICATIONS

This is a National Phase entry of International Application No. PCT/US2016/014107, filed Jan. 20, 2016, which claims priority to U.S. Provisional Application 62/106,313, filed Jan. 22, 2015, the disclosures of which are incorporated herein by reference in their entireties.

TECHNICAL FIELD

This invention relates to pharmaceutical compositions and methods for reducing uric acid in blood or serum of a subject employing bifunctional and monofunctional compounds as active agents.

BACKGROUND

Gout afflicts more than 8 million U.S. subjects, and is associated with chronic elevation of uric acid (UA) in blood. The incidence of this condition has doubled in the past ten years. When UA exceeds solubility limits, it forms crystals that settle into joints and kidney, causing severe pain, destructive arthritis, and kidney failure. Treatment for chronic gout entails extended—if not lifelong—therapy focused on reducing UA production or increasing its excretion. The standard-of-care for initial therapy of gout is allopurinol, a drug that inhibits xanthine oxidase (XO), a key production enzyme. Launched in 2009, Uloric® (febuxostat; Takeda), has similar activity as an XO inhibitor with somewhat higher efficacy and improved safety. Xanthine oxidase inhibitors are used as initial therapy in more than 90% of gout patients; nonetheless, the therapeutic target is achieved in less than one-third of patients, the drugs have multiple side effects, and hypersensitivity (especially to allopurinol) is common. Given that most patients do not actually respond, the continued use of ineffective treatment administered over many months in order to determine the low percentage of patients who might respond represents an important burden to patients as well as substantial costs to global healthcare systems, Moreover, the high proportion of failures causes many patients to become non-compliant with therapy and thus at increased risk for development of chronic complications of gout, especially destructive arthritis and renal insufficiency.

Since 2000, rapid advances in the biology of proteins known as transporters have presented an array of new drug targets. The enzyme URAT1 is a high capacity renal transporter that reabsorbs most of the UA that is initially filtered into the urine from the blood by the kidney. Inhibitors of certain urate transporters may prevent such reabsorption and thereby increase UA excretion. Several drugs are now known to inhibit URAT1, including benzbromarone (approved but withdrawn in the US by Sanofi in 2003), probenecid, and lesinurad (AstraZeneca), an investigational drug currently in late-stage development.

These drugs are all mono-functional. That is, they inhibit only one of the two equilibrium paths that reduce the levels of UA in blood (i.e., decreased production or increased excretion). Allopurinol is an example of a drug that decreases UA production by inhibiting xanthine oxidase, but it has no effect on renal excretion. As expected, allopurinol does not affect the activity of URAT1 or other renal urate transporters. Benzbromarone, lesinurad and probenecid increase UA excretion (i.e., they promote uricosuria) primarily via inhibition of URAT1, but these agents have no effect on UA production, since they have no substantial effect on xanthine oxidase. Since xanthine oxidase inhibition is the principal, preferred, and primary form of treatment for hyperuricemia, agents that promote uricosuria are typically used second-line and are commonly employed only in combination with xanthine oxidase inhibitors rather than as single-agents.

Non-sedating 5-carboxanilide derivatives of barbiturates, including merbarone (5-(N-phenylcarboxamido)-2-thio-barbituric acid), have been evaluated as potential cytotoxic anticancer drugs. Subsequently, it was discovered that clinical treatment with merbarone was associated with a marked reduction of UA levels in blood. Despite these discoveries, the cytotoxic activity of merbarone would completely preclude its use as a treatment for chronic lifelong disorders of UA metabolism, since the safety of such use (primarily its genotoxic potential) would pose a serious risk to other aspects of human health. Such clinical utility would only be possible if the genotoxic activity could be chemically dissociated from the various hypouricemic activities. The inventors have since described a number of non-genotoxic hypouricemic derivatives of merbarone.

There exists a compelling need for new drugs than can reduce UA levels in blood and provide better treatment for patients afflicted by gout. Reduction in UA is universally acknowledged as beneficial for patients with gout and other hyperuricemic disorders, and reduced serum UA is accepted by international drug regulatory agencies (e.g., the U.S. Food and Drug Administration [FDA], the European Medicines Agency [EMA], etc.) as an endpoint for commercial drug approval in these diseases. As previously noted, drugs that can overcome the limited clinical activity of xanthine oxidase inhibitors are available or are currently being investigated, but only as "add-ons" for combination use. The present invention relates to new compounds that can provide alternatives to current therapy for elevated UA levels and treatment of disorders of UA metabolism such as gout. Certain of these compounds have the particular advantage of bifunctional activity (i.e., decreasing UA production by inhibiting xanthine oxidase and increasing UA excretion by inhibiting a renal urate transporter), making them suitable for use as initial therapy and as single agents rather than "add-on" therapies. In addition, certain of the compounds have reduced toxicity compared to prior art drugs such as merbarone.

SUMMARY

In a first aspect, the invention relates to a compound having a structure represented by Formula (I):

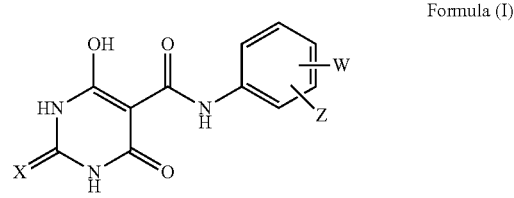

Formula (I)

wherein
X is O or S;
W is present or absent, and if present is one or more hydroxyl moieties, $R^1OH$, or at least one hydroxyl moiety and $R^1OH$;
Z is present or absent, and if present is $-SO_2N(R^2)_2$, $-R^1CO_2H$,

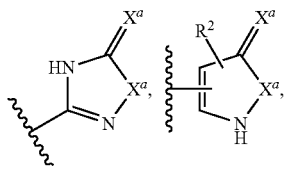

$-NR^2SO_2R^3$, $-NR^2SO_2N(R^2)_2$ or $-NR^2C(O)N(R^2)_2$;
wherein $R^1$ is alkyl;
wherein each $R^2$ is independently H, alkyl or aryl, each optionally substituted with one or more halogen atoms or $OR^2$;
wherein each $R^3$ is independently alkyl or aryl, each optionally substituted with one or more halogen atoms or $OR^2$; and
wherein each $X^a$ is independently selected from either O or S, provided that at least one of W and Z is present, and if W is present and Z is absent, W is not 4'-hydroxy.

In one or more specific embodiments, the compound having a structure represented by Formula (I) is a compound selected from the group consisting of:
  a compound wherein X is O or S, W is absent and Z is $-SO_2NH_2$;
  a compound wherein X is O or S, W is absent and Z is $-NHSO_2CH_3$;
  a compound wherein X is O or S, W is absent and Z is $-NHSO_2CF_3$;
  a compound wherein X is O or S, Z is absent and W is $-OH$ and $-CH_2OH$; and
  a compound wherein X is O or S, W is absent and Z is $-CH_2CO_2H$.
  a compound wherein X is O or S, W is absent and Z is

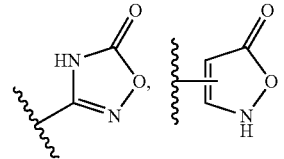

In a second aspect, the invention relates to a compound having a structure represented by Formula (II):

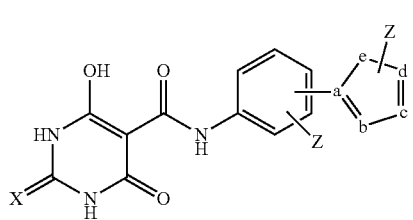

Formula (II)

wherein
X is O or S; and
Each Z is independently present or absent and, if present, is independently selected from one or more halogen atoms, $-CN$, $-CF_3$, $-OR^2$, $-C(O)R^2$, $SR^2$, $-S(O)_fR^3$ where f is 1 or 2, $-N(R^2)_2$, $-NO_2$, $-CO_2R^2$, $-OCO_2R^3$, $OC(O)R^2$, $-CON(R^2)_2$, $-NR^2C(O)R^2$, $-SO_2N(R^2)_2$, $-NR^2SO_2R^3$, $-NR^2SO_2N(R^2)_2$ or $-NR^2C(O)N(R^2)_2$, alkyl, aryl, alkenyl and alkynyl;
wherein each $R^2$ is independently H, alkyl or aryl;
wherein each $R^3$ is independently alkyl or aryl, optionally substituted with one or more halogen atoms or $OR^2$; and
wherein a, b, c, d, and e are each independently carbon or nitrogen, with the proviso that at least one of a, b, c, d and e is nitrogen and Z is not connected directly to a nitrogen except that Z may optionally be connected to a nitrogen at a, b, c, d, or e by replacement of the hydrogen of an NH group when Z is $-C(O)R^2$, $-S(O)_fR^3$, $-CO_2R^3$, $-CON(R^2)_2$, $-SO_2N(R^2)_2$, alkyl, aryl, alkenyl or alkynyl.

In one or more specific embodiments, the compound having a structure represented by Formula (II) is a compound selected from the group consisting of:
  a compound wherein X is O; W and Z are absent; b, c, and d are N; e is NH, and; a is C, and tautomers thereof;
  a compound wherein X is S; W and Z are absent; b, c, and d are N; e is NH, and a is C, and tautomers thereof; and
  a compound wherein X is O or S; W and Z are absent; a, c, d and e are N, and; b is CH.

In a third aspect, the invention relates to a compound having a structure represented by Formula (III):

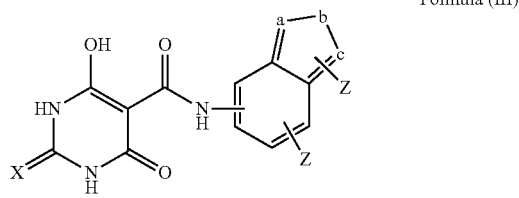

Formula (III)

wherein
X is O or S; and
Each Z is independently present or absent and, if present, is independently selected from one or more halogen atoms, $-CN$, $-CF_3$, $-OR^2$, $-C(O)R^2$, $SR^2$, $-S(O)_fR^3$ where f is 1 or 2, $-N(R^2)_2$, $-NO_2$, $-CO_2R^2$, $-OCO_2R^3$, $OC(O)R^2$, $-CON(R^2)_2$, $-NR^2C(O)R^2$, $-SO_2(NR^2)_2$, $-NR^2SO_2R^3$, $-NR^2SO_2N(R^2)_2$ or $-NR^2C(O)N(R^2)_2$, alkyl, aryl, alkenyl and alkynyl;
wherein each $R^2$ is independently H, alkyl or aryl;
wherein each $R^3$ is independently alkyl or aryl, optionally substituted with one or more halogen atoms or $OR^2$; and
wherein a, b, and c, are each independently carbon or nitrogen, with the proviso that at least one of a, b, and c is nitrogen and Z is not connected directly to a nitrogen except that Z may optionally be connected to a nitrogen at a, b, or c by replacement of the hydrogen of an NH group when Z is $-C(O)R^2$, $-S(O)_fR^3$, $-CO_2R^3$, $-CON(R^2)_2$, $-SO_2N(R^2)_2$, alkyl, aryl, alkenyl or alkynyl.

In one or more specific embodiments, the compound having a structure represented by Formula (III) is a compound wherein X is O; both Z are absent; a and c are N, and; b is NH and tautomers thereof.

In certain embodiments of any of the compounds having a structure represented by Formula (I), Formula (II) or Formula (III), alkyl moieties may each independently be C1-C6, aryl moieties may each independently be C6-C10, alkenyl moieties may each independently be C2-C6, and alkynyl moieties may each independently be C2-C6.

A further aspect of the invention relates to methods for reducing uric acid levels in blood or serum of a subject comprising administering a compound having a structure represented by Formula (I), Formula (II), Formula (III), or a combination thereof, to a subject in need thereof in an amount effective to reduce blood or serum uric acid levels. In a modification of this embodiment, the methods comprise administering a compound according to a specific embodiment of the compounds of Formula (I), Formula (II), Formula (III), or a combination thereof, as described above, to a subject in need thereof in an amount effective to reduce blood or serum uric acid levels.

A modification of this aspect of the invention relates to methods for preventing elevation of uric acid levels in blood or serum of a subject comprising administering a compound having a structure represented by Formula (I), Formula (II), or Formula (III), or a combination thereof, to a subject in need thereof in an amount effective to prevent elevation of blood or serum uric acid levels. In a specific embodiment of this aspect, the methods for preventing elevation of uric acid levels in blood or serum of a subject comprise administering to a subject in need thereof one a compound according to a specific embodiment of the compounds of Formula (I), Formula (II), Formula (III), or a combination thereof, as described above, to a subject in need thereof in an amount effective to reduce blood or serum uric acid levels.

In certain embodiments of these methods, a compound having a structure represented by Formula (I), Formula (II), Formula (III), or a combination thereof, is administered to a subject with gout, hyperuricemia, kidney disease, arthritis, kidney stones, kidney failure, urolithiasis, plumbism, hyperparathyroidism, psoriasis, inborn genetic errors of metabolism, sarcoidosis or cardiovascular disease to reduce uric acid levels. In specific embodiments, the drug(s) are administered to a subject with gout or hyperuricemia to reduce uric acid levels. In other embodiments, a compound according to a specific embodiment of the compounds of Formula (I), Formula (II), Formula (III), or a combination, as described above, is/are administered to a subject with gout, hyperuricemia, kidney disease, arthritis, kidney stones, kidney failure, urolithiasis, plumbism, hyperparathyroidism, psoriasis, inborn genetic errors of metabolism, sarcoidosis or cardiovascular disease to reduce uric acid levels.

In certain embodiments of any of the foregoing methods, a compound having a structure represented by Formula (I), Formula (II), Formula (III), or a combination thereof, is administered by injection, infusion, intranasal, intrarectal, or oral administration. In other embodiments, a compound having a structure represented by Formula (I), Formula (II), Formula (III), or a combination thereof, is administered by injection, infusion, or oral administration.

In certain embodiments of any of the foregoing methods, a compound having a structure represented by Formula (I), Formula (II), Formula (III), or a combination thereof, is administered in a formulation that enables controlled release. Controlled release formulations release the active ingredient more slowly or extend the duration of its action within the body. In specific embodiments, the controlled release formulation is an oral controlled release formulation. In other embodiments of any of the foregoing methods, a compound according to a specific embodiment of the compounds of Formula (I), Formula (II), Formula (III), or a combination, as described above, is/are administered in a formulation that enables controlled release.

In certain embodiments of any of the foregoing methods, blood or serum uric acid levels are reduced by at least about 25% compared to blood or serum uric acid levels prior to administration of a compound having a structure represented by Formula (I), Formula (II), Formula (III), or a combination thereof. In specific embodiments, blood or serum uric acid levels of the subject are reduced by at least about 50% compared to levels prior to administration. In a specific embodiment, uric acid levels are reduced by about 75% even at daily doses of 1,500 mg/m$^2$/day or less.

In certain embodiments of any of the foregoing methods, a compound having a structure represented by Formula (I), Formula (II), Formula (III), or a combination thereof, is administered to the subject up to four times per day, once daily, once, twice or three times per week or once monthly. In other embodiments of any of the foregoing methods, a compound according to a specific embodiment of the compounds of Formula (I), Formula (II), Formula (III), or a combination, as described above, is/are administered to the subject up to four times per day, once daily, once, twice or three times per week or once monthly.

A fourth aspect of the invention relates to methods for treating a disorder of uric acid metabolism associated with or caused by elevated uric acid in blood or serum comprising administering to a subject in need thereof a compound having a structure represented by Formula (I), Formula (II), Formula (III), or a combination thereof, in an amount effective to reduce blood or serum uric acid levels or prevent elevation of blood or serum uric acid levels, thereby treating the disorder of uric acid metabolism. One such embodiment relates to methods for treating a disorder of uric acid metabolism associated with or caused by elevated uric acid in blood or serum comprising administering to the subject a compound according to a specific embodiment of the compounds of Formula (I), Formula (II), Formula (III), or a combination, as described above, up to four times per day, once daily, once, twice or three times per week or once monthly.

A further aspect of the invention provides pharmaceutical compositions comprising a compound having a structure represented by Formula (I), Formula (II), Formula (III), or a combination thereof, and a pharmaceutically acceptable carrier. In a specific embodiment, the pharmaceutical composition comprises a compound according to a specific embodiment of the compounds of Formula (I), Formula (II), Formula (III), or a combination thereof, as described above. In certain embodiments of the pharmaceutical composition, the pharmaceutically acceptable carrier is selected from the group consisting of one or more of a solvent, a dispersing agent, a coating, a surfactant, a preservative, an alcohol, a polyol, and an isotonic agent. In certain embodiments of any of the foregoing pharmaceutical compositions, the composition is formulated for administration by injection, infusion or oral routes. In certain embodiments of any of the foregoing pharmaceutical compositions, the composition is formulated as a solution, emulsion, capsule, or tablet. In certain embodiments of any of the foregoing pharmaceutical compositions, the composition is formulated for controlled release of the compound having a structure represented by Formula (I), Formula (II), Formula (III), or a combination thereof, for the purpose of releasing the active ingredient more slowly or extending the duration of its action within the body.

A further aspect of the invention relates to methods for synthesizing the compounds discussed above, as discussed in more detail below.

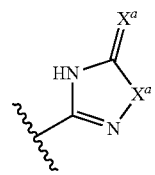

DETAILED DESCRIPTION

Figure 1:
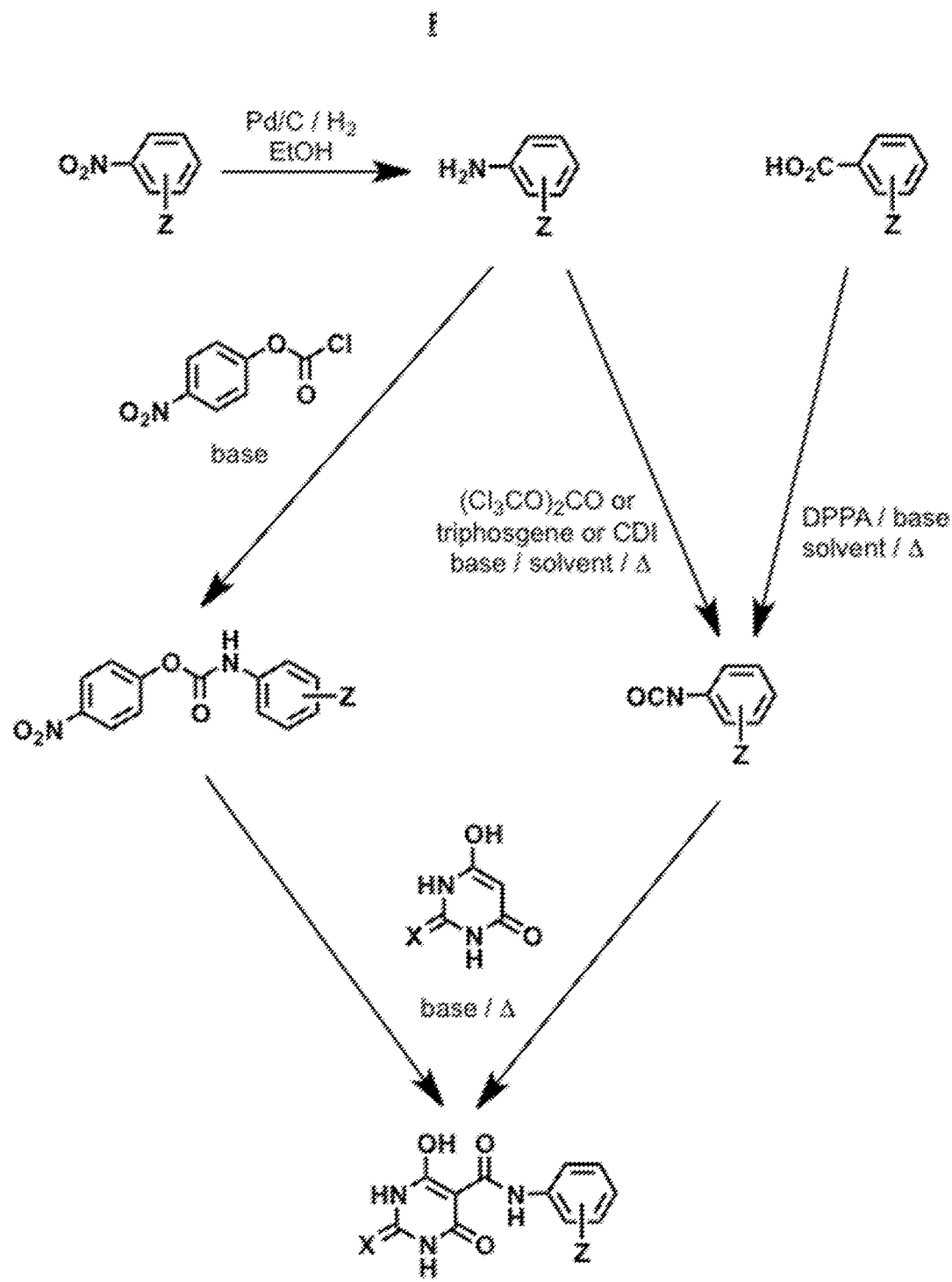
FIG. 1 illustrates a general synthesis scheme for preparation of compounds having a structure represented by Formula (I) when W is absent.

Before describing several exemplary embodiments of the invention, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used herein, the term "bifunctional" with respect to disclosed compounds means that the compound inhibits both a renal transporter, including but not limited to URAT1, and xanthine oxidase. The potency of inhibition of either target may vary, but in general an IC50 of less than about 100 µM for both xanthine oxidase and a renal transporter such as URAT1 is considered bifunctional. An IC50 of less than about 50 µM for both xanthine oxidase and URAT1 is considered a particularly active bifunctional compound, and an IC50 of less than 10 µM is considered a highly potent bifunctional compound.

As used herein, the term "monofunctional" with respect to disclosed compounds means that the compound inhibits an enzyme in the uric acid metabolic pathway involved in uric acid excretion that is either a renal transporter, including but not limited to URAT1, or an enzyme involved in uric acid production, including but not limited to xanthine oxidase, but not both. The potency of inhibition of single target may vary, but in general an IC50 of greater than about 100 µM for one of xanthine oxidase or URAT1, and an IC50 of less than about 100 µM for the other of xanthine oxidase or URAT1, is considered monofunctional. An IC50 of less than about 50 µM for one of xanthine oxidase or URAT1, and an IC50 of greater than about 100 µM for the other of xanthine oxidase or URAT1, is considered a particularly active monofunctional compound. An IC50 of less than about 10 µM for one of xanthine oxidase or URAT1, and an IC50 of greater than about 100 µM for the other of xanthine oxidase or URAT1, is considered a highly potent monofunctional compound.

As used herein, the term "treatment" refers to reducing elevated uric acid levels in blood or serum, preferably by reducing levels to the normal, low-normal or sub-normal range, with an overall goal of relieving symptoms and/or preventing recurrences of active disease. For example, a typical "therapeutic target" for treatment of elevated serum uric acid is a level ≤6.0 mg/dL. "Elevated" uric acid levels generally refers to high-normal and above-normal uric acid levels, as long-term elevated levels can result in conditions that require additional treatment.

As used herein, the term "preventing" elevation of uric acid levels in blood or serum refers to maintaining normal or therapeutically acceptable uric acid levels in blood or serum in a subject who would otherwise experience an increase in uric acid levels, with an overall goal of preventing development or recurrence of symptoms and/or preventing recurrences of active disease. It will be appreciated that prevention of elevation of uric acid levels is a goal of the maintenance therapy discussed below.

The numbering of the positions on the barbiturate ring used herein follows the convention of Warrell (U.S. Pat. No. 4,880,811). It is also to be understood that although the compounds disclosed herein are generally illustrated by specific chemical structures, the disclosure of the compounds is intended to include their tautomers. Representative examples of tautomers in the barbituate ring include the structures depicted below, as well as any additional tautomers on the substituents of Formulas I, II and III:

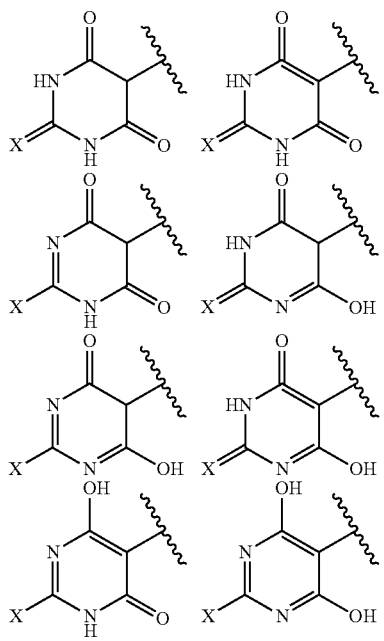

The compounds described herein meet certain needs in the therapeutic field of reduction of uric acid levels in blood and treatment of disorders of uric acid metabolism that are associated with, or caused by, elevated uric acid levels in blood or serum. Certain of the compounds are potent monofunctional inhibitors of URAT1 or xanthine oxidase. Certain of the compounds are bifunctional inhibitors of both URAT1 and xanthine oxidase.

The improved biological activity profile of the compounds of the invention and their potency make these compounds useful new drugs for reducing uric acid levels in blood, and for treating disorders of uric acid metabolism that are associated with, or caused by, elevated uric acid levels in blood or serum, including gout. Of particular significance is the advantage that the bifunctional compounds can be used effectively as monotherapy for reducing uric acid levels in blood, for treating disorders of uric acid metabolism, and specifically for treating gout.

In a first aspect, the invention relates to a compound having a structure represented by Formula (I):

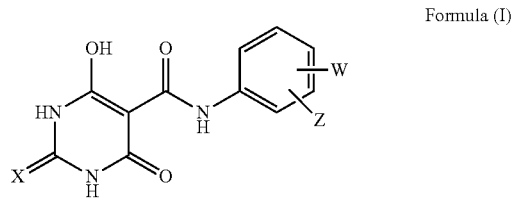

Formula (I)

wherein
X is O or S;
W is present or absent, and if present is one or more hydroxyl moieties, $R^1OH$, or at least one hydroxyl moiety and $R^1OH$; and
Z is present or absent, and if present is —$SO_2N(R^2)_2$, $R^1CO_2H$,

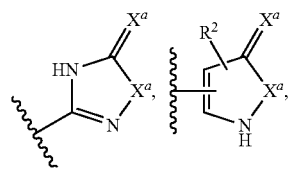

—$NR^2SO_2R^3$, —$NR^2SO_2NR^2$ or —$NR^2C(O)NR^2$,
wherein $R^1$ is alkyl;
wherein each $R^2$ is independently H, alkyl or aryl, each optionally substituted with one or more halogen atoms or $OR^2$;
wherein each $R^3$ is independently alkyl or aryl, each optionally substituted with one or more halogen atoms or $OR^2$; and
wherein each $X^a$ is independently selected from either O or S,
provided that at least one of W and Z is present, and if W is present and Z is absent, W is not 4'-hydroxy.

Specific embodiments of the compounds having structures represented by Formula (I) include the following compounds:
1. The compound wherein X is O, W is absent and Z is —$SO_2NH_2$, for example the compound having a structure represented by Formula (Ia):

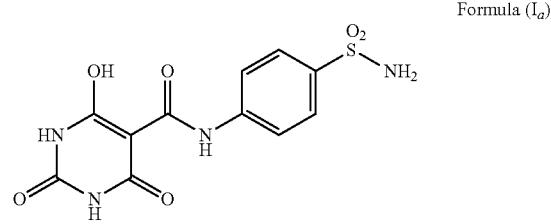 [SMILES: NS(=O)(=O)c1ccc(NC(=O)c2c(O)[nH]c(=O)[nH]c2=O)cc1]

Formula ($I_a$)

6-hydroxy-2,4-dioxo-N-(4-sulfamoylphenyl)-1,2,3,4-tetrahydropyrimidine-5-carboxamide or 5-(N-(4'-sulfamoylphenyl))carbamoylbarbituric acid 2. The compound wherein X is O, W is absent and Z is —$NHSO_2CH_3$, for example the compound having a structure represented by Formula ($I_b$):

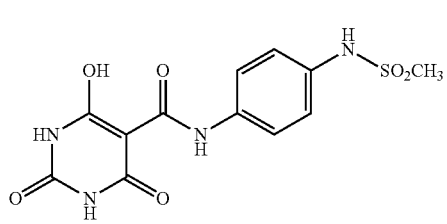

Formula (I$_b$)

6-hydroxy-N-(4-(methylsulfonamido)phenyl)-2,4-dioxo-1,2,3,4-tetrahydropyrimidine-5-carboxamide or 5-(N-(4'-(methylsulfonamido)phenyl))carbamoylbarbituric acid 3. The compound wherein, X is O, W is absent and Z is —NHSO$_2$CF$_3$, for example the compound having a structure represented by Formula (I$_c$):

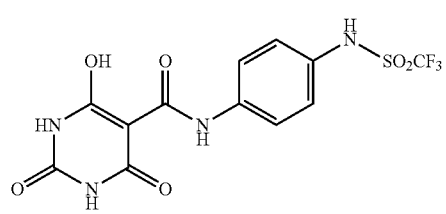

Formula (I$_c$)

6-hydroxy-2,4-dioxo-N-(4-(trifluoromethylsulfonamido)phenyl)-1,2,3,4-tetrahydropyrimidine-5-carboxamide or 5-(N-(4'-(trifluoromethylsulfonamido)phenyl))carbamoylbarbituric acid 4. The compound wherein, X is O, Z is absent and W is 4'-hydroxy and 5'-CH$_2$OH, for example the compound having a structure represented by Formula (I$_d$):

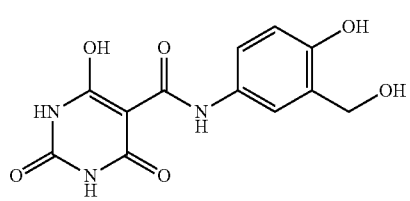

Formula (I$_d$)

6-hydroxy-N-(4-hydroxy-3-(hydroxymethyl)phenyl)-2,4-dioxo-1,2,3,4-tetrahydropyrimidine-5-carboxamide or 5-(N-(4'-hydroxy-3'-(hydroxymethyl)phenyl))carbamoylbarbituric acid 5. The compound wherein X is O; W is absent and Z is —CH$_2$CO$_2$H, for example the compound having a structure represented by Formula (I$_e$):

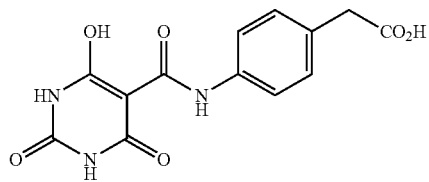

Formula (I$_e$)

2-(4-(6-hydroxy-2,4-dioxo-1,2,3,4-tetrahydropyrimidine-5-carboxamido)phenyl)acetic acid or 5-(N-(4'-carboxymethylphenyl))carbamoylbarbituric acid 6. The compound wherein X is O, W is absent, and Z is 5-keto-1,2,4-oxadiazole, for example the compound having a structure represented by Formula (I$_f$):

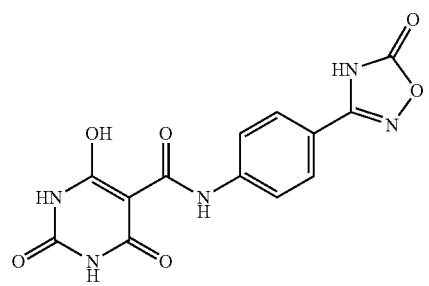

Formula (I$_f$)

6-hydroxy-2,4-dioxo-N-(4-(5-oxo-4,5-dihydro-1,2,4-oxadiazol-3-yl)phenyl)-1,2,3,4-tetrahydropyrimidine-5-carboxamide or 5-(N-(4'-(5'-oxo-4',5'-dihydro-1',2',4'-oxadiazol-3'-yl)phenyl))carbamoylbarbituric acid 7. The compound wherein X is S, W is absent, and Z is 5-keto-1,2,4-oxadiazole, for example the compound having a structure represented by Formula (I$_g$):

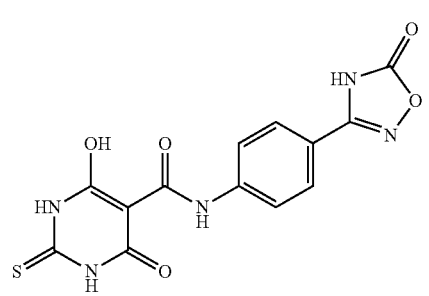

Formula (I$_g$)

6-Hydroxy-4-oxo-N-(4-(5-oxo-4,5-dihydro-1,2,4-oxadiazol-3-yl)phenyl)-2-thioxo-1,2,3,4-tetrahydropyrimidine-5-carboxamide or 5-(N-(4'-(5'-oxo-4',5'-dihydro-1',2',4'-oxadiazol-3'-yl)phenyl))carbamoyl-2-thioxobarbituric acid 8. The compound wherein X is O, W is absent, and Z is 5-ketoisoxazole, for example the compound having a structure represented by Formula (I$_h$):

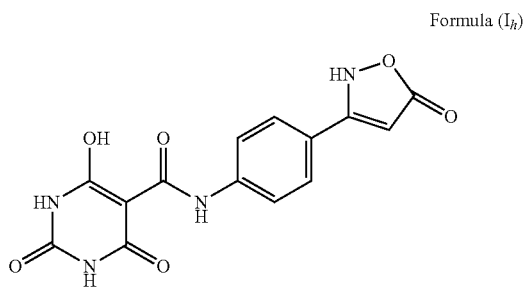 [SMILES: O=C(Nc1ccc(-c2cc(=O)o[nH]2)cc1)c1c(O)[nH]c(=O)[nH]c1=O]

Formula (I_h)

Figure 2:
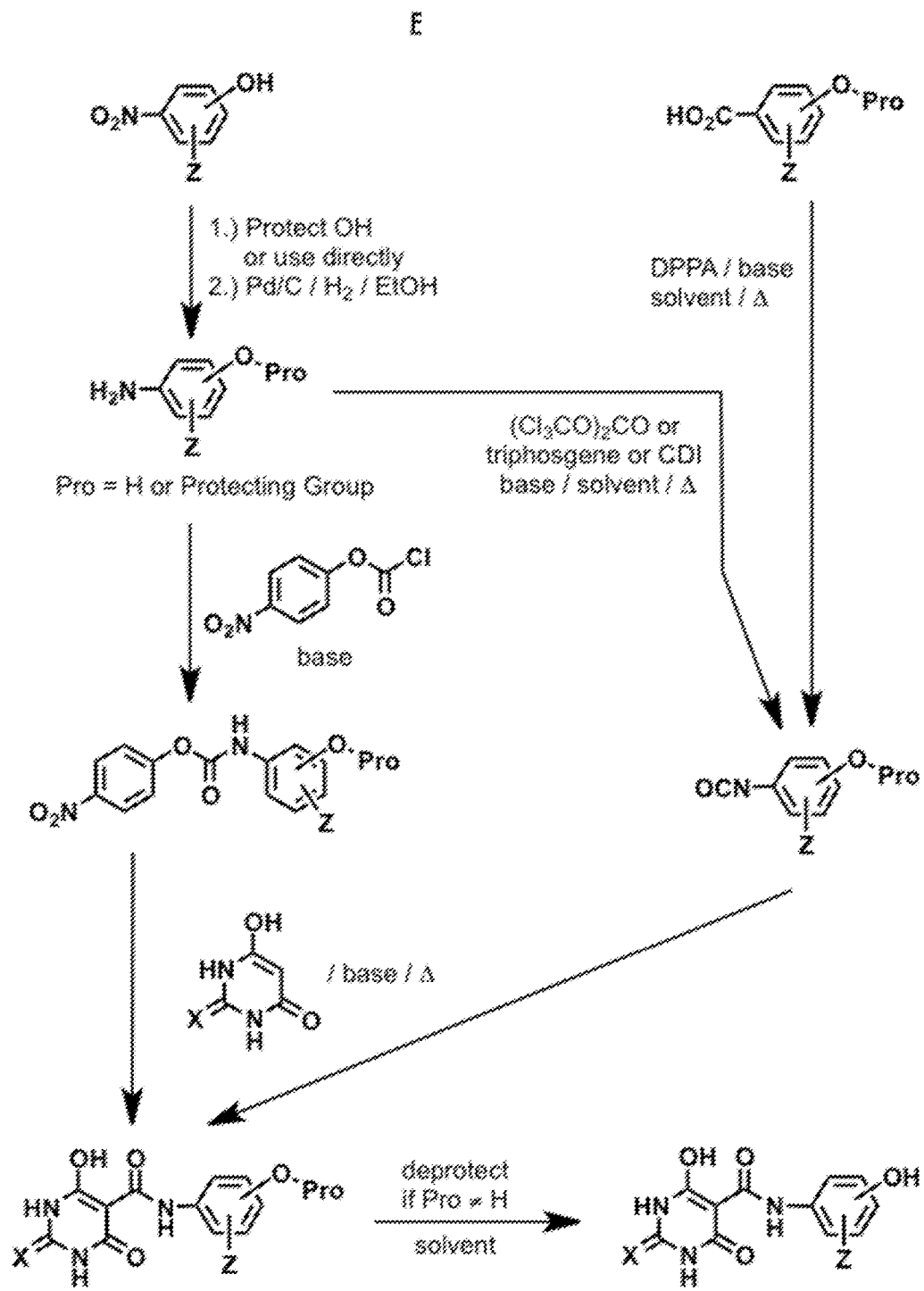
FIG. 2 illustrates a general synthesis scheme for preparation of compounds having a structure represented by Formula (I) when W=OH.
Figure 20:
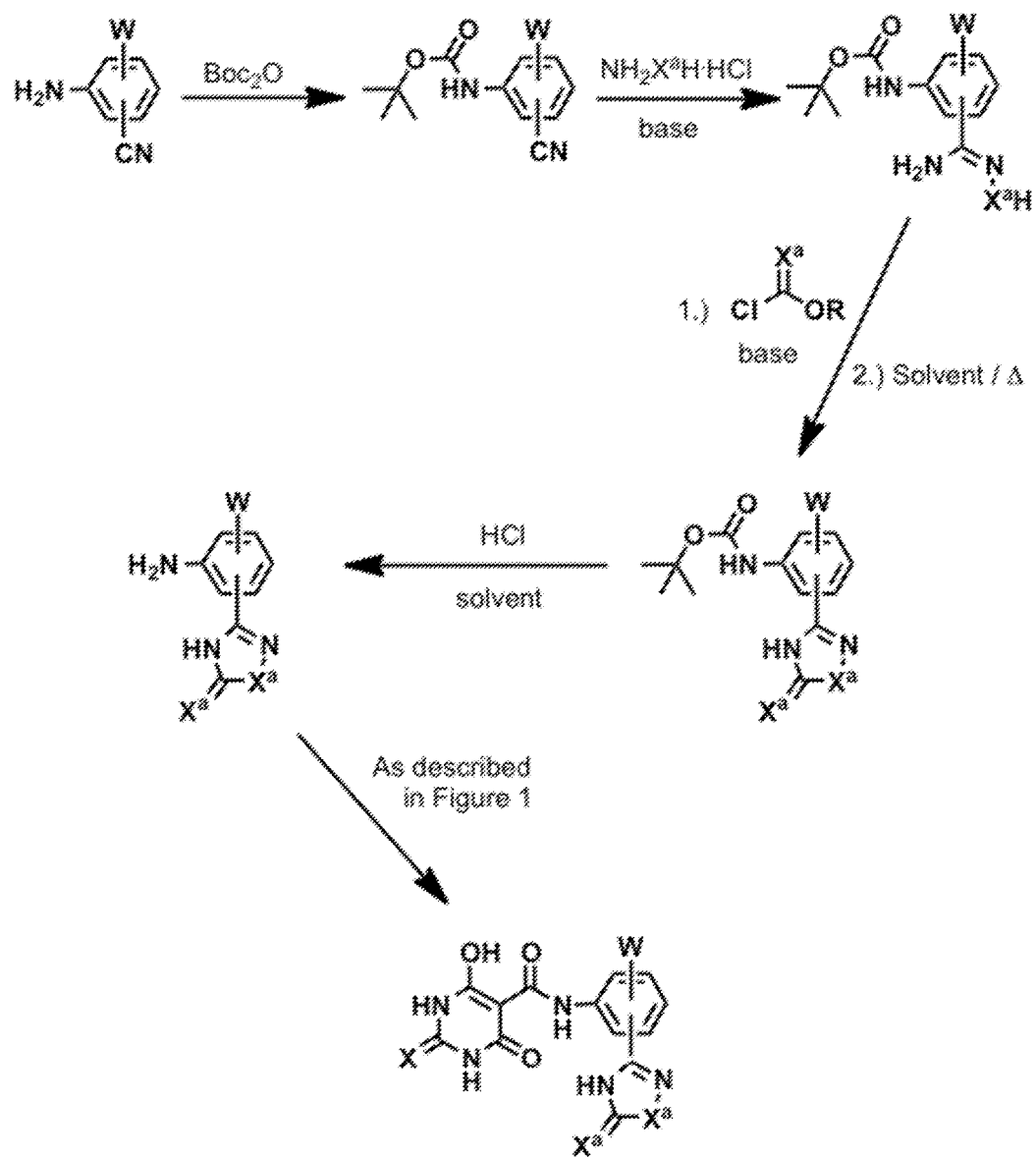
FIG. 20 illustrates a general synthesis scheme for preparation of compounds having a structure represented by Formula (I) when Z is

6-hydroxy-2,4-dioxo-N-(4-(5-oxo-4,5-dihydroisoxazol-3-yl)phenyl)-1,2,3,4-tetrahydropyrimidine-5-carboxamide or 5-(N-(4'-(5'-oxo-4',5'-dihydroisoxazol-3'-yl)phenyl))carbamoylbarbituric acid Compounds having structures represented by Formula (I) may generally be prepared as shown in FIG. 1 (when W is absent) or FIG. 2 (when W=OH) or FIG. 20 (when X=ketooxadiazole). The process illustrated in FIG. 1 centers around coupling the appropriate activated side chain with either barbituric acid (X=O) or thiobarbituric acid (X=S) to directly generate compounds of the formula (I). There are numerous ways to generate the activated side chains, including generation of the para-nitrophenylcarbamate of the corresponding aryl amine or production of the corresponding isocyanate of the amine. The para-nitrophenylcarbamates can be prepared by reaction of the amine with 4-nitrophenyl chloroformate. The isocyanates can be prepared by standard methods, such as reaction of the corresponding aryl amine with 1,1'-carbonyldiimidazole or similar reagent or by reaction of the corresponding carboxylic acid with diphenyl phosphorazidate. Furthermore, one skilled in the art will recognize that in addition to these there are numerous methods to activate the amine towards reaction with either barbituric acid (X=O) or thiobarbituric acid (X=S).

Figure 12:
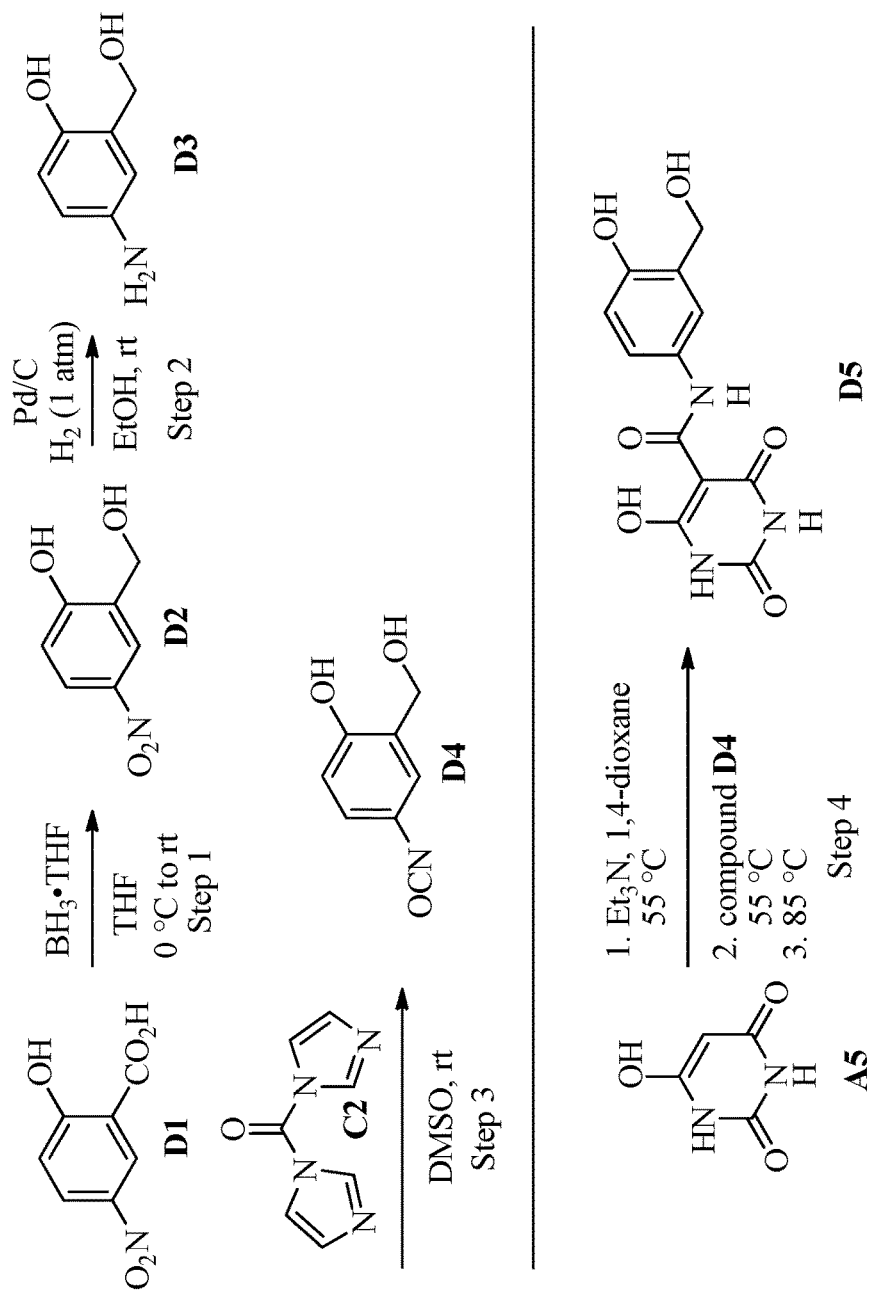
FIG. 12 illustrates an exemplary synthesis scheme for preparation of a compound having a structure represented by Formula (I$_d$).

A general synthesis process for compounds of Formula (I) when W is present (W=OH) is illustrated in FIG. 2. It follows essentially the same sequence as illustrated for FIG. 1 except that protection of the phenol (W=OH) may be necessary in certain cases, such as its benzyl ether or acetate. After coupling the appropriate activated side chain with either barbituric acid (X=O) or thiobarbituric acid (X=S), the protecting group may be removed by standard methods, such as hydrolytic cleavage for the acetate or reductions for the benzyl ether. In certain cases protection of the phenol (W=OH) may not be necessary as illustrated in FIG. 12.

The synthesis of compounds represented by Formula (I) when X is a 5-oxo-4,5-dihydro-1,2,4-oxadiazole ring also generally proceeds as described in FIG. 1. However, the 5-oxo-4,5-dihydro-1,2,4-oxadiazole ring will be constructed initially as depicted in FIG. 20. The synthetic process for the 5-oxo-4,5-dihydro-1,2,4-oxadiazole ring is also described in Kohara et al., *J. Med. Chem*, 39, 5228 (1996).

In a second aspect, the invention relates to a compound that is a modification of the compounds having a structure represented by Formula (I), wherein the phenyl group is substituted with a substituted or unsubstituted tetrazole. These compounds have a structure represented by Formula (II):

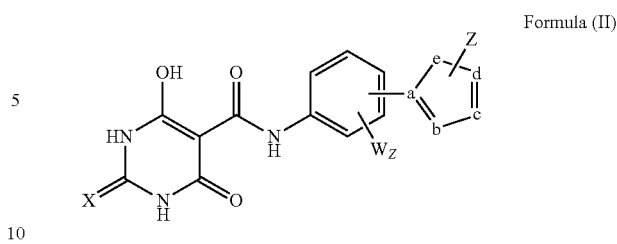

Formula (II)

wherein

X is O or S; and

Each Z is independently present or absent and, if present, is independently selected from one or more halogen atoms, —CN, —CF$_3$, —OR$^2$, —C(O)R$^2$, SR$^2$, —S(O)$_f$R$^3$ where f is 1 or 2, —N(R$^2$)$_2$, —NO$_2$, —CO$_2$R$^2$, —OCO$_2$R$^3$, OC(O)R$^2$, —CON(R$^2$)$_2$, —NR$^2$C(O)R$^2$, —SO$_2$(NR$^2$)$_2$, —NR$^2$SO$_2$R$^3$, —NR$^2$SO$_2$N(R$^2$)$_2$, —NR$^2$C(O)N(R$^2$)$_2$, alkyl, aryl, alkenyl and alkynyl;

wherein each R$^2$ is independently H, alkyl or aryl;

wherein each R$^3$ is independently alkyl or aryl, optionally substituted with one or more halogen atoms or OR$^2$; and wherein a, b, c, d, and e are each independently carbon or nitrogen, with the proviso that at least one of a, b, c, d and e is nitrogen and Z is not connected directly to a nitrogen, except that Z may optionally be connected to a nitrogen at a, b, c, d, or e by replacement of the hydrogen of an NH group when Z is —C(O)R$^2$, —S(O)$_f$R$^3$, —CO$_2$R$^3$, —CON(R$^2$)$_2$, —SO$_2$N(R$^2$)$_2$, alkyl, aryl, alkenyl or alkynyl. It will be understood that direct connection of Z to nitrogen requires the a, b, c, d or e nitrogen to which Z is to be directly connected to be in the form of NH, such that the hydrogen can be replaced by Z.

Specific examples of compounds having a structure represented by Formula (II) include the following compounds:

1. The compound wherein X is O; both Z are absent; b, c, and d are N; e is NH, and; a is C, for example the compound having a structure represented by Formula (II$_a$):

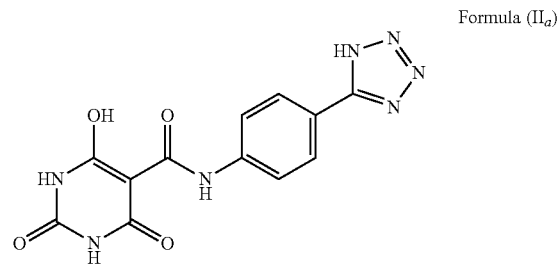

Formula (II$_a$)

N-(4-(2H-tetrazol-5-yl)phenyl)-6-hydroxy-2,4-dioxo-1,2,3,4-tetrahydropyrimidine-5-carboxamide or 5-(N-(4'-(2'H-tetrazol-5'-yl)phenyl))carbamoylbarbituric acid 2. The compound wherein X is S; both Z are absent; b, c, and d are N; e is NH, and a is C, for example the compound having a structure represented by Formula (II$_b$):

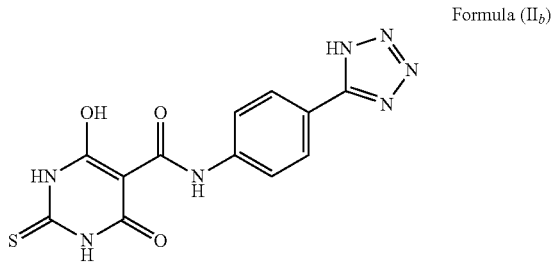 [SMILES: O=C(Nc1ccc(-c2nnn[nH]2)cc1)c1c(O)[nH]c(=S)[nH]c1=O]

Formula (II$_b$)

N-(4-(2H-tetrazol-5-yl)phenyl)-6-hydroxy-4-oxo-2-thioxo-1,2,3,4-tetrahydropyrimidine-5-carboxamide or 5-(N-(4'-(2'H-tetrazol-5'-yl)phenyl))carbamoyl-2-thioxobarbituric acid 3. The compound wherein X is O; both Z are absent; a, c, d and e are N, and; b is CH, for example the compound having a structure represented by Formula (II$_c$):

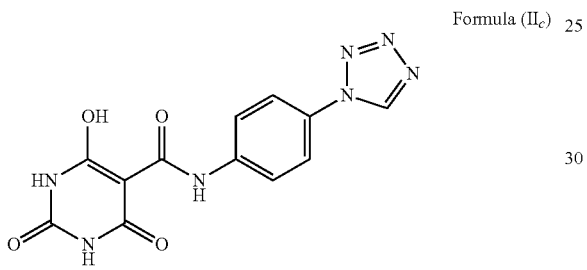

Formula (II$_c$)

N-(4-(1H-tetrazol-1-yl)phenyl)-6-hydroxy-2,4-dioxo-1,2,3,4-tetrahydropyrimidine-5-carboxamide or 5-(N-(4'-(1'H-tetrazol-1'-yl)phenyl))carbamoylbarbituric acid 4. The compound wherein X is O; both Z are absent; c is N; e is NH; a, b and d are CH; for example the compound having a structure represented by Formula (II$_d$):

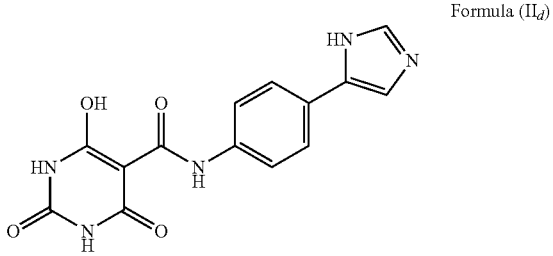 [SMILES: O=C(Nc1ccc(-c2cnc[nH]2)cc1)c1c(O)[nH]c(=O)[nH]c1=O]

Formula (II$_d$)

N-(4-(1H-imidazol-5-yl)phenyl)-6-hydroxy-2,4-dioxo-1,2,3,4-tetrahydropyrimidine-5-carboxamide or 5-(N-(4'-(1'H-imidazol-5'-yl)phenyl))carbamoylbarbituric acid 5. The compound wherein X is O, both Z are absent; c and d are N; e is NH; a and b are C, for example the compound having a structure represented by Formula (II$_e$):

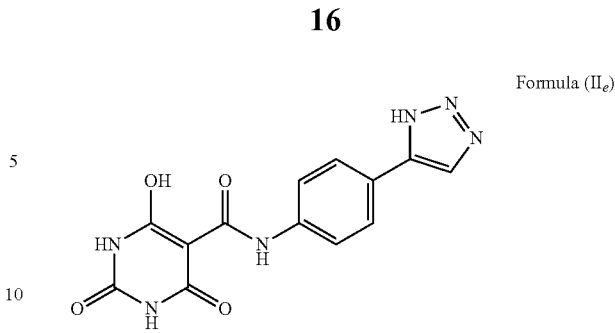

Formula (II$_e$)

N-(4-(1H-1,2,3-triazol-5-yl)phenyl)-6-hydroxy-2,4-dioxo-1,2,3,4-tetrahydropyrimidine-5-carboxamide or 5-(N-(4'-(1'H-1',2',3'-triazol-5'-yl)phenyl))carbamoylbarbituric acid 6. The compound wherein X is S, both Z are absent; c and d are N; e is NH; a and b are C, for example the compound having a structure represented by Formula (II$_f$):

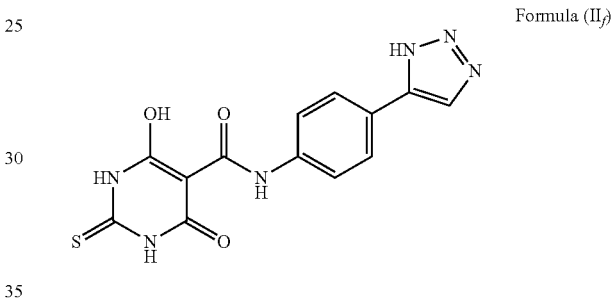

Formula (II$_f$)

Figure 3:
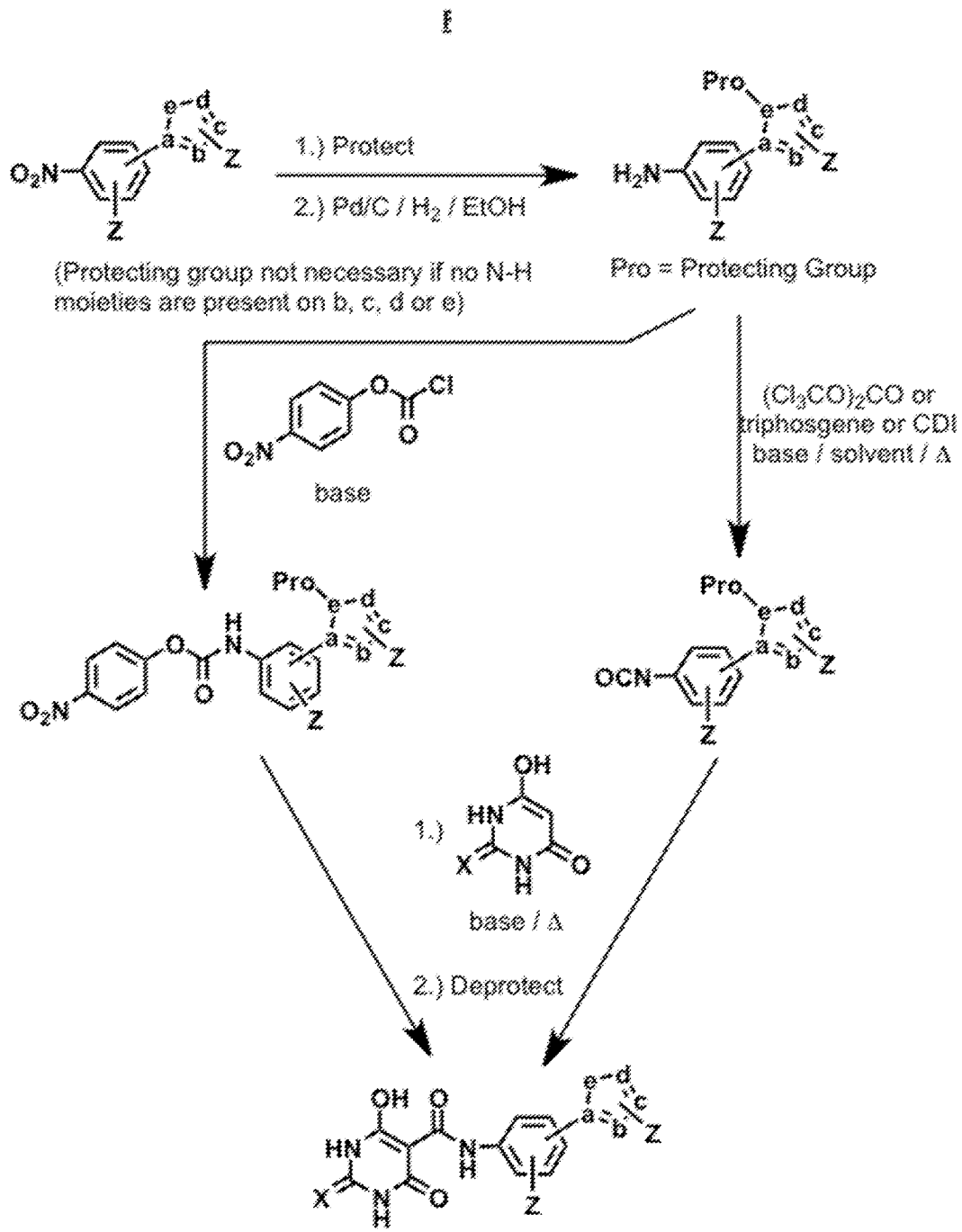
FIG. 3 illustrates a general synthesis scheme for preparation of compounds having a structure represented by Formula (II).

N-(4-(1H-1,2,3-triazol-5-yl)phenyl)-6-hydroxy-4-oxo-2-thioxo-1,2,3,4-tetrahydropyrimidine-5-carboxamide or 5-(N-(4'-(1'H-1',2',3'-triazol-5'-yl)phenyl))carbamoyl-2-thioxobarbituric acid Compounds having structures represented by Formula (II) may generally be prepared according to the synthesis scheme illustrated in FIG. 3. Compounds having structures represented by Formula (II) include compounds in which one of b, c, d or e can exist as N—H. In such cases this functionality may be protected with an appropriate protecting group, such as THP. Once the appropriate intermediate is protected, its conversion to the appropriate activated can be accomplished, analogous to the sequence described for FIG. 1. When OH is present (W=OH), compounds having structures represented by Formula (II) can generally be prepared as illustrated in FIG. 2. After coupling the appropriate activated side chain with either barbituric acid (X=O) or thiobarbituric acid (X=S), the protecting group may be removed by standard methods, such as aqueous acid to remove the THP group. In cases where b, c, d or e does not have an N—H, it is not necessary to utilize a protecting group, as the compounds of formula (II) are generated directly after coupling with either barbituric acid (X=O) or thiobarbituric acid (X=S). It is understood that compounds of the Formula (II) can exist as tautomers. It is to be understood that the structure illustrated in Formula (II) encompasses all possible tautomers.

In a second aspect, the invention relates to a compound that is a modification of the compounds having structures represented by Formula (I), wherein the phenyl group is replaced with benzotriazole. These compounds have a structure represented by Formula (III):

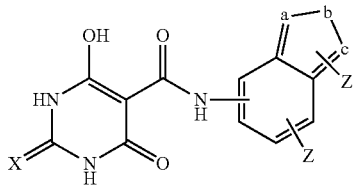

Formula (III)

wherein
X is O or S; and
Each Z is independently present or absent and, if present, is independently selected from one or more halogen atoms, —CN, —CF$_3$, —OR$^2$, —C(O)R$^2$, SR$^2$, —S(O)$_f$R$^3$ where f is 1 or 2, —N(R$^2$)$_2$, —NO$_2$, —CO$_2$R$^2$, —OCO$_2$R$^3$, OC(O)R$^2$, —CON(R$^2$)$_2$, —NR$^2$C(O)R$^2$, —SO$_2$(NR$^2$)$_2$, —NR$^2$SO$_2$R$^3$, —NR$^2$SO$_2$N(R$^2$)$_2$, —NR$^2$C(O)N(R$^2$)$_2$, alkyl, aryl, alkenyl and alkynyl;
wherein each R$^2$ is independently H, alkyl or aryl;
wherein each R$^3$ is independently alkyl or aryl, optionally substituted with one or more halogen atoms or OR$^2$; and
a, b, and c, are each independently carbon or nitrogen, with the proviso that at least one of a, b, and c is nitrogen and Z is not connected directly to a nitrogen, except that Z may optionally be connected to a nitrogen at a, b, or c by replacement of the hydrogen of an NH group when Z is —C(O)R$^2$, —S(O)$_f$R$^3$, —CO$_2$R$^3$, —CON(R$^2$)$_2$, alkyl, aryl, alkenyl or alkynyl. It will be understood that direct connection of Z to nitrogen requires that the a, b, or c nitrogen to which Z is to be directly connected be in the form of NH, such that the hydrogen can be replaced by Z.

It is to be understood that the five-membered ring of the benzotriazole group in Formula (III) can exist as several tautomers. All tautomers are intended to be included in the structure of Formula (III) shown above.

Specific examples of compounds having a structure represented by Formula (III) include the following compounds:
1. The compound wherein X is O; both Z are absent; a and c, are N; and b is NH, for example the compound having a structure represented by Formula (IIIa):

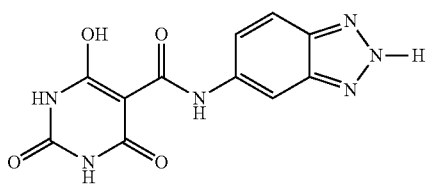

Formula (III$_a$)

N-(1H-benzo[d][1,2,3]triazol-6-yl)-6-hydroxy-2,4-dioxo-1,2,3,4-tetrahydropyrimidine-5-carboxamide or 5-(N-(1'H-benzo[d][1',2',3']triazol-6'-yl))carbamoylbarbituric acid The compound having a structure represented by Formula (III$_a$) is illustrated above as the B tautomer of the five-member ring of the benzotriazole group. It is to be understood that the structure illustrated in Formula (III$_c$) is intended to encompass tautomers A and C as well as the specific tautomer shown above.

Figure 4:
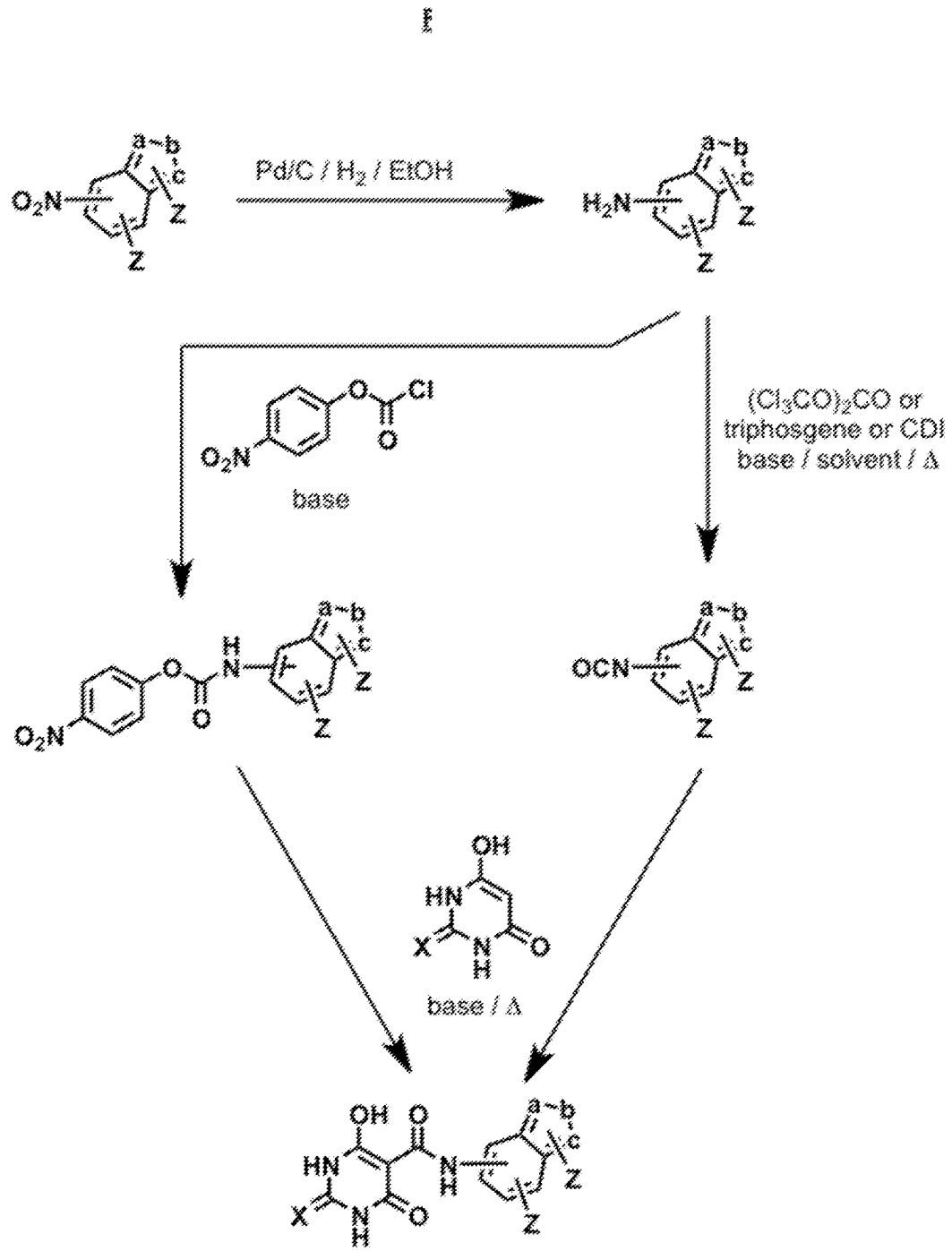
FIG. 4 illustrates a general synthesis scheme for preparation of compounds having a structure represented by Formula (III).

Compounds having structures represented by Formula (III) may be synthesized generally as illustrated in FIG. 4. These compounds include compounds in which one of a, b, or c exist as N—H. In such cases one can protect this functionality with an appropriate protecting group, such as THP, however, it is not always necessary. The coupling of the appropriate activated side chain with either barbituric acid (X=O) or thiobarbituric acid (X=S) proceeds as described for synthesis of the compounds illustrated in FIG. 3.

As disclosed herein, reference to compounds having a structure represented by Formula (I), Formula (II), Formula (III), or a combination thereof, is intended to include all compounds falling within the generic structure as well as the specific embodiments of these compounds discussed above (Formula (I$_{a-h}$), Formula (II$_{a-f}$), and Formula (III$_a$) and their tautomers).

In a first aspect, the invention provides methods for reducing uric acid levels in the blood or serum of a subject comprising administering a compound having a structure represented by Formula (I), Formula (II), Formula (III), or a combination thereof, to the subject in an amount effective to reduce blood or serum uric acid levels. It is to be understood that all such methods for reducing uric acid levels correspond to a compound having a structure represented by Formula (I), Formula (II), Formula (III), Formula (IV), or a combination thereof, for use in medicine as well as a compound having a structure represented by Formula (I), Formula (II), or Formula (III), or a combination thereof, for use in the treatment of elevated uric acid levels. Typically, the compound having a structure represented by Formula (I), Formula (II), Formula (III), or a combination thereof, will be administered when the level of uric acid in the blood of the subject is elevated, i.e., in the upper range of normal or above normal levels. One skilled in the art would further recognize that continued administration after normal uric acid levels are achieved is also contemplated in order to maintain uric acid levels within the normal range and to reduce the overall body burden of uric acid that may have occurred due to previously sustained hyperuricemia. Accordingly, methods for preventing elevation of uric acid levels in blood or serum are also an aspect of the invention. It is to be understood that all such methods for preventing elevation of uric acid levels correspond to a compound having a structure represented by Formula (I), Formula (II), or Formula (III), or a combination thereof, for use in medicine as well as a compound having a structure represented by Formula (I), Formula (II), Formula (III), or a combination thereof, for use in the prevention of elevated uric acid levels.

Normal uric acid levels in blood are generally in the range of 4.3 mg/dL to 8.0 mg/dL. In certain embodiments, a compound having a structure represented by Formula (I), Formula (II), Formula (III), or a combination thereof, is administered to a subject with a blood uric acid level of at least about 6 mg/dL. Administration may continue until a blood uric acid level of about 6.0 mg/dL or less is reached; however, it is generally considered to be beneficial to maintain uric acid levels below this target in patients with disorders of uric acid metabolism.

In certain embodiments, the invention provides methods of treating a disorder of uric acid metabolism caused by, or associated with, elevated uric acid levels in blood or serum (hyperuricemia). The method of treating such disorders comprises administering a compound having a structure represented by Formula (I), Formula (II), Formula (III), or a combination thereof, to a subject in need thereof in an amount effective to reduce serum uric acid levels, thereby treating the disorder of uric acid metabolism in the subject. These disorders are associated with, or caused by, elevated uric acid levels in blood or serum which are in the upper range of normal or above normal, and include gout, hyperuricemia, kidney disease, arthritis, kidney stones, kidney failure, urolithiasis, plumbism, hyperparathyroidism, psoriasis, inborn genetic errors of metabolism, sarcoidosis and cardiovascular disease. These drugs are particularly useful for treating gout and kidney disease (including acute uric acid nephropathy, chronic urate nephropathy, and uric acid nephrolithiasis). In addition, treatment of some cancers with chemotherapy leads to the release of large amounts of uric acid into the blood, which can damage the kidneys. Chemotherapy-induced hyperuricemia, particularly the disorder known as "tumor lysis syndrome," may also be treated, prevented or ameliorated according to the methods of the invention. Administration of a compound having a structure represented by Formula (I), Formula (II), Formula (III), or a combination thereof, to a subject with hyperuricemia, such as a subject suffering from gout, kidney disease, or a risk of inducing elevated uric acid levels due to chemotherapy, treats, prevents or ameliorates these disorders by reducing uric acid levels in blood, or preventing or controlling their level of increase. In specific embodiments, the disorder of uric acid metabolism treated by administration of a compound having a structure represented by Formula (I), Formula (II), Formula (III), or a combination thereof, is gout. It is to be understood that all such methods for treating disorders of uric acid metabolism caused by, or associated with, elevated uric acid levels in blood or serum (hyperuricemia) correspond to a compound having a structure represented by Formula (I), Formula (II), or Formula (III), or a combination thereof, for use in medicine as well as a compound having a structure represented by Formula (I), Formula (II), Formula (III), or a combination thereof, for use in treating disorders of uric acid metabolism caused by, or associated with, elevated uric acid levels in blood or serum.

The dose of a compound having a structure represented by Formula (I), Formula (II), Formula (III), or a combination thereof, administered to the subject may be any dose sufficient to achieve a desired reduction in uric acid levels in blood or serum over the time-course of administration. In certain embodiments, a daily dose of about 20 to about 1,500 mg/m$^2$/day is administered. In other embodiments, a daily dose of about 20 to about 500 mg/m$^2$/day, about 20 to about 250 mg/m$^2$/day, about 20 to about 150 mg/m$^2$/day or about 20 to about 100 mg/m$^2$/day is administered. In other embodiments, a daily dose of about 50 to about 1,500 mg/m$^2$/day is administered. In other embodiments, a daily dose of about 50 to about 500 mg/m$^2$/day, about 50 to about 150 mg/m$^2$/day, about 50 to about 100 mg/m$^2$/day, or about 20 to about 100 mg/m$^2$/day is administered.

In certain embodiments of any of the foregoing methods, a compound having a structure represented by Formula (I), Formula (II), Formula (III), or a combination thereof, is administered to the subject parenterally, intraperitoneally, intravenously, intranasally, intrarectally, or orally. Particularly useful routes of administration include injection, infusion, or oral administration. The amount of the drug administered per dose is an amount sufficient to achieve a reduction in uric acid levels in blood or serum, to prevent elevation of uric acid levels in blood or serum, or to treat or prevent a disorder of uric acid metabolism over the course of therapy. One skilled in the art will recognize that individualization of dosage based on a patient's body composition or his/her hypouricemic response to treatment may be medically necessary or desirable.

The drug(s) may be administered to the subject either intermittently or continuously over a period of time in order to achieve the desired reduction in uric acid levels in blood or serum, or to treat a disorder of uric acid metabolism. For example, doses may be administered intermittently several times per day, or at daily, once, twice or three times per week, or monthly intervals. In a specific example, a compound having a structure represented by Formula (I), Formula (II), Formula (III), or a combination thereof, may be administered to the subject by continuous intravenous infusion over 24 hours for about five days. Alternatively, a compound having a structure represented by Formula (I), Formula (II), Formula (III), or a combination thereof, may be administered to the subject by intravenous infusion over about 1 hour to about 5 hours for about five consecutive days. In a specific example, a compound having a structure represented by Formula (I), Formula (II), Formula (III), or a combination thereof, may be administered to the subject by intramuscular injection or by intravenous infusion over about 10 minutes for about five consecutive days. In further specific embodiments, a compound having a structure represented by Formula (I), Formula (II), Formula (III), or a combination thereof, may be administered to the subject by daily bolus injections for about five days. The period of time of administration in any of the foregoing protocols may be modified to achieve the desired reduction in uric acid levels, including about 2 days, about 3 days, about 4 days, about one week or about two weeks of administration, or for longer periods in repeated treatment cycles, and these treatments may be repeated at intervals of every two to every 10 weeks.

In addition to continuous intravenous infusion or bolus injection, a compound having a structure represented by Formula (I), Formula (II), Formula (III), or a combination thereof, may be administered to the subject orally. In this embodiment, an oral dose in amounts as described above may be administered in one, two, three or four administrations per day for 1, 2, 3, 4, or 5 days to achieve the desired reduction in uric acid levels. In further embodiments, the oral dose as described above may be administered once per day, or in one, two, three or four administrations per day for one week or two weeks, to achieve the desired reduction in uric acid levels.

It will be appreciated that a subject in need of reduced levels of uric acid in blood or serum, or in need of treatment of a disorder of uric acid metabolism, will be treated more aggressively initially to achieve the desired reduction in uric acid levels. Following initial therapy and reduction of uric acid levels to normal or sub-normal levels, the subject may be further treated over a period of time, or over a lifetime, to maintain normal or sub-normal levels of uric acid in blood or serum and prevent elevation of uric acid levels subsequent to the initial treatment. The maintenance or preventive protocol may comprise reduced dosages and/or less frequent administration of a compound having a structure represented by Formula (I), Formula (II), Formula (III), or a combination thereof, as necessary or desired to maintain normal or sub-normal uric acid levels in blood or serum. For example, in a maintenance protocol the drug(s) may be administered daily, weekly, monthly, or intermittently as uric acid levels rise between treatment periods. Such maintenance protocols will serve to maintain normal or sub-normal uric acid levels for a prolonged period of time and reduce the subject's lifetime risk of developing a disorder of uric acid metabolism caused by, or associated with, prolonged hyperuricemia. The initial reduction of uric acid levels from above normal or high normal to normal or sub-normal, and maintenance of normal or sub-normal uric acid levels are both features included in treatment of a disorder of uric acid metabolism. It is anticipated that in certain embodiments, a typical patient will require daily treatment of varying duration, and that such daily treatment may be provided intermittently for life or for extended periods.

In certain embodiments of any of the foregoing methods, blood or serum uric acid levels of the subject are reduced by at least 25% compared to uric acid levels prior to administration of a compound having a structure represented by Formula (I), Formula (II), Formula (III), or a combination thereof. In certain further embodiments, blood or serum uric acid levels of the subject are reduced by 50% or more compared to levels prior to administration. In a specific embodiment, uric acid levels are reduced by about 75% even at daily doses of 500 mg/m$^2$/day or less.

In a second aspect of the invention methods are provided for treating a disorder of uric acid metabolism associated with, or caused by, elevated uric acid in blood or serum comprising administering to a subject in need thereof a compound having a structure represented by Formula (I), Formula (II), Formula (III), or a combination thereof, in an amount effective to reduce blood or serum uric acid levels, thereby treating the disorder of uric acid metabolism. Specific embodiments of the methods for treating a disorder of uric acid metabolism relating to dosing, routes of administration, initial therapy and maintenance therapy are as described above for reducing uric acid levels in blood or serum. The initial reduction in uric acid levels is typically rapid, and often occurs within 1-3 days. Upon reduction in uric acid levels to normal or sub-normal levels, continued maintenance or preventive therapy results in a detectable improvement in at least one symptom of elevated uric acid, for example reduced inflammation, reduced pain, slowing of development of deformities, reduced development of kidney stones, prevention of tumor lysis syndrome, or improvement in cardiovascular disease. One skilled in the art will recognize that prevention of recurrent symptoms due to recurrence of elevated serum uric acid levels, thereby necessitating extended treatment, would be highly desirable to maximize patient benefit.

In embodiments corresponding to the foregoing methods, the invention relates to use of a compound disclosed herein, or a combination thereof, for reducing uric acid levels in blood or serum of a subject in need thereof, preventing elevation of uric acid levels in blood or serum of a subject, or treating a disorder of uric acid metabolism caused by, or associated with, hyperuricemia. Each of the methods of treatment or prevention disclosed, including routes of administration, dosage and compounds administered, are also applicable to such uses of the compounds.

A further aspect of the invention provides a pharmaceutical composition comprising a compound having a structure represented by Formula (I), Formula (II), Formula (III), or a combination thereof, and a pharmaceutically acceptable carrier. In certain embodiments of the pharmaceutical compositions, the composition is formulated as a solution or tablet. Solutions or dispersions of the drug(s) can be prepared in water or saline. In certain embodiments of the pharmaceutical compositions, the pharmaceutically acceptable carrier is one or more component selected from the group consisting of one or more of a solvent, a dispersing agent, a coating (e.g., lecithin), a surfactant (e.g., hydroxypropylcellulose), a preservative (e.g., paraben, phenol, thimerosal, sorbic acid, chlorobutanol), an emulsion, an alcohol (e.g., ethanol), a polyol (e.g., glycerol, propylene glycol), and an isotonic agent (e.g., sugars, sodium chloride).

In certain embodiments of the foregoing pharmaceutical compositions, the composition is formulated for controlled release of the compound having a structure represented by Formula (I), Formula (II), Formula (III), or a combination thereof. In certain embodiments of the foregoing methods, a compound having a structure represented by Formula (I), Formula (II), Formula (III), or a combination thereof, is administered in a form for controlled release. The controlled release compositions may include pharmaceutically acceptable carriers or excipients which cause release of the active ingredient more slowly or which extend the duration of its action within the body. Examples of controlled release compositions include pharmaceutically acceptable carriers or excipients which delay absorption of the active ingredient (e.g., aluminum monostearate, gelatin, natural or synthetic hydrophilic gums). Alternatively, controlled release of the pharmaceutical composition may employ a device such as a pump, implant or transdermal patch.

In certain embodiments of the foregoing pharmaceutical compositions, the composition is formulated for improved oral bioavailability or extended release in the body. For example, microemulsions, particle size reduction and complexation technologies may be used to improve dissolution rates or equilibrium solubilities of the compounds. Other suitable chemical and physical means for improving oral bioavailability or extended release will also be known to those skilled in the art.

EXAMPLES

Figure 5:
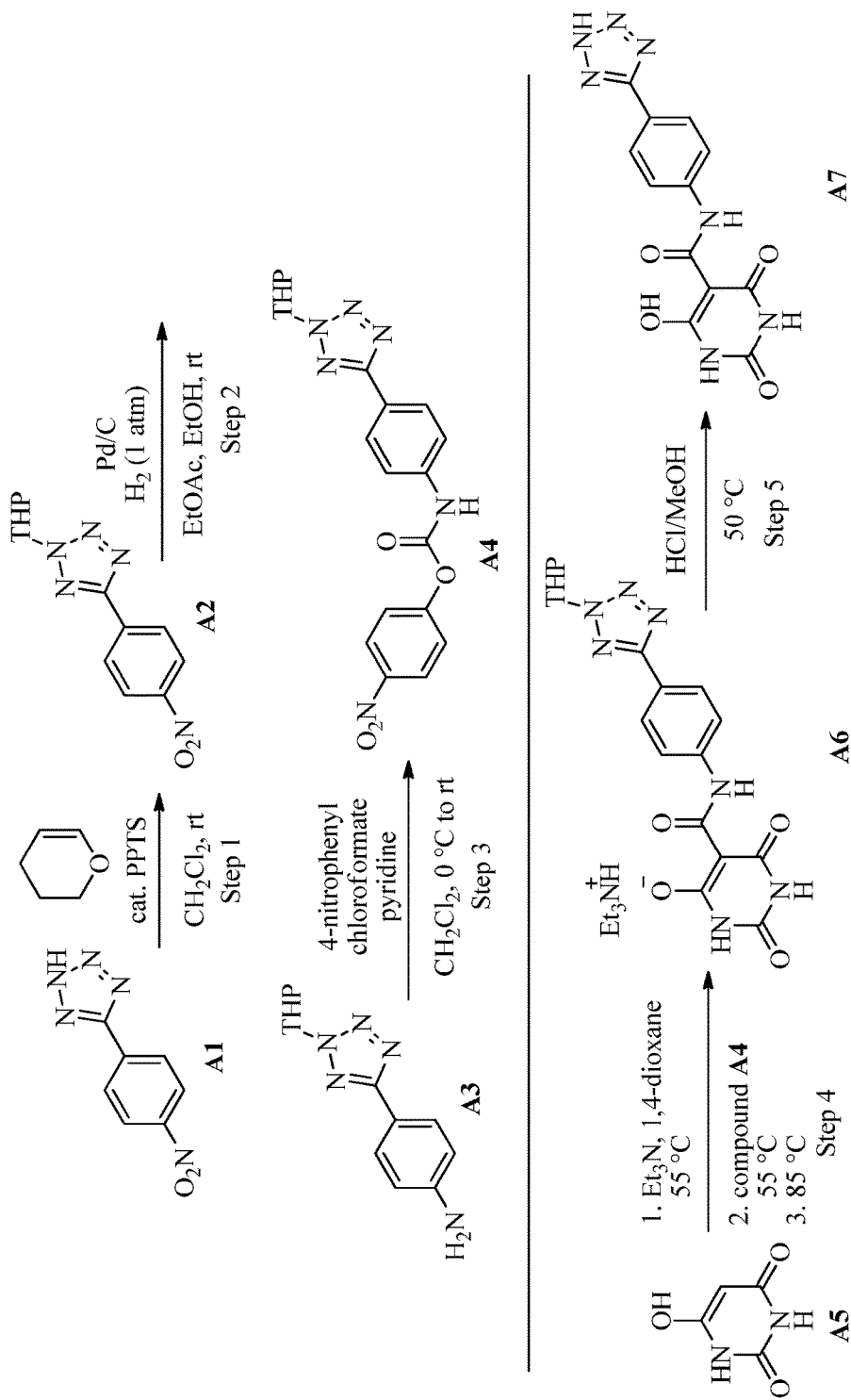
FIG. 5 illustrates an exemplary synthesis scheme for preparation of a compound having a structure represented by Formula (II$_a$).

Example 1: Preparation of N-(4-(2H-tetrazol-5-yl)phenyl)-6-hydroxy-2,4-dioxo-1,2,3,4-tetrahydropyrimidine-5-carboxamide (A7, Formula (IIa), with Reference to the Synthesis Scheme Illustrated in FIG. 5)

Step One.

5-(4-Nitrophenyl)-2-(tetrahydro-2H-pyran-2-yl)-2H-tetrazole (A2): To a stirred solution of compound A1 (1.91 g, 10.0 mmol) and pyridinium p-toluenesulfonate (0.250 g, 1.00 mmol) in anhydrous dichloromethane (100 mL) was added 3,4-dihydropyran (0.910 mL, 15.0 mmol) dropwise over 10 min at 0° C. under nitrogen. After the addition was completed, the reaction mixture was warmed to ambient temperature and stirred for 18 h. After this time, the reaction mixture was concentrated under reduced pressure. The residue was purified by flash column chromatography on silica gel eluting with 100% dichloromethane to afford compound A2 (2.38 g, 87%) as a light yellow solid: $^1$H NMR (300 MHz, DMSO-d$_6$) δ 8.44 (d, J=9.0 Hz, 2H), 8.35 (d, J=9.1 Hz, 2H), 6.28 (dd, J=7.6, 3.3 Hz, 1H), 3.90-3.81 (m, 2H), 2.42-2.28 (m, 1H), 2.26-2.14 (m, 1H), 2.10-1.97 (m, 1H), 1.86-1.70 (m, 1H), 1.70-1.60 (m, 2H).

Step Two.

4-(2-(Tetrahydro-2H-pyran-2-yl)-2H-tetrazol-5-yl)aniline (A3): A suspension of compound A2 (1.38 g, 5.00 mmol) and 10% palladium on carbon (50% wet, 0.300 g) in ethanol (50 mL) and ethyl acetate (50 mL) was stirred under 1 atmosphere of hydrogen at ambient temperature for 18 h. After this time, the reaction mixture was filtered through a short pad of Celite and the filtrate concentrated under reduced pressure. The residue obtained was purified by flash column chromatography on silica gel eluting with 0% to 100% dichloromethane/ethyl acetate to afford compound A3 (1.08 g, 88%) as a colorless oil: $^1$H NMR (300 MHz, CDCl$_3$) δ 8.00 (d, J=8.7 Hz, 2H), 6.97 (d, J=6.8 Hz, 2H), 6.02 (dd, J=7.9, 2.8 Hz, 1H), 4.60-3.60 (br s, 2H), 4.08-3.99 (m, 1H), 3.85-3.76 (m, 1H), 2.56-2.43 (m, 1H), 2.21-2.11 (m, 2H), 1.86-1.68 (m, 3H).

Step Three.

4-Nitrophenyl (4-(2-(tetrahydro-2H-pyran-2-yl)-2H-tetrazol-5-yl)phenyl)carbamate (A4): To a stirred solution of 4-nitrophenyl chloroformate (0.440 g, 2.18 mmol) in anhydrous dichloromethane (10 mL) was added a solution of compound A3 (0.540 g, 2.18 mmol) and pyridine (0.180 mL, 2.30 mmol) in anhydrous dichloromethane (20 mL) dropwise over 30 min at 0° C. under nitrogen. After the addition was completed, the reaction mixture was warmed to ambient temperature and stirred for 3 h. At this time, an additional portion of 4-nitrophenyl chloroformate (0.050 g, 0.250 mmol) and pyridine (0.090 mL, 1.20 mmol) were added and the mixture stirred at ambient temperature for an additional 15 h. After this time, the reaction mixture was concentrated under reduced pressure. The residue was treated with a mixture of diethyl ether (50 mL) and dichloromethane (10 mL), sonicated for 5 min and then stirred for 0.5 h. The resulting solid was collected by vacuum filtration, subsequently washed with diethyl ether (25 mL) and water (50 mL), and dried at 40° C. under high vacuum to afford compound A4 (0.270 g, 30%) as a white solid. The diethyl ether wash filtrate was concentrated. The resulting residue was triturated with water (50 mL), filtered, and dried at 40° C. under high vacuum to afford a second crop of compound A4 (0.245 g, 28%) as a white solid. Compound A4: $^1$H NMR (300 MHz, CDCl$_3$) δ 8.31 (d, J=9.3 Hz, 2H), 8.21 (d, J=8.7 Hz, 2H), 7.59 (d, J=8.6 Hz, 2H), 7.42 (d, J=9.2 Hz, 2H), 7.14 (br s, 1H), 6.06 (dd, J=7.8, 2.7 Hz, 1H), 4.07-4.03 (m, 1H), 3.86-3.80 (m, 1H), 2.56-2.47 (m, 1H), 2.25-2.14 (m, 2H), 1.88-1.66 (m, 3H).

Step Four.

6-Hydroxy-2,4-dioxo-N-(4-(2-(tetrahydro-2H-pyran-2-yl)-2H-tetrazol-5-yl)phenyl)-1,2,3,4-tetrahydropyrimidine-5-carboxamide Triethylamine Salt (A6): To a stirred suspension of barbituric acid A5 (0.084 g, 0.660 mmol) in anhydrous 1,4-dioxane (5 mL) was added triethylamine (90 uL, 0.660 mmol) at 55° C. under nitrogen. After stirring at 55° C. for 10 min, a solution of compound A4 (0.270 g, 0.660 mmol) in anhydrous 1,4-dioxane (2 mL) was added dropwise over 5 min. After the addition was completed, the mixture was heated at 85° C. for 4 h. After this time, the hot mixture was filtered, the filter cake washed with 1,4-dioxane (4×10 mL), and dried under reduced pressure to afford compound A6 (0.117 g, 35%) as a white solid: $^1$H NMR (300 MHz, DMSO-d$_6$) δ 12.31 (s, 1H), 9.62 (br s, 2H), 9.15-8.85 (br s, 1H), 7.94 (d, J=8.7 Hz, 2H), 7.70 (d, J=8.7 Hz, 2H), 6.16 (dd, J=8.0, 3.2 Hz, 1H), 3.96-3.72 (m, 2H), 3.08 (q, J=7.0 Hz, 6H), 2.40-2.24 (m, 1H), 2.18-1.97 (m, 2H), 1.83-1.70 (m, 1H), 1.70-1.57 (m, 2H), 1.17 (t, J=7.3 Hz, 9H); APCI MS, m/z 398 [M–H]$^-$.

Step Five.

N-(4-(2H-Tetrazol-5-yl)phenyl)-6-hydroxy-2,4-dioxo-1,2,3,4-tetrahydropyrimidine-5-carboxamide (A7, Formula (IIa)): A suspension of compound A6 (0.218 g, 0.436 mmol) in 1.25 M hydrogen chloride in methanol (10 mL) was heated at 55° C. for 3 h. After this time, the hot mixture was filtered, the filter cake washed with methanol (3×5 mL) and water (4×10 mL), and dried under high vacuum at 45° C. to afford compound A7 (0.120 g, 88%) as a white solid: $^1$H NMR (300 MHz, DMSO-d$_6$) δ 12.60-11.30 (br s, 2H), 11.80 (s, 1H), 8.07 (d, J=8.7 Hz, 2H), 7.80 (d, J=8.7 Hz, 2H); APCI MS, m/z 314 [M–H]$^-$.

Figure 6:
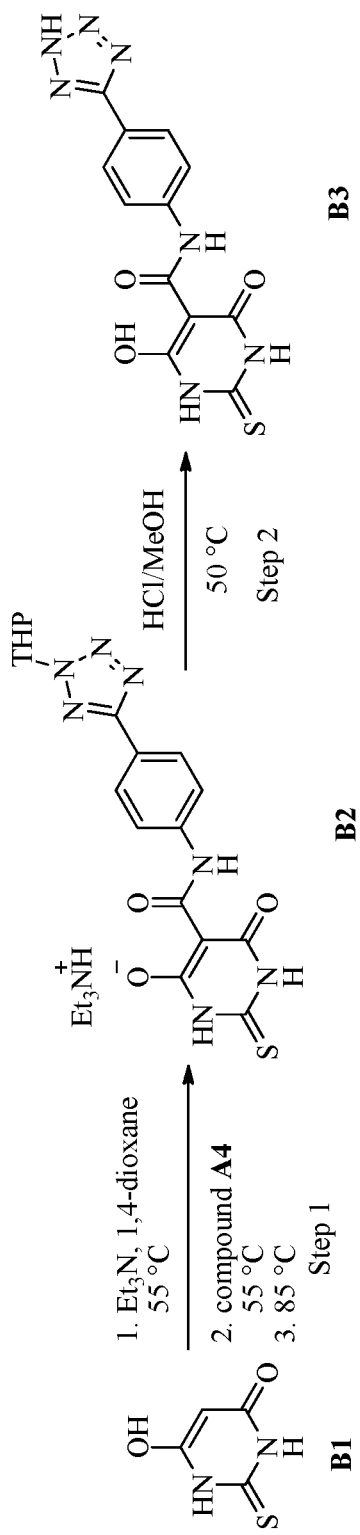
FIG. 6 illustrates an exemplary synthesis scheme for preparation of a compound having a structure represented by Formula (II$_b$).

Example 2: Preparation of N-(4-(2H-tetrazol-5-yl)phenyl)-6-hydroxy-4-oxo-2-thioxo-1,2,3,4-tetrahydropyrimidine-5-carboxamide (B3, Formula (IIb), with Reference to the Synthesis Scheme Illustrated in FIG. 6)

Step One.

6-Hydroxy-4-oxo-N-(4-(2-(tetrahydro-2H-pyran-2-yl)-2H-tetrazol-5-yl)phenyl)-2-thioxo-1,2,3,4-tetrahydropyrimidine-5-carboxamide Triethylamine Salt (B2): To a stirred suspension of thiobarbituric acid B1 (0.086 g, 0.600 mmol) in anhydrous 1,4-dioxane (3 mL) was added triethylamine (82 uL, 0.600 mmol) at 55° C. under nitrogen. After stirring for 10 min, a solution of compound A4 (0.245 g, 0.597 mmol) in anhydrous 1,4-dioxane (2 mL) was added dropwise over 5 min. The mixture was then heated at 85° C. for 3 h. After this time, the reaction mixture was concentrated to approximately one half the original volume. The resulting solid was collected by vacuum filtration, washed with 1,4-dioxane (4×10 mL), and dried under high vacuum to afford compound B2 (0.029 g, 12%) as a white solid. The 1,4-dioxane wash filtrate was concentrated to a volume of approximately 3 mL, the resulting solid was collected by vacuum filtration, washed with cold 1,4-dioxane (3×1 mL) and dried under high vacuum to afford a second crop of compound B2 (0.136 g, 44%) as an off-white solid. Compound B2: $^1$H NMR (300 MHz, DMSO-d$_6$) δ 12.12 (s, 1H), 10.98 (br s, 2H), 9.10-8.85 (br s, 1H), 7.96 (d, J=8.6 Hz, 2H), 7.72 (d, J=8.7 Hz, 2H), 6.17 (dd, J=7.9, 3.1 Hz, 1H), 3.93-3.73 (m, 2H), 3.11 (q, J=7.2 Hz, 6H), 2.40-2.25 (m, 1H), 2.20-1.98 (m, 2H), 1.85-1.70 (m, 1H), 1.70-1.58 (m, 2H), 1.17 (t, J=7.3 Hz, 9H); APCI MS, m/z 414 [M–H]$^-$.

Step Two.

N-(4-(2H-Tetrazol-5-yl)phenyl)-6-hydroxy-2,4-dioxo-1,2,3,4-tetrahydropyrimidine-5-carboxamide (B3, Formula IIb): A suspension of compound B2 (0.160 g, 0.385 mmol) in 1.25 M hydrogen chloride in methanol (10 mL) was stirred at 50° C. for 6 h. After this time, the hot mixture was filtered, the filter cake washed with methanol (3×5 mL), and dried under high vacuum at 45° C. to afford compound B3 (0.093 g, 90%) as a white solid:
$^1$H NMR (300 MHz, DMSO-d$_6$) δ 13.30-12.70 (br s, 2H), 11.62 (s, 1H), 8.07 (d, J=8.7 Hz, 2H), 7.81 (d, J=8.8 Hz, 2H); APCI MS, m/z 330 [M–H]$^-$.

Figure 7:
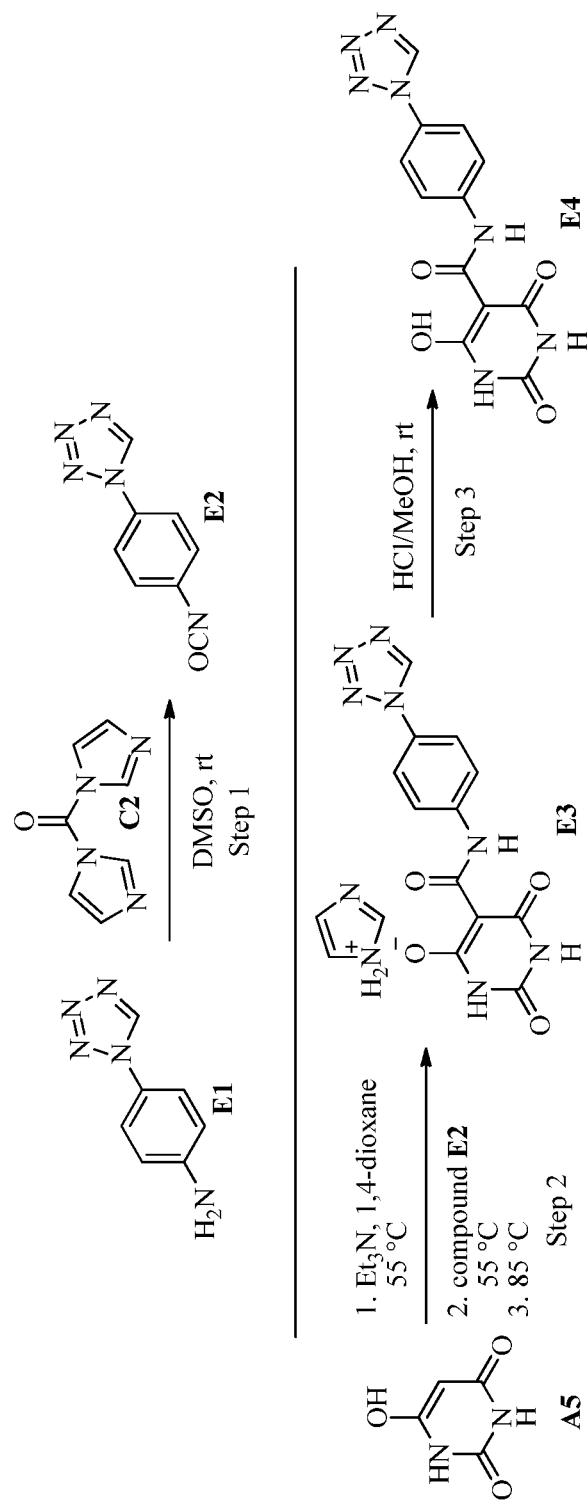
FIG. 7 illustrates an exemplary synthesis scheme for preparation of a compound having a structure represented by Formula (II$_c$).

Example 3: Preparation of N-(4-(1H-tetrazol-1-yl)phenyl)-6-hydroxy-2,4-dioxo-1,2,3,4-tetrahydropyrimidine-5-carboxamide (E4, Formula (IIc), with Reference to the Synthesis Scheme Illustrated in FIG. 7)

Steps One & Two.

N-(4-(1H-Tetrazol-1-yl)phenyl)-6-hydroxy-2,4-dioxo-1,2,3,4-tetrahydropyrimidine-5-carboxamide Imidazole Salt (E3): To a stirred solution of compound C2 (0.535 g, 3.30 mmol) in anhydrous DMSO (4 mL) was added compound E1 (0.484 g, 3.00 mmol) at ambient temperature under nitrogen. The reaction mixture was then stirred for 1 h to provide a solution of compound E2 in DMSO which was used directly in the subsequent step.

In a separate flask, to a suspension of barbituric acid A5 (0.384 g, 3.00 mmol) in anhydrous 1,4-dioxane (12 mL) was added triethylamine (0.303 g, 3.00 mmol) at 55° C. under nitrogen. After the addition was completed, the mixture was stirred for 5 min. Then, to this mixture was added the compound E2 solution in DMSO. The resulting mixture was heated to 85° C. for 3 h. After cooling to ambient temperature, the resulting solid was collected by vacuum filtration, washed with 1,4-dioxane (3×25 mL) and MeOH (3×25 mL), and dried in vacuo to afford compound E3 (0.801 g, 70%) as a yellow solid: $^1$H NMR (300 MHz, DMSO-$d_6$) δ 12.22 (s, 1H), 10.01 (s, 1H), 8.58 (s, 1H), 7.82-7.76 (m, 4H), 7.46 (s, 2H); ESI MS m/z 314 [M–H]$^-$.

Step Three.

N-(4-(1H-Tetrazol-1-yl)phenyl)-6-hydroxy-2,4-dioxo-1,2,3,4-tetrahydropyrimidine-5-carboxamide (E4, Formula IIc): A suspension of compound E3 (0.400 g, 1.04 mmol) in 1 M hydrogen chloride in methanol (8 mL) was stirred at ambient temperature for 4 h. After this time, the mixture was filtered, the filter cake washed with methanol (3×15 mL) and water (3×15 mL), and dried under high vacuum at 45° C. to afford compound E4 (0.215 g, 65%) as a light yellow solid: $^1$H NMR (300 MHz, DMSO-$d_6$) δ 12.20-11.20 (br s, 2H), 11.67 (s, 1H), 10.09 (s, 1H), 7.93 (d, J=8.9 Hz, 2H), 7.81 (d, J=9.0 Hz, 2H); APCI MS, m/z 314 [M–H]$^-$.

Figure 8:
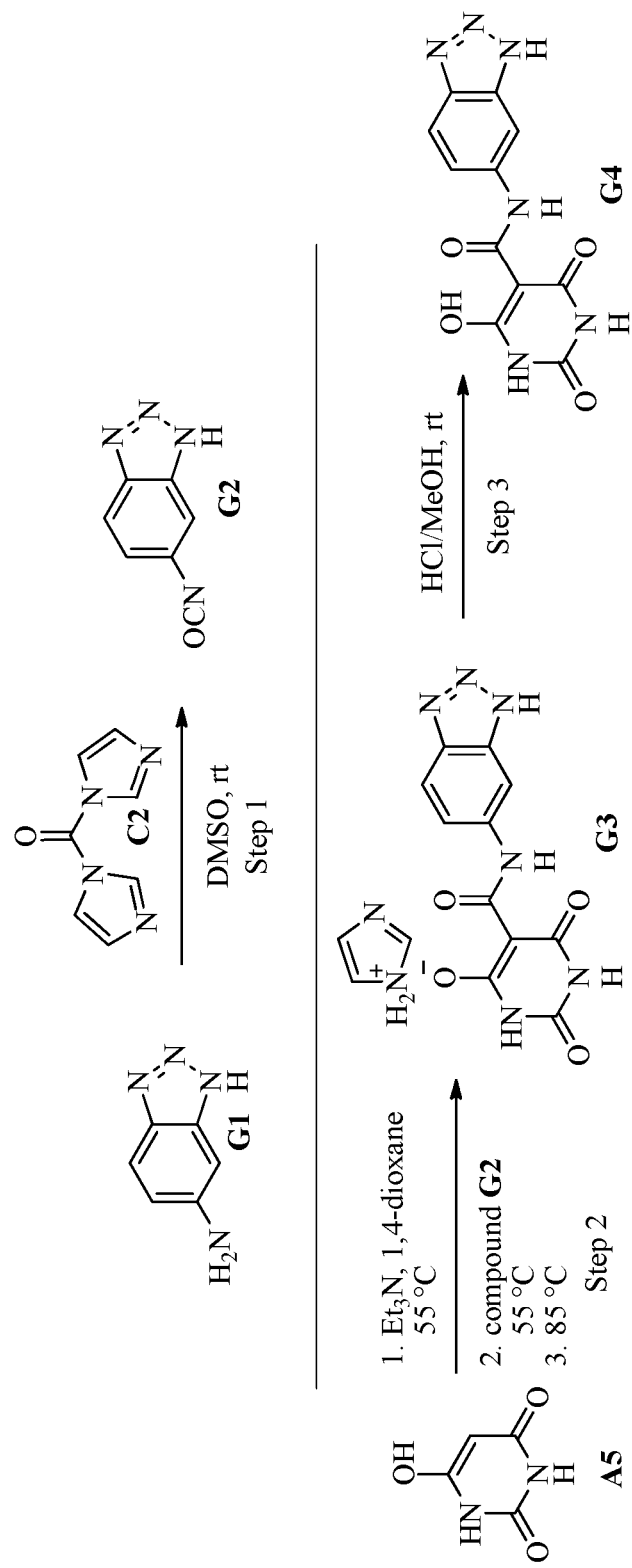
FIG. 8 illustrates an exemplary synthesis scheme for preparation of a compound having a structure represented by Formula (III$_a$).

Example 4: Preparation of N-(1H-benzo[d][1,2,3]triazol-6-yl)-6-hydroxy-2,4-dioxo-1,2,3,4-tetrahydropyrimidine-5-carboxamide (G4, Formula (IIIa), with Reference to the Synthesis Scheme Illustrated in FIG. 8)

Steps One & Two.

N-(1H-Benzo[d][1,2,3]triazol-6-yl)-6-hydroxy-2,4-dioxo-1,2,3,4-tetrahydropyrimidine-5-carboxamide Imidazole Salt (G3): To a solution of compound C2 (1.78 g, 11.0 mmol) in anhydrous DMSO (5 mL) was added compound G1 (1.34 g, 10.0 mmol) at ambient temperature under nitrogen. The reaction mixture was then stirred for 1 h to provide a solution of compound G2 in DMSO which was used directly in the subsequent step.

In a separate flask, to a suspension of barbituric acid A5 (1.28 g, 10.0 mmol) in anhydrous 1,4-dioxane (35 mL) was added triethylamine (1.01 g, 10.0 mmol) at 55° C. under nitrogen. After addition, the mixture was stirred for 20 min. Then, to this mixture was added the compound G2 solution in DMSO dropwise over 30 min. The resulting mixture was heated to 85° C. for 3 h. After this time, the hot reaction mixture was filtered. The filter cake was washed with 1,4-dioxane (4×25 mL) and MeOH (3×20 mL) and dried in vacuo to afford compound G3 (2.31 g, 65%) as a tan solid: $^1$H NMR (300 MHz, DMSO-$d_6$) δ 12.25 (s, 1H), 8.69 (s, 1H), 8.42 (s, 1H), 7.86 (d, J=8.9 Hz, 1H), 7.52 (s, 2H), 7.17 (dd, J=8.9, 1.4 Hz, 1H); ESI MS m/z 287 [M–H]$^-$.

Step Three.

N-(1H-Benzo[d][1,2,3]triazol-6-yl)-6-hydroxy-2,4-dioxo-1,2,3,4-tetrahydropyrimidine-5-carboxamide (G4): A suspension of compound G3 (0.779 g, 2.19 mmol) in 1 M hydrogen chloride in methanol (10 mL) was stirred at ambient temperature for 4 h. After this time, the mixture was filtered, the filter cake washed with methanol (4×20 mL) and water (2×20 mL), and dried under high vacuum at 45° C. to afford compound G4 (0.422 g, 86%) as an off-white solid: $^1$H NMR (300 MHz, DMSO-$d_6$) δ 12.50-11.10 (br s, 2H), 11.71 (s, 1H), 8.20 (s, 1H), 7.97 (d, J=8.6 Hz, 1H), 7.41 (d, J=8.6 Hz, 1H); APCI MS, m/z 287 [M–H]$^-$.

Figure 9:
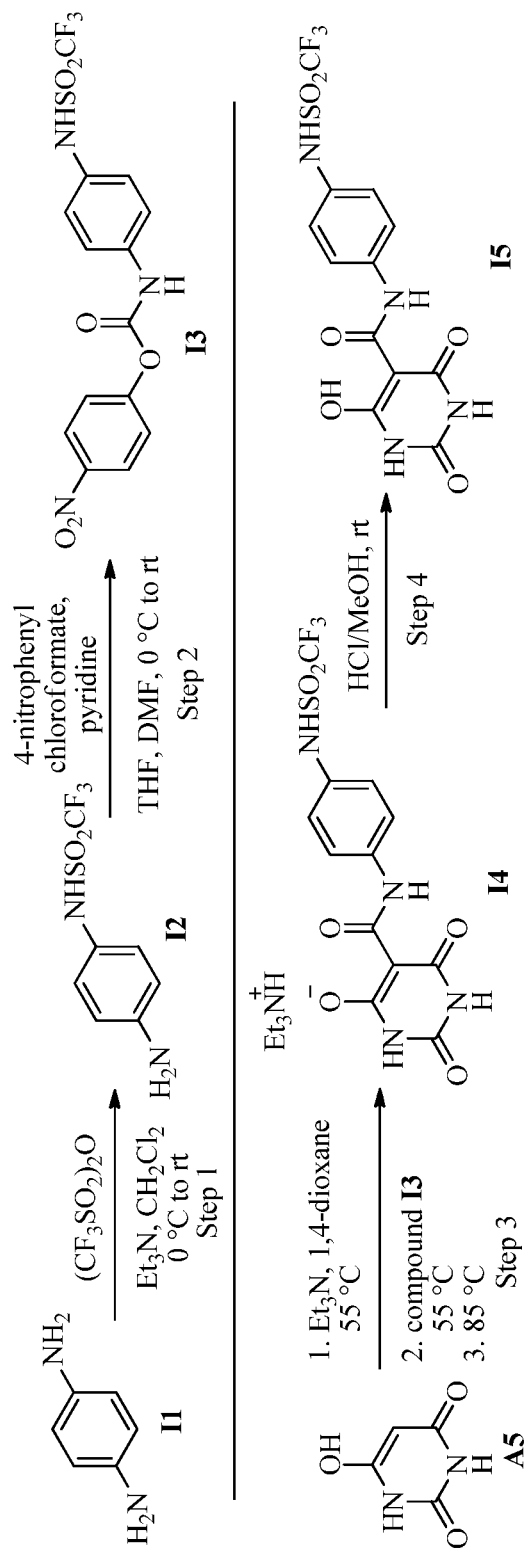
FIG. 9 illustrates an exemplary synthesis scheme for preparation of a compound having a structure represented by Formula (I$_c$).

Example 5: Preparation of 6-hydroxy-2,4-dioxo-N-(4-(trifluoromethylsulfonamido)phenyl)-1,2,3,4-tetrahydropyrimidine-5-carboxamide (I5, Formula Ic, with Reference to the Synthesis Scheme Illustrated in FIG. 9)

Step One.

N-(4-Aminophenyl)-1,1,1-trifluoromethanesulfonamide (I2): To a stirred solution of compound I1 (3.24 g, 30.0 mmol) and triethylamine (4.55 g, 45.0 mmol) in anhydrous dichloromethane (350 mL) was added a solution of $(CF_3SO_2)_2O$ (8.46 g, 30.0 mmol) in anhydrous dichloromethane (50 mL) dropwise over 1.5 h at 0° C. under nitrogen. After the addition was completed, the reaction was warmed to ambient temperature and stirred for 18 h. After this time, the reaction mixture was diluted with dichloromethane (300 mL), washed with saturated $NaHCO_3$ aqueous solution (300 mL), dried over anhydrous $Na_2SO_4$, filtered, and concentrated under reduced pressure. The residue was purified by flash column chromatography on silica gel eluting with 0% to 10% MeOH/$CH_2Cl_2$ to provide compound 12 (2.35 g, 47%) as a yellow solid: APCI MS, m/z 241 [M+H]$^+$.

Step Two.

4-Nitrophenyl (4-(Trifluoromethylsulfonamido)phenyl)carbamate (I3): To a stirred solution of 4-nitrophenyl chloroformate (2.12 g, 10.5 mmol) in anhydrous THF (30 mL) was added a solution of compound 12 (2.40 g, 9.99 mmol) and pyridine (1.19 g, 15.0 mmol) in anhydrous THF (20 mL) and anhydrous DMF (15 mL) dropwise over 10 min at 0° C. under nitrogen. After the addition was completed, the reaction was slowly warmed to ambient temperature over 3 h and stirred at ambient temperature for 18 h. After this time, the reaction mixture was diluted with EtOAc (150 mL), washed with brine (150 mL), dried over anhydrous $Na_2SO_4$, filtered, and concentrated under reduced pressure. The residue was purified by flash column chromatography on silica gel eluting with 10% to 50% EtOAc/hexanes to afford compound 13 (2.35 g, 52%) as a yellow solid: APCI MS, m/z 404 [M–H]$^-$.

Step Three.

6-Hydroxy-2,4-dioxo-N-(4-(trifluoromethylsulfonamido)phenyl)-1,2,3,4-tetrahydropyrimidine-5-carboxamide Triethylamine Salt (I4): To a stirred suspension of barbituric acid A5 (0.590 g, 4.57 mmol) in anhydrous 1,4-dioxane (10 mL) was added triethylamine (0.460 g, 4.57 mmol) at 55° C. under nitrogen. After stirring at 55° C. for 20 min, a solution of compound 13 (1.85 g, 4.57 mmol) in anhydrous 1,4-dioxane (10 mL) was added dropwise over 10 min. After the addition was completed, the mixture was heated at 85° C. for 2 h. After this time, the hot mixture was filtered, the filter cake washed with 1,4-dioxane (2×10 mL), and dried under high vacuum to afford compound 14 (1.58 g, 70%) as a white solid: $^1$H NMR (300 MHz, DMSO-$d_6$) δ 11.44 (s, 1H), 11.35-10.80 (br s, 2H), 9.20-8.80 (br s, 1H), 7.23 (d, J=8.8 Hz, 2H), 6.96 (d, J=8.8 Hz, 2H), 3.09 (q, J=7.3 Hz, 6H), 1.17 (t, J=7.3 Hz, 9H); APCI MS, m/z 393 [M–H]$^-$.

Step Four.

6-Hydroxy-2,4-dioxo-N-(4-(trifluoromethylsulfonamido)phenyl)-1,2,3,4-tetrahydropyrimidine-5-carboxamide (I5, Formula Ic): A suspension of compound 14 (0.800 g, 0.436 mmol) in 1.25 M hydrogen chloride in methanol (10 mL) was stirred at ambient temperature for 3 h. After this time, the reaction mixture was filtered, the filter cake washed with methanol (3×10 mL) and water (3×10 mL), and dried under high vacuum at 45° C. to afford compound 15 (0.203 g, 32%) as a white solid: $^1$H NMR (300 MHz, DMSO-$d_6$) δ 12.50-11.60 (br s, 3H), 11.52 (s, 1H), 7.58 (d, J=8.7 Hz, 2H), 7.28 (d, J=8.7 Hz, 2H); ESI MS, m/z 393 [M–H]$^-$.

Figure 10:
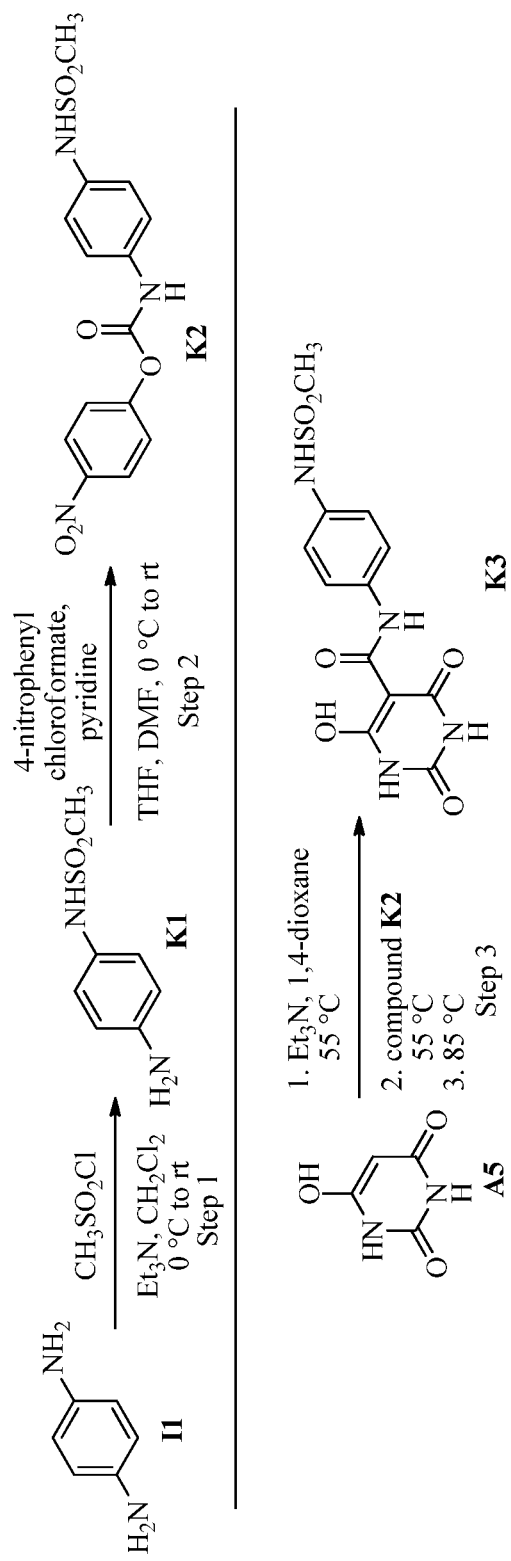
FIG. 10 illustrates an exemplary synthesis scheme for preparation of a compound having a structure represented by Formula (I$_b$).

Example 6: Preparation of 6-hydroxy-N-(4-(methylsulfonamido)phenyl)-2,4-dioxo-1,2,3,4-tetrahydropyrimidine-5-carboxamide (K3, Formula (Ib), with Reference to the Synthesis Scheme Illustrated in FIG. 10)

Step One.

N-(4-Aminophenyl)methanesulfonamide (K1). To a stirred solution of compound I1 (3.24 g, 30.0 mmol) and triethylamine (4.55 g, 45.0 mmol) in anhydrous dichloromethane (300 mL) was added a solution of $CH_3SO_2Cl$ (3.44 g, 30.0 mmol) in anhydrous dichloromethane (50 mL) dropwise over 1.5 h at 0° C. under nitrogen. After the addition was completed, the reaction mixture was warmed to ambient temperature and stirred for 18 h. After this time, the reaction mixture was diluted with dichloromethane (100 mL), washed with saturated $NaHCO_3$ aqueous solution (200 mL), dried over anhydrous $Na_2SO_4$, filtered, and concentrated under reduced pressure. The residue was purified by flash column chromatography on silica gel eluting with 0% to 10% $MeOH/CH_2Cl_2$ to provide compound K1 (3.90 g, 70%) as a yellow solid: APCI MS, m/z 187 $[M+H]^+$.

Steps Two & Three.

6-Hydroxy-N-(4-(methylsulfonamido)phenyl)-2,4-dioxo-1,2,3,4-tetrahydropyrimidine-5-carboxamide (K3, Formula Ib): To a stirred solution of 4-nitrophenyl chloroformate (2.02 g, 10.0 mmol) in anhydrous THF (40 mL) was added a solution of compound K1 (1.86 g, 10.0 mmol) and pyridine (1.03 g, 13.0 mmol) in anhydrous THF (15 mL) and anhydrous DMF (15 mL) dropwise over 15 min at 0° C. under nitrogen. After the addition was completed, the reaction was slowly warmed to ambient temperature over 2 h and stirred at ambient temperature for 18 h to provide a solution of compound K2 in THF and DMF which was used directly in the subsequent step.

In a separate flask, to a suspension of barbituric acid A5 (1.29 g, 10.1 mmol) in anhydrous 1,4-dioxane (20 mL) was added triethylamine (2.53 g, 25.0 mmol) at 55° C. under nitrogen. After the addition was completed, the mixture was stirred for 10 min. Then, to this mixture was added the compound K2 solution in THF and DMF dropwise over 25 min. The resulting mixture was heated to 85° C. for 4.5 h. After cooling to ambient temperature, 0.1 N hydrochloric acid (500 mL) was added. The mixture was stirred for 20 min and filtered. The filter cake was washed with water (2×50 mL) and dried under high vacuum at 50° C. to afford compound K3 (2.12 g, 62%) as a light green solid: $^1H$ NMR (300 MHz, DMSO-$d_6$) δ 12.30-11.60 (br s, 2H), 11.46 (s, 1H), 9.78 (s, 1H), 7.50 (d, J=8.7 Hz, 2H), 7.23 (d, J=8.7 Hz, 2H), 2.99 (s, 3H); APCI MS, m/z 339 $[M-H]^-$.

Figure 11:
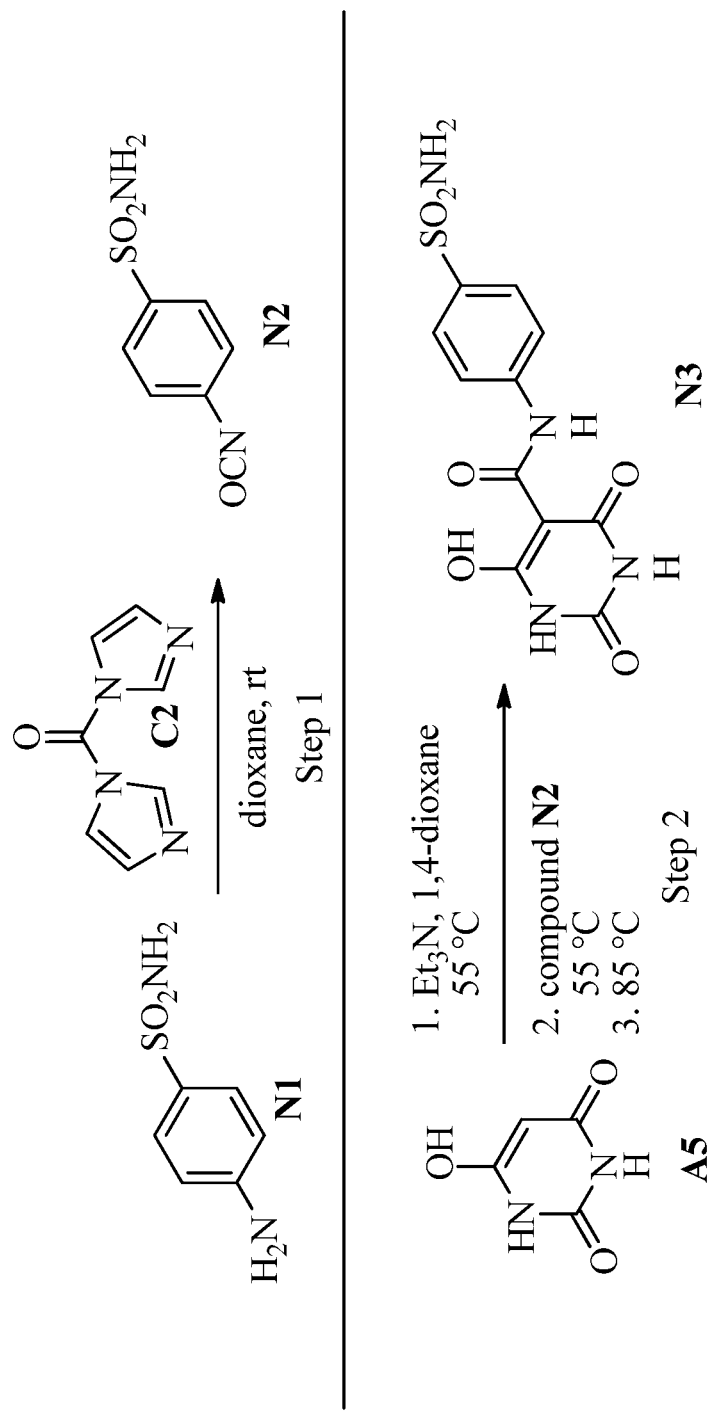
FIG. 11 illustrates an exemplary synthesis scheme for preparation of a compound having a structure represented by Formula (I$_a$).

Example 7: Preparation of 6-hydroxy-2,4-dioxo-N-(4-sulfamoylphenyl)-1,2,3,4-tetrahydropyrimidine-5-carboxamide (N3, Formula Ia, with Reference to the Synthesis Scheme Illustrated in FIG. 11)

Steps One & Two.

6-Hydroxy-2,4-dioxo-N-(4-sulfamoylphenyl)-1,2,3,4-tetrahydropyrimidine-5-carboxamide (N3, Formula Ia): To a solution of compound C2 (1.62 g, 10.0 mmol) in anhydrous 1,4-dioxane (30 mL) was added a solution of compound N1 (1.72 g, 10.0 mmol) in anhydrous 1,4-dioxane (30 mL) dropwise over 10 min at ambient temperature under nitrogen. The reaction mixture was then stirred for 2.5 h to provide a solution of compound N2 in 1,4-dioxane which was used directly in the subsequent step.

In a separate flask, to a suspension of barbituric acid A5 (1.28 g, 10.0 mmol) in anhydrous 1,4-dioxane (30 mL) was added triethylamine (1.02 g, 10.0 mmol) at 55° C. under nitrogen. After the addition was completed, the mixture was stirred for 15 min. Then, to this mixture was added the compound N2 solution in 1,4-dioxane dropwise over 30 min. The resulting mixture was heated to 85° C. for 4.5 h. After this time, the reaction mixture was cooled to ambient temperature, diluted with 0.1 N hydrochloric acid (500 mL), and filtered. The filter cake was mixed with 1,4-dioxane (150 mL) and heated to reflux for 1 h. The hot suspension was filtered. The filtrate was cooled to ambient temperature and the precipitate collected by vacuum filtration and dried under high vacuum at 45° C. to afford compound N3 (0.435 g, 13%) as an off-white solid: $^1H$ NMR (300 MHz, DMSO-$d_6$) δ 12.20-11.60 (br s, 2H), 11.70 (s, 1H), 7.83 (d, J=8.7 Hz, 2H), 7.73 (d, J=8.7 Hz, 2H), 7.36 (s, 2H); APCI MS, m/z 325 $[M-H]^-$.

Example 8: Preparation of 6-hydroxy-N-(4-hydroxy-3-(hydroxymethyl)phenyl)-2,4-dioxo-1,2,3,4-tetrahydropyrimidine-5-carboxamide (D5, Formula Id, with Reference to the Synthesis Scheme Illustrated in FIG. 12)

Step One.

2-(Hydroxymethyl)-4-nitrophenol (D2): To a borane THF complex solution (1 M, 10.9 mL, 10.9 mmol) was added a solution of compound D1 (1.00 g, 5.46 mmol) in anhydrous THF (50 mL) dropwise over 5 min at 0° C. under nitrogen. After the addition was completed, the reaction mixture was warmed to ambient temperature and stirred for 18 h. After this time, the reaction was quenched by slow addition of 1 N hydrochloric acid (25 mL) at 0° C. The resulting mixture was stirred at ambient temperature for 2 h and then extracted with tert-butylmethyl ether (3×50 mL). The combined extracts were dried over anhydrous $Na_2SO_4$, filtered, and concentrated under reduced pressure to afford compound D2 (0.923 g, quant.) as a yellow solid: $^1H$ NMR (300 MHz, DMSO-$d_6$) δ 11.14 (s, 1H), 8.21 (d, J=2.9 Hz, 1H), 8.03 (dd, J=8.9, 3.0 Hz, 1H), 6.94 (d, J=8.9 Hz, 1H), 5.36 (br s, 1H), 4.51 (s, 2H).

Step 2:

4-Amino-2-(hydroxymethyl)phenol (D3): A suspension of compound D2 (0.494 g, 2.92 mmol) and 10% palladium on carbon (50% wet, 0.200 g) in ethanol (20 mL) was stirred under 1 atm of hydrogen for 4 h at ambient temperature. After this time, the reaction mixture was filtered through a short pad of Celite. The filtrate was concentrated under reduced pressure. The resulting residue was purified by flash column chromatograph on silica gel eluting with 0% to 10% $MeOH/CH_2Cl_2$ to afford compound D3 (0.256 g, 63%) as an off-white solid: $^1H$ NMR (300 MHz, DMSO-$d_6$) δ 8.22 (s, 1H), 6.58 (d, J=2.8 Hz, 1H), 8.03 (d, J=8.3 Hz, 1H), 6.27 (dd, J=8.3, 2.8 Hz, 1H), 4.81 (t, J=5.7 Hz, 1H), 4.37 (d, J=5.7 Hz, 2H), 4.36 (br s, 2H).

Steps Three & Four.

6-Hydroxy-N-(4-hydroxy-3-(hydroxymethyl)phenyl)-2,4-dioxo-1,2,3,4-tetrahydropyrimidine-5-carboxamide (D5, Formula Id): To a solution of compound C2 (0.175 g, 1.08 mmol) in anhydrous DMSO (4 mL) was added compound D3 (0.100 g, 0.719 mmol) at ambient temperature under nitrogen. The reaction mixture was then stirred for 40 min to provide a solution of compound D4 in DMSO which was used directly in the subsequent step.

In a separate flask, to a suspension of barbituric acid A5 (0.092 g, 0.719 mmol) in anhydrous 1,4-dioxane (2 mL) was added triethylamine (0.073 g, 0.719 mmol) at 55° C. under nitrogen. After the addition was completed, the mixture was stirred for 5 min. Then, to this mixture was added the compound D4 solution in DMSO. The resulting mixture was heated to 85° C. for 2 h. After cooling to ambient temperature, 0.5 N hydrochloric acid (8 mL) was added slowly. The mixture was stirred for 1 h and filtered. The filter cake was washed with water (2×10 mL) and dried in vacuo to afford a crude product (0.107 g) which was further purified by C-18 reverse phase column chromatography eluting with 0% to 60% acetonitrile/water to afford compound D5 (0.038 g, 18%) as an off-white solid: $^1$H NMR (300 MHz, DMSO-$d_6$) δ 11.50 (br s, 2H), 11.39 (s, 1H), 9.54 (s, 1H), 7.39 (d, J=2.5 Hz, 1H), 7.22 (dd, J=8.6, 2.7 Hz, 1H), 6.78 (d, J=8.6 Hz, 1H), 5.09 (s, 1H), 4.47 (s, 2H); ESI MS m/z 292 [M–H]$^-$.

Figure 13:
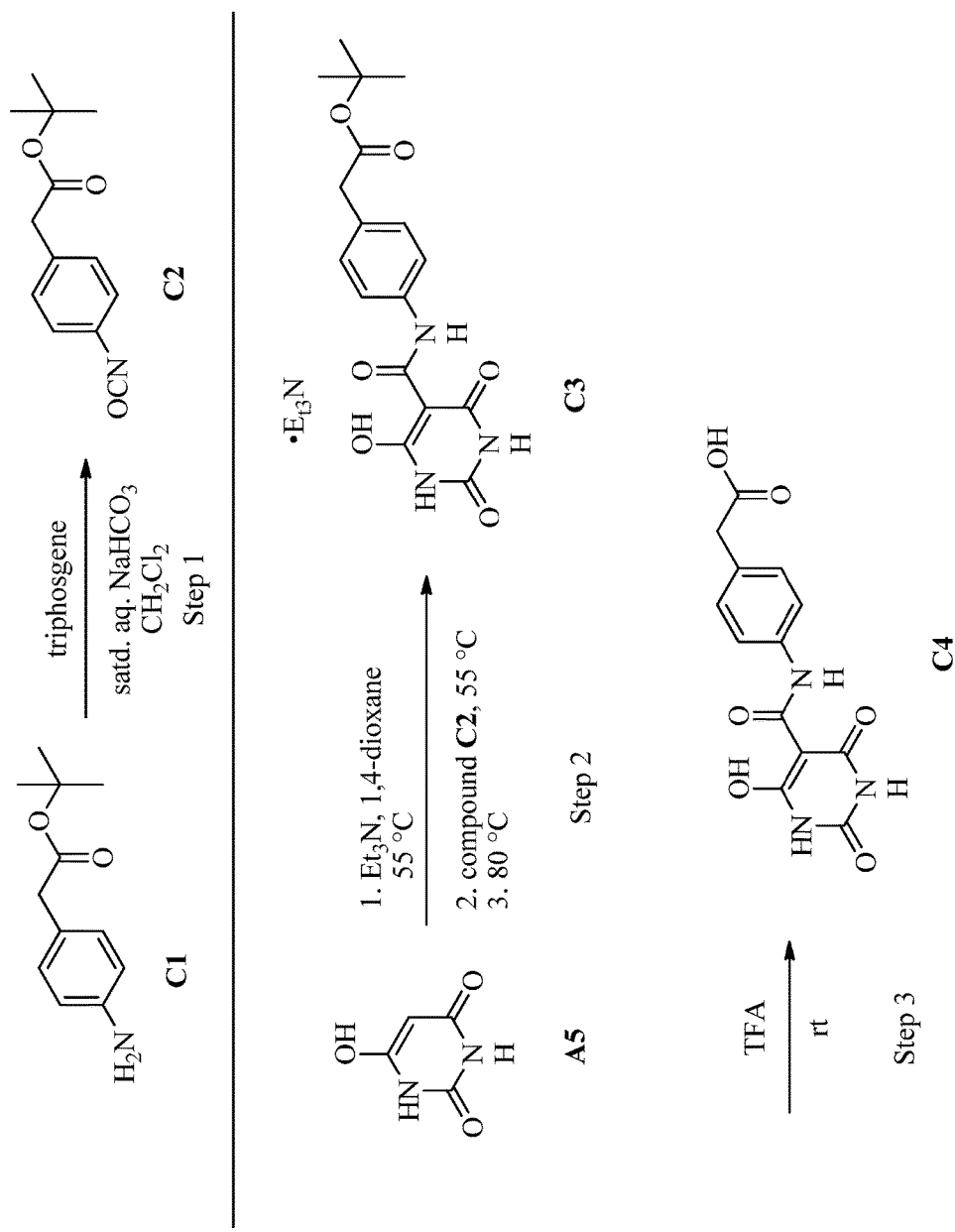
FIG. 13 illustrates an exemplary synthesis scheme for preparation of a compound having a structure represented by Formula (I$_e$).

Example 9: Preparation of 2-(4-(6-hydroxy-2,4-dioxo-1,2,3,4-tetrahydropyrimidine-5-carboxamido)phenyl)acetic acid (shown as C4 in FIG. 13, Formula Ie, with Reference to the Synthesis Scheme Illustrated in FIG. 13). The Step One.
tert-Butyl 2-(4-isocyanatophenyl)acetate (C2). To an ice cold solution of C1 (700 mg, 3.38 mmol) in anhydrous methylene chloride (30 mL) and satd. aq. sodium bicarbonate (30 mL), under a nitrogen atmosphere, was added a solution of triphosgene (401 mg, 1.35 mmol) in anhydrous methylene chloride (5 mL) directly to the methylene chloride layer. After the addition was completed, stirring was resumed at 0° C. for 1 h. After this time, the organic layer was concentrated under reduced pressure to afford compound C2 (859 mg, quantitative) as a brown oil: $^1$H NMR (500 MHz, CDCl$_3$) δ 7.23-7.20 (m, 2H), 7.05-7.02 (m, 2H), 3.49 (s, 2H), 1.43 (s, 9H).

Step Two.
tert-Butyl 2-(4-(6-hydroxy-2,4-dioxo-1,2,3,4-tetrahydropyrimidine-5-carboxamido)phenyl)acetate triethylamine salt (C3). To a suspension of barbituric acid A5 (423 mg, 3.30 mmol) in anhydrous 1,4-dioxane (8 mL), at 55° C. and under a nitrogen atmosphere, was added triethylamine (0.46 mL, 3.3 mmol). After 30 min, a solution of compound C2 (770 mg, 3.30 mmol) in anhydrous 1,4-dioxane (5 mL) was added dropwise over 15 min. The resulting mixture was heated to 80° C. for 3 h. The solid was collected by vacuum filtration from the hot reaction mixture, rinsed with 1,4-dioxane (10 mL), methanol (1 mL), acetonitrile (5 mL) and dried to afford compound C3 (425 mg, 30%) as an off-white solid: $^1$H NMR (500 MHz, DMSO-$d_6$) δ 11.94 (s, 1H), 9.55 (br s, 2H), 7.44 (dd, J=6.5, 1.5 Hz, 2H), 7.08 (d, J=8.5 Hz, 2H), 3.07-3.05 (m, 6H), 1.39 (s, 9H), 1.16 (t, J=7.5 Hz, 9H).

Step Three.
2-(4-(6-Hydroxy-2,4-dioxo-1,2,3,4-tetrahydropyrimidine-5-carboxamido)phenyl)acetic acid (C4, RLBN1040, Formula Ie). A suspension of compound C3 (425 mg, 1.18 mmol) in TFA (5 mL) was stirred at ambient temperature for 2 h. After this time, to the white slurry was added acetonitrile (5 mL) and the solid was collected by vacuum filtration. The filter cake was washed with water (10 mL) and acetonitrile (10 mL). The solid was dried under high vacuum at 50° C. to afford compound C4 (257 mg, 71%) as a white solid: $^1$H NMR (300 MHz, DMSO-$d_6$) δ 12.32 (br s, 1H), 12.00 (br s, 1H), 11.50 (s, 1H), 11.35 (br s, 1H), 7.46 (dd, J=6.5, 2.0 Hz, 2H), 7.28 (d, J=8.5 Hz, 2H), 3.57 (s, 2H); ESI MS, m/z 304 [M–H]$^-$.

Figure 14:
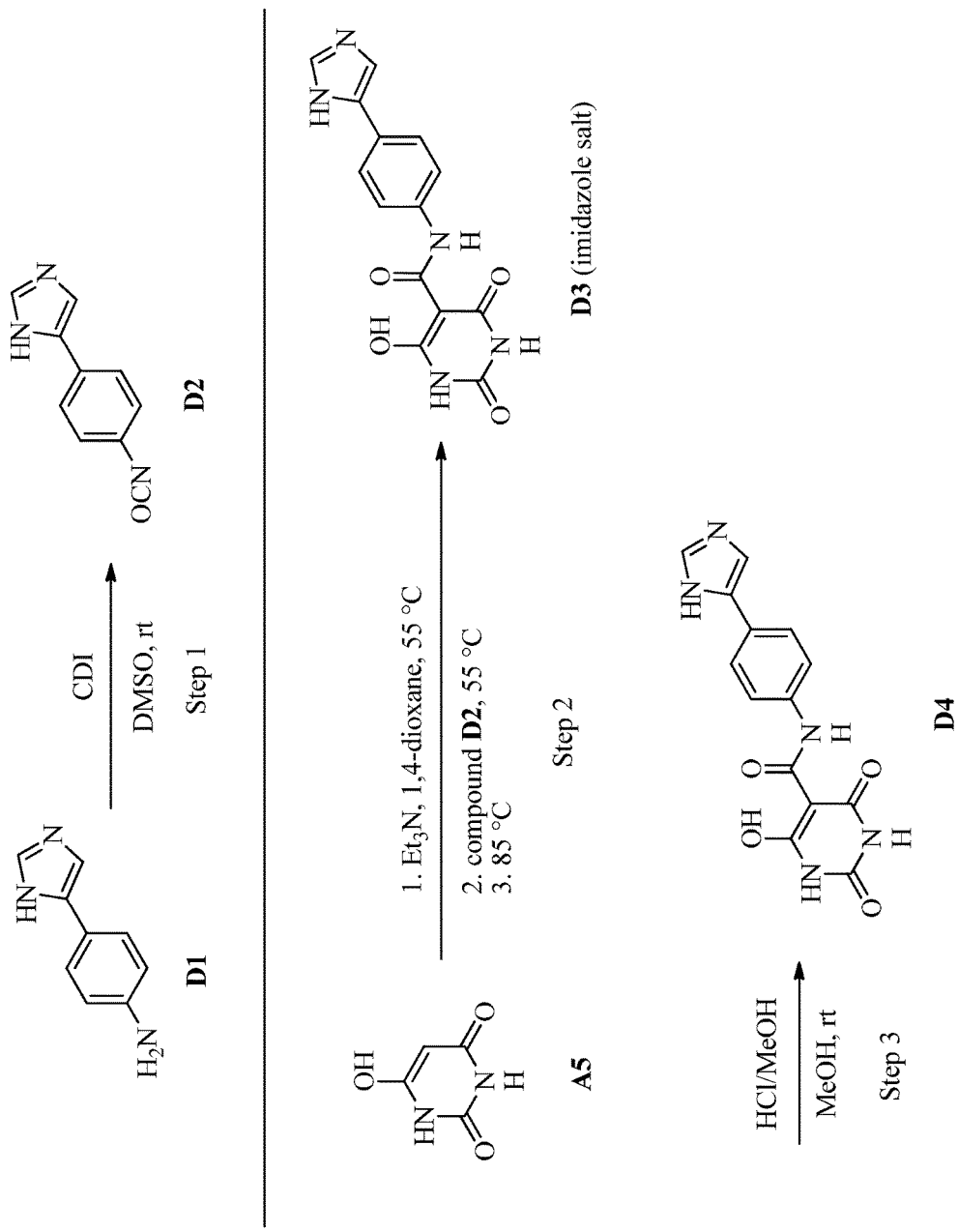
FIG. 14 illustrates an exemplary synthesis scheme for preparation of a compound having a structure represented by Formula (II$_d$).

Example 10: Preparation of N-(4-(1H-imidazol-5-yl)phenyl)-6-hydroxy-2,4-dioxo-1,2,3,4-tetrahydropyrimidine-5-carboxamide (shown as D4 in FIG. 14, Formula IId, with Reference to the Synthesis Scheme Illustrated in FIG. 14)

Steps One and Two.
N-(4-(1H-Imidazol-5-yl)phenyl)-6-hydroxy-2,4-dioxo-1,2,3,4-tetrahydropyrimidine-5-carboxamide imidazole salt (D3). To a stirred solution of compound D1 (515 mg, 3.24 mmol) in anhydrous DMSO (3 mL), at 0-5° C. and under a nitrogen atmosphere, was added 1,1'-carbonyldiimidazole (162 mg, 3.56 mmol) in one portion. The reaction mixture was then stirred at ambient temperature for 1.25 h to provide a solution of compound D2 in DMSO which was used directly in the subsequent step.

In a separate flask, to a suspension of barbituric acid A5 (415 mg, 3.24 mmol) in anhydrous 1,4-dioxane (10 mL), at 55° C. under nitrogen, was added triethylamine (0.44 mL, 3.24 mmol). After 25 min. compound D2, as a solution in DMSO, was added dropwise over 0.5 h. The reaction mixture was heated to 80° C. for 3 h. The resulting solid was collected while still hot by vacuum filtration. The filter cake was washed with warm 1,4-dioxane (4×25 mL), methanol (3×20 mL) and dried in vacuo to afford a crude D3 (681 mg, 56%) as a tan/pink solid, which was used in the next step without further purification: ESI MS m/z 312 [M–H]$^-$.

Step Three.
N-(4-(1H-imidazol-5-yl)phenyl)-6-hydroxy-2,4-dioxo-1,2,3,4-tetrahydropyrimidine-5-carboxamide (D4, RLBN1041, Formula IId). A suspension of compound D3 (400 mg, 1.05 mmol) in N,N-dimethylformamide (4 mL) was heated to 95° C. for 1 h. After this time, the reaction mixture was filtered and the filter cake was washed with warm N,N-dimethylformamide (2×5 mL), methanol (2×10 mL), water (3×5 mL) and dried under vacuum. The solid was suspended in 0.25 N HCl (100 mL) and heated to 90° C. for 2 h. After this time, the reaction mixture was filtered while still warm and washed with water (2×15 mL). The solid was dried under high vacuum at 50° C. to afford compound D4 (136 mg, 41%) as an off-white solid: $^1$H NMR (300 MHz, TFA-d) δ 8.81 (s, 1H), 7.82-7.74 (m, 4H), 7.71 (s, 1H); ESI MS, m/z 314 [M+H]$^+$.

Figure 15:
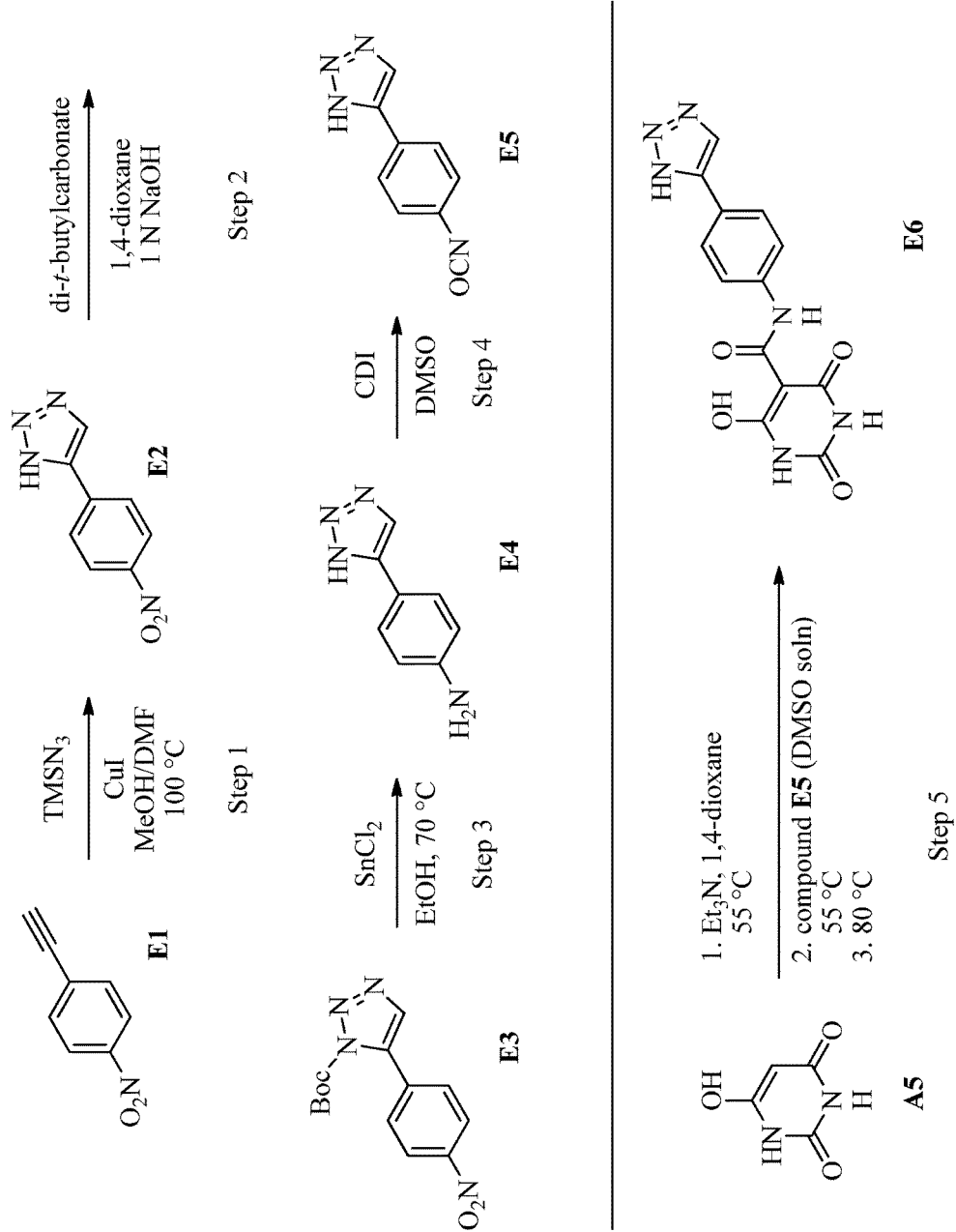
FIG. 15 illustrates an exemplary synthesis scheme for preparation of a compound having a structure represented by Formula (II$_e$).

Example 11: Preparation of N-(4-(1H-1,2,3-triazol-5-yl)phenyl)-6-hydroxy-2,4-dioxo-1,2,3,4-tetrahydropyrimidine-5-carboxamide (shown as E6 in FIG. 15, Formula IIe, with Reference to the Synthesis Scheme Illustrated in FIG. 15)

Step One.
5-(4-Nitrophenyl)-1H-1,2,3-triazole (E2). To a stirred solution of E1 (1.00 g, 6.80 mmol) in N,N-dimethylformamide/methanol (9:1, 14 mL), under an argon atmosphere, was added copper(I) iodide (650 mg, 3.41 mmol) and trimethylsilyl azide (1.4 mL, 10 mmol). The yellow suspension was heated to 100° C. for 3.5 h. After this time, the reaction mixture was cooled to ambient temperature and concentrated under reduced pressure. The residue was triturated with ethyl acetate and the solid was collected by vacuum filtration. The residue was purified by flash column chromatography on silica gel eluting with 5-50% ethyl acetate/hexanes to afford compound E2 (900 mg, 70%) as a pale yellow solid: $^1$H NMR (500 MHz, DMSO-$d_6$) δ 15.45 (br s, 1H), 8.65 (br s, 1H), 8.34-8.31 (m, 2H), 8.17-8.14 (m, 2H).

Step Two.
tert-Butyl 5-(4-Nitrophenyl)-1H-1,2,3-triazole-1-carboxylate (E3). To a stirred solution of compound E2 (490 mg, 2.58 mmol), in 1,4-dioxane (5 mL) and 1 N NaOH (2 mL) was added di-tert-butyl dicarbonate (619 mg, 2.84 mmol). After stirring overnight, the reaction mixture was brought to pH=6 with 2 N HCl and extracted with ethyl acetate. The organic layer was washed with water, brine, dried over anhydrous Na$_2$SO$_4$, filtered, and concentrated under reduced pressure to afford E3 (657 mg, 88%) as a pale yellow solid: $^1$H NMR (500 MHz, DMSO-d$_6$) δ 8.86 (s, 1H), 8.40-8.33 (m, 2H), 8.30-8.23 (m, 2H), 1.65 (s, 9H).

Step Three.

4-(1I-1,2,3-Triazol-5-yl)aniline (E4). A suspension of E4 (655 mg, 2.26 mmol) in ethanol (60 mL) was heated to 70° C. To the resulting golden solution was added tin(II) chloride (1.70 g, 9.03 mmol). The reaction mixture was stirred at 70° C. for 1 h. After this time, the reaction mixture was cooled to ambient temperature and concentrated under reduced pressure. The residue was diluted with ethyl acetate (75 mL) and poured into 5% aq NaHCO$_3$. A gummy solid formed and was removed by filtration. The organic layer was separated and concentrated under reduced pressure. The residue was purified by flash column chromatography on silica gel eluting with 5-20% methanol/methylene chloride to afford compound E4 (234 mg, 40%) as a yellow solid: $^1$H NMR (500 MHz, CD$_3$OD) δ 7.92 (br s, 1H), 7.53 (br s, 2H), 6.76 (d, J=8.5 Hz, 2H).

Steps Four and Five.

N-(4-(1H-1,2,3-Triazol-5-yl)phenyl)-6-hydroxy-2,4-dioxo-1,2,3,4-tetrahydropyrimidine-5-carboxamide (E6, RLB N1042, Formula IIe). To a stirred solution of compound E4 (75 mg, 0.47 mmol) in anhydrous DMSO (0.5 mL), under a nitrogen atmosphere, was added 1,1'-carbonyldiimidazole (114 mg, 0.703 mmol) in one portion. The reaction mixture was then stirred at ambient temperature for 20 min to provide a solution of compound E5 in DMSO which was used directly in the subsequent step.

In a separate flask, to a suspension of barbituric acid A5 (60 mg, 0.47 mmol) in anhydrous 1,4-dioxane (1.5 mL), at 55° C. and under a nitrogen atmosphere, was added triethylamine (66 µL, 0.73 mmol). After the addition was complete the mixture was stirred for 15 min. Then, to this mixture was added the compound E5 solution in DMSO. The resulting mixture was heated to 80° C. for 0.5 h. After this time, the reaction mixture was cooled to 0° C. and 0.5 N HCl (4 mL) was added. The resulting solid was collected by vacuum filtration. The solid was triturated with methanol and collected again by vacuum filtration. The solid was then stirred in water (2 mL) and 1 N HCl (0.25 mL) at 50° C. for 0.5 h. After this time, the solid was collected, rinsed with water and acetonitrile. The solid was dried in vacuo at 50° C. to afford a E6 (74 mg, 50%) as an off-white solid: $^1$H NMR (500 MHz, TFA-d) δ 8.69 (s, 1H), 7.98-7.85 (m, 4H); ESI MS m/z 313 [M–H]$^-$.

Figure 16:
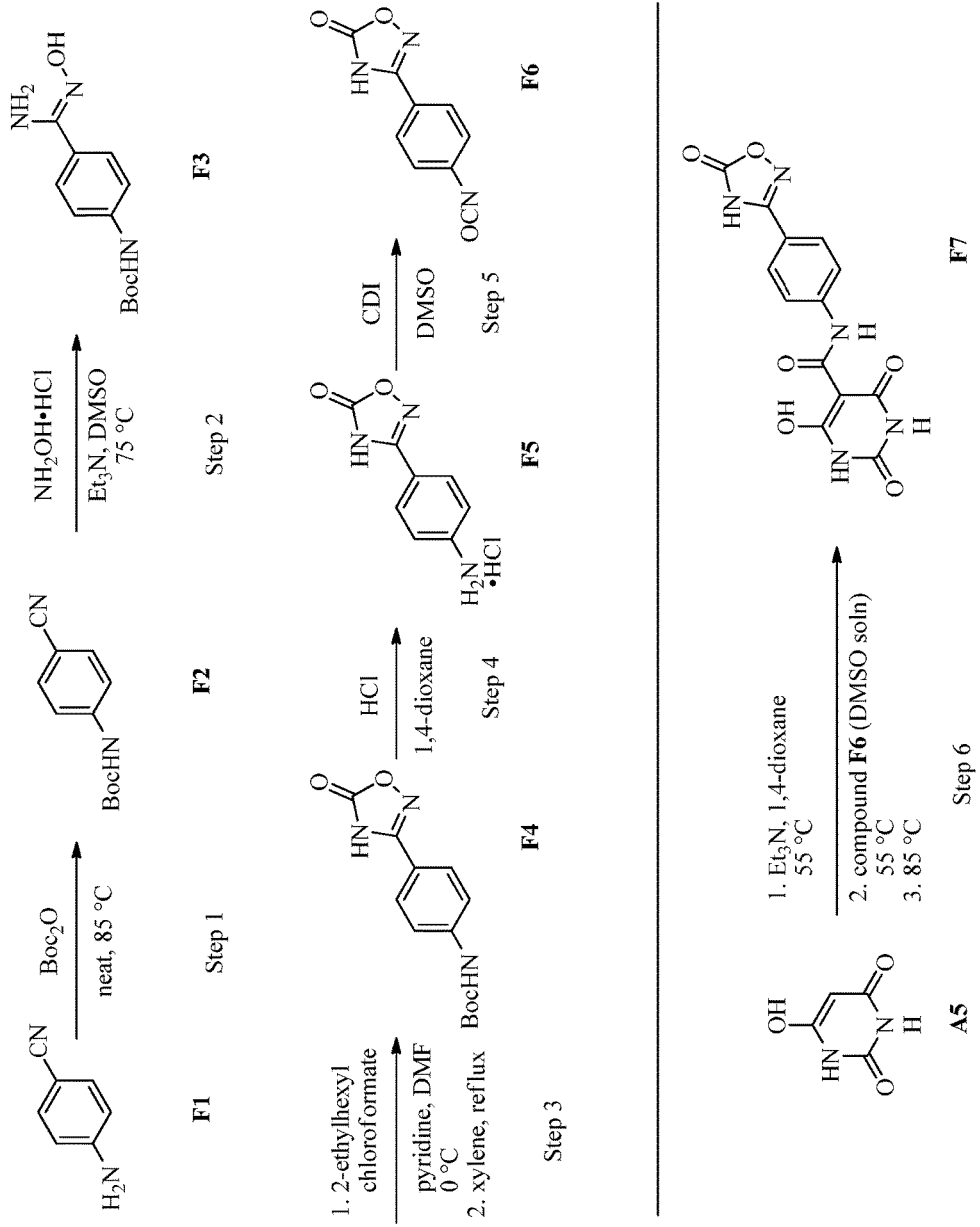
FIG. 16 illustrates an exemplary synthesis scheme for preparation of a compound having a structure represented by Formula (I$_f$).

Example 12: Preparation of 6-hydroxy-2,4-dioxo-N-(4-(5-oxo-4,5-dihydro-1,2,4-oxadiazol-3-yl)phenyl)-1,2,3,4-tetrahydropyrimidine-5-carboxamide (shown as F7 in FIG. 16, Formula if, with Reference to the Synthesis Scheme Illustrated in FIG. 16)

Step One.

tert-Butyl (4-cyanophenyl)carbamate (F2). To stirred di-tert-butyl dicarbonate (6.8 g, 31 mmol) at 40° C. was added compound F1 (3.5 g, 29 mmol). The reaction mixture was heated to 85° C. for 2.5 h. After this time, additional di-tert-butyl dicarbonate (950 mg, 4.3 mmol) was added and heating continued for 4 h. The material was purified by flash column chromatography on silica gel eluting with 0-25% ethyl acetate/hexanes to afford compound F2 (4.3 g, 68%) as a white solid: $^1$H NMR (500 MHz, DMSO-d$_6$) δ 9.87 (s, 1H), 7.72-7.69 (m, 2H), 7.64-7.61 (m, 2H), 1.49 (s, 9H).

Step Two.

tert-Butyl (4-(N'-hydroxycarbamimidoyl)phenyl)carbamate (F3). To a solution of hydroxylamine hydrochloride (6.90 g, 98.6 mmol) in DMSO (30 mL) was added triethylamine (13.7 mL, 98.6 mmol). The resulting solid was removed by filtration and rinsed with tetrahydrofuran. The filtrate was concentrated under reduced pressure to remove the tetrahydrofuran. To this was added F2 (4.30 g, 19.7 mmol) in DMSO (20 mL) and the solution was heated to 75° C., under a nitrogen atmosphere. After 3.5 h, the reaction mixture was cooled to ambient temperature and diluted with water (50 mL). The mixture was extracted with ethyl acetate (25 mL) and the organic layer was extracted with 1 N HCl (30 mL). The aqueous layer was basified with 1 N NaOH to pH=10 and extracted with ethyl acetate (2×50 mL). The combined organic extracts were washed with water (20 mL), brine (20 mL) dried over anhydrous Na$_2$SO$_4$, filtered, and concentrated under reduced pressure to afford compound F3 (3.5 g, 70%) as an off-white solid: $^1$H NMR (500 MHz, DMSO-d$_6$) δ 9.45 (s, 1H), 9.42 (s, 1H), 7.56-7.53 (m, 2H), 7.43 (d, J=8.5 Hz, 2H), 5.68 (s, 2H), 1.47 (s, 9H).

Step Three.

tert-Butyl (4-(5-oxo-4,5-dihydro-1,2,4-oxadiazol-3-yl)phenyl)carbamate (F4). A solution of F3 (1.0 g, 4.0 mmol) and pyridine (0.35 mL, 4.4 mmol) in N,N-dimethylformamide (8 mL), under a nitrogen atmosphere, was cooled in an ice/water bath. To this was added 2-ethylhexylchloroformate (0.78 mL, 4.0 mmol) dropwise. The reaction mixture was stirred at 0° C. for 40 min. After this time, the reaction mixture was quenched by the addition of water (20 mL). The mixture was extracted with ethyl acetate (30 mL). The organic layer was washed with brine (10 mL) dried over anhydrous Na$_2$SO$_4$, filtered, and concentrated under reduced pressure. To the residue was added xylenes (10 mL) and the mixture was heated to reflux. After 45 min the reaction mixture was cooled to ambient temperature. The resulting solid was collected by vacuum filtration, rinsed with methylene chloride and dried to provide compound F4 (688 mg, 62%) as an off-white solid: $^1$H NMR (500 MHz, DMSO-d$_6$) δ 12.78 (br s, 1H), 9.75 (s, 1H), 7.71-7.68 (m, 2H), 7.62 (d, J=8.5 Hz, 2H), 1.49 (s, 9H).

Step Four.

3-(4-Aminophenyl)-1,2,4-oxadiazol-5(4I)-one hydrochloride (F5). Compound F4 was taken up in 1 N HCl in methanol (15 mL) and 4 N HCl in 1,4-dioxane (15 mL) and heated to 50° C. After 0.5 h, the reaction mixture was cooled to ambient temperature and concentrated under reduced pressure. The residue was triturated with methylene chloride and the solid collected by vacuum filtration. The solid was dried in vacuo at 50° C. to give F5 (1.1 g, 84%) as a pale orange solid: $^1$H NMR (500 MHz, DMSO-d$_6$) δ 12.49 (s, 1H), 7.48-7.45 (m, 2H), 6.65 (d, J=8.5 Hz, 2H), 4.7 (br s, 2H).

Steps Five and Six.

6-Hydroxy-2,4-dioxo-N-(4-(5-oxo-4,5-dihydro-1,2,4-oxadiazol-3-yl)phenyl)-1,2,3,4-tetrahydropyrimidine-5-carboxamide (F7, RLBN1043, Formula If). To a stirred solution of 1,1'-carbonyldiimidazole (213 mg, 1.31 mmol) and imidazole (7.0 mg, 0.094 mmol) in DMSO (1 mL), under a nitrogen atmosphere, was added compound F5 (200 mg, 0.94 mmol) in anhydrous DMSO (1 mL) dropwise over 15 min. The reaction mixture was then stirred at ambient temperature for 10 min to provide a solution of compound F6 in DMSO which was used directly in the subsequent step.

In a separate flask, to a suspension of barbituric acid A5 (120 mg, 0.94 mmol) in anhydrous 1,4-dioxane (3 mL), at 55° C. and under a nitrogen atmosphere, was added triethylamine (0.13 mL, 0.94 mmol). After the addition was complete the mixture was stirred for 10 min. Then, to this mixture was added the compound F6 solution in DMSO dropwise over 25 min. The resulting mixture was heated to 80° C. for 45 min. After this time, the solid was collected while the suspension was still hot by vacuum filtration. The solid was rinsed with 1,4-dioxane (5 mL), methanol (2 mL), and acetonitrile (10 mL). The solid was heated in 0.5 N HCl (30 mL) to 80° C. and then the solid was collected while the suspension was still hot. The solid was rinsed with water and then dried in vacuo at 50° C. to afford F7 (151 mg, 48%) as a pale yellow solid: $^1$H NMR (500 MHz, DMSO-$d_6$) δ 12.92 (br s, 1H), 11.73 (s, 1H), 7.84-7.82 (m, 2H), 7.77-7.74 (m, 2H); ESI MS m/z 330 [M–H]$^-$.

Figure 17:
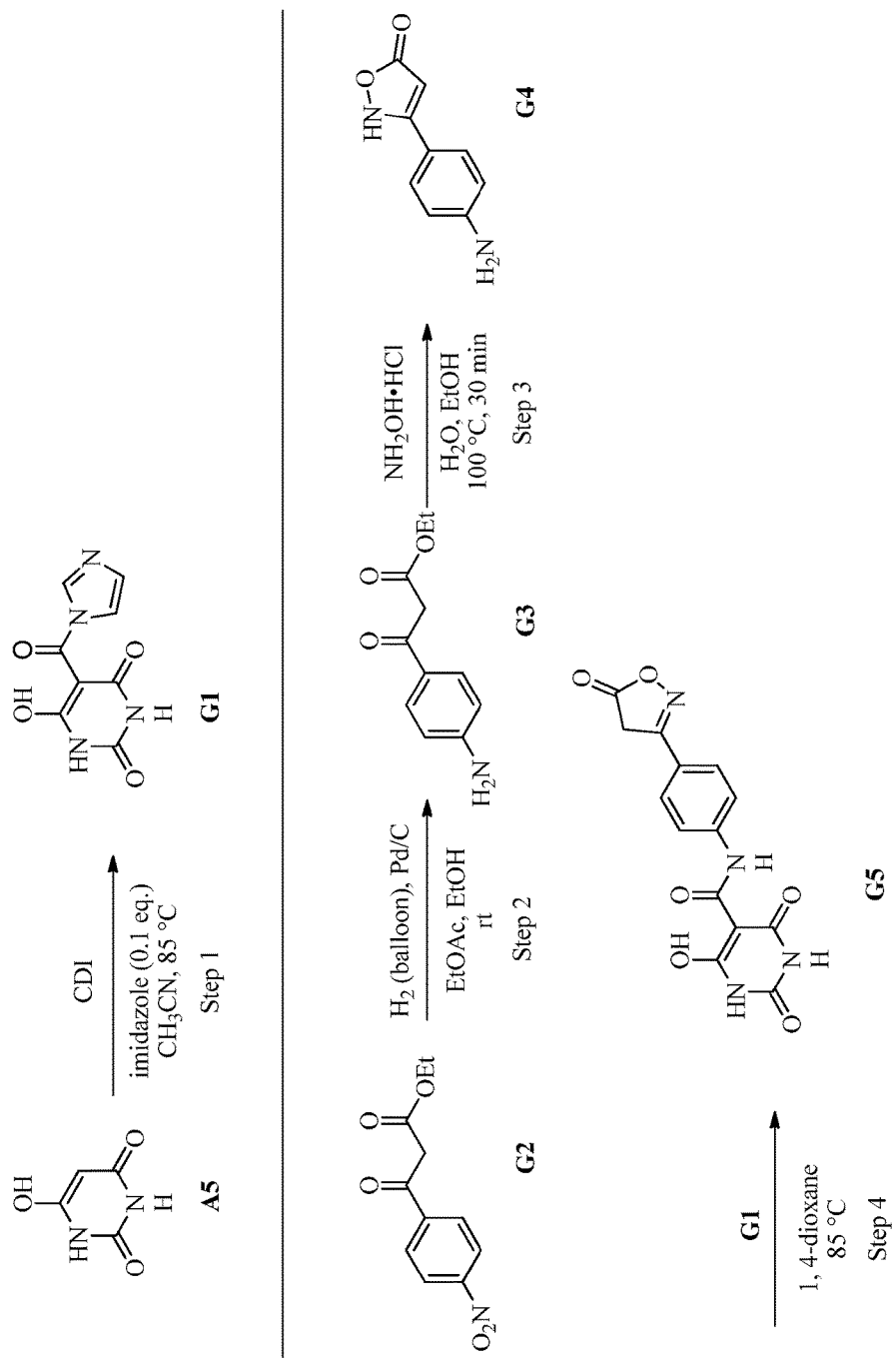
FIG. 17 illustrates an exemplary synthesis scheme for preparation of a compound having a structure represented by Formula (I$_h$).

Example 13: Preparation of 6-hydroxy-2,4-dioxo-N-(4-(5-oxo-4,5-dihydroisoxazol-3-yl)phenyl)-1,2,3,4-tetrahydropyrimidine-5-carboxamide (shown as G5 in FIG. 17, Formula Ih, with Reference to the Synthesis Scheme Illustrated in FIG. 17)

Step One.
6-Hydroxy-5-(1H-imidazole-1-carbonyl)pyrimidine-2,4(1H,3H)-dione (G1). A mixture of A5 (500 mg, 3.90 mmol), 1,1'-carbonyldiimidazole (633 mg, 3.90 mmol), and imidazole (25 mg, 0.39 mmol), in acetonitrile (10 mL) was heated in a sealed tube to 85° C. After 4 h the reaction mixture was cooled to ambient temperature. The precipitate was collected by vacuum filtration and rinsed with acetonitrile. The solid was dried in vacuo at to afford G1 (985 mg) as a yellow solid which was used without further purification. (Sample dissolved in methanol and LC-MS analysis shows a peak with ESI MS m/z 185 [M–H]$^-$ corresponding to methyl ester.)

Step Two.
Ethyl 3-(4-aminophenyl)-3-oxopropanoate (G3). A suspension of compound G2 (3.50 g, 14.8 mmol) and 10% palladium on carbon (50% wet, 350 mg) in ethyl acetate (80 mL) was stirred under 1 atmosphere of hydrogen at ambient temperature for 1.5 h. After this time, the reaction mixture was filtered through a short pad of diatomaceous earth and the filtrate was concentrated under reduced pressure. The material was purified by flash column chromatography on silica gel eluting with 5-50% ethyl acetate/hexanes to afford compound G3 (889 mg, 30%) as a white solid: $^1$H NMR (500 MHz, DMSO-$d_6$) δ 7.65-7.63 (m, 2H), 6.57-6.54 (m, 2H), 6.16 (s, 2H), 3.92 (s, 2H), 4.09 (q, J=7.0 Hz, 2H), 1.18-1.13 (m, 3H).

Step Three.
3-(4-Aminophenyl)isoxazol-5(2H)-one (G4). A mixture of G3 (1.30 g, 6.27 mmol) and hydroxylamine hydrochloride (1.30 g, 18.8 mmol) in water (7 mL) and ethanol (7 mL) was heated to 100° C. After 0.5 h, the reaction mixture was cooled in a ice/water bath. The resulting solid was collected by vacuum filtration to give G4 (254 mg, 23%) as a pale yellow solid: $^1$H NMR (500 MHz, DMSO-$d_6$, mixture of tautomers) δ 12.25 (br s, 0.5H), 7.38 (m, 2H), 6.62-6.59 (m, 2H), 5.85 (br s, 2H), 5.43 (s, 0.5H), 417 (s, 1H).

Step Four.
6-Hydroxy-2,4-dioxo-N-(4-(5-oxo-4,5-dihydroisoxazol-3-yl)phenyl)-1,2,3,4-tetrahydropyrimidine-5-carboxamide (G5, RLBN1044, Formula Ih). Combined G1 (425 mg, 1.91 mmol, purity ca 30%) and G4 (75 mg, 0.43 mmol) in 1,4-dioxane in a sealed tube. The yellow slurry was heated at 85° C. for 1 h and then cooled to ambient temperature. The solid was collected by vacuum filtration and rinsed with 1,4-dioxane. Next, the solid was triturated with 0.5 N HCl (20 mL) at 85° C. and the solid was collected while the slurry was still hot. The solid was rinsed with warm water and then dried in vacuo at 50° C. to afford G5 (33 mg, 23%) as a yellow solid: $^1$H NMR (500 MHz, DMSO-$d_6$, mixture of tautomers) δ 12.05 (br s, 1H), 11.70-11.35 (m, 1.6H), 7.78-7.69 (m, 4H), 5.72 (s, 0.55H), 4.31 (s, 0.85H); ESI MS m/z 329 [M–H]$^-$.

Figure 18:
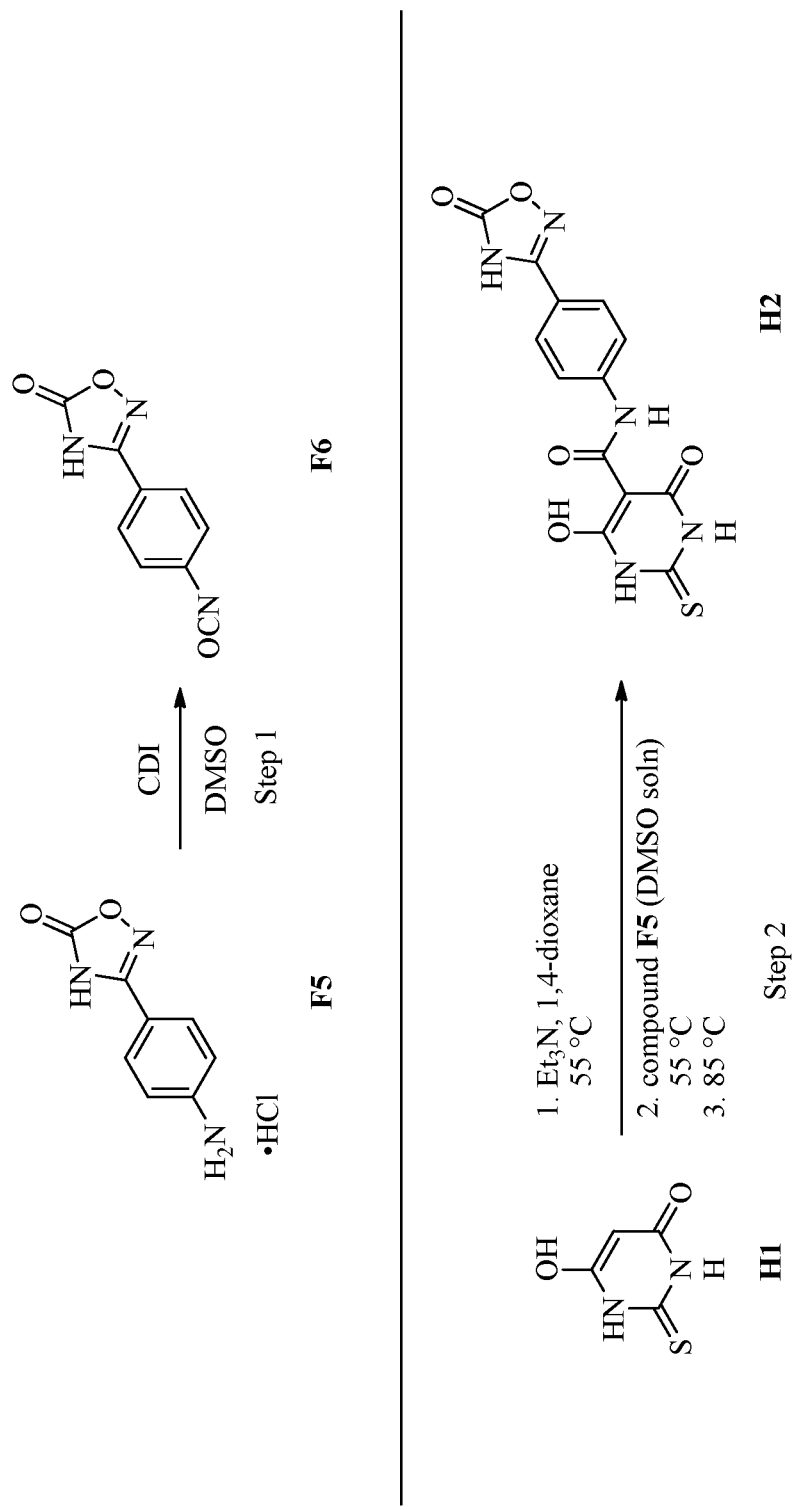
FIG. 18 illustrates an exemplary synthesis scheme for preparation of a compound having a structure represented by Formula (I$_g$).

Example 14: Preparation of 6-Hydroxy-4-oxo-N-(4-(5-oxo-4,5-dihydro-1,2,4-oxadiazol-3-yl)phenyl)-2-thioxo-1,2,3,4-tetrahydropyrimidine-5-carboxamide (shown as H2 in FIG. 18, Formula Ig, with Reference to the Synthesis Scheme Illustrated in FIG. 18)

Steps One and Two.
6-Hydroxy-4-oxo-N-(4-(5-oxo-4,5-dihydro-1,2,4-oxadiazol-3-yl)phenyl)-2-thioxo-1,2,3,4-tetrahydropyrimidine-5-carboxamide (H2, RLBN1045, Formula Ig). To a stirred solution of 1,1'-carbonyldiimidazole (298 mg, 1.84 mmol) and imidazole (9.0 mg, 0.13 mmol) in DMSO (1 mL), under a nitrogen atmosphere, was added compound F5 (280 mg, 1.31 mmol) in anhydrous DMSO (1 mL) dropwise over 15 min. The reaction mixture was then stirred at ambient temperature for 10 min to provide a solution of compound F6 in DMSO which was used directly in the subsequent step.

In a separate flask, to a suspension of 6-hydroxy-2-thioxo-2,3-dihydropyrimidin-4(1H)-one H1 (189 mg, 1.31 mmol) in anhydrous 1,4-dioxane (3 mL), at 55° C. and under a nitrogen atmosphere, was added triethylamine (0.18 mL, 1.3 mmol). After the addition was complete the mixture was stirred for 20 min. Then, to this mixture was added the compound F6 solution in DMSO dropwise over 25 min. Additional 1,4-dioxane (4 mL) was added and the resulting mixture was heated to 85° C. for 1.5 h. After this time, the solid was collected while the suspension was still hot by vacuum filtration. The solid was rinsed with 1,4-dioxane (5 mL), methanol (2 mL), and acetonitrile (10 mL). The solid was heated in 0.25 N HCl (15 mL) to 80° C. and then the solid was collected while the suspension was still hot. The solid was rinsed with water (10 mL) and then dried in vacuo at 50° C. to afford H2 (113 mg, 25%) as an off-white solid: $^1$H NMR (500 MHz, DMSO-$d_6$) δ 12.92 (br s, 1H), 11.64 (s, 1H), 7.84-7.82 (m, 2H), 7.79-7.76 (m, 2H); ESI MS m/z 346 [M–H]$^-$.

Figure 19:
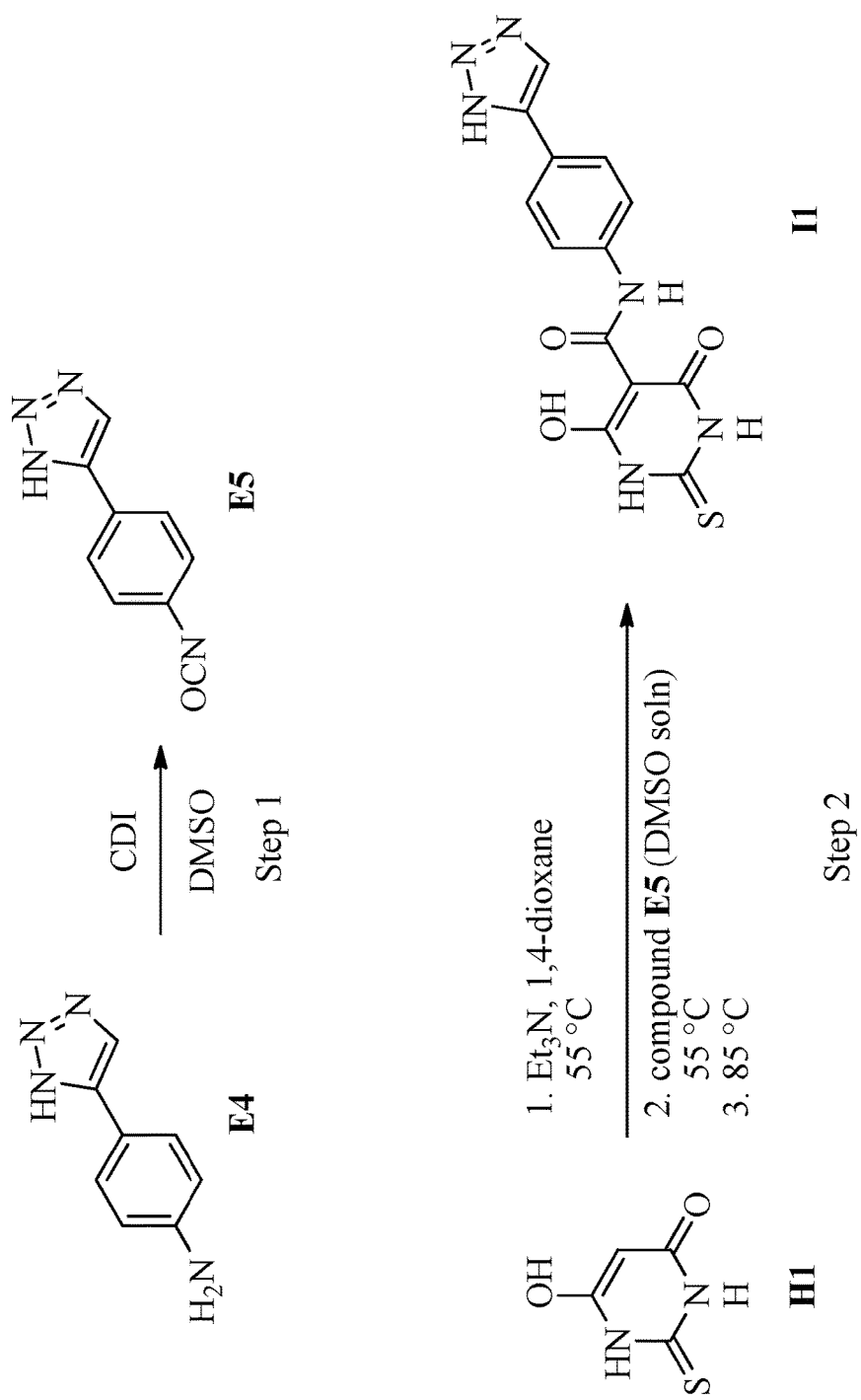
FIG. 19 illustrates an exemplary synthesis scheme for preparation of a compound having a structure represented by Formula (II$_f$).

Example 15: Preparation of N-(4-(1H-1,2,3-triazol-5-yl)phenyl)-6-hydroxy-4-oxo-2-thioxo-1,2,3,4-tetrahydropyrimidine-5-carboxamide (shown as I1 in FIG. 19, Formula Iff, with Reference to the Synthesis Scheme Illustrated in FIG. 19)

Steps One and Two.
N-(4-(1H-1,2,3-triazol-5-yl)phenyl)-6-hydroxy-4-oxo-2-thioxo-1,2,3,4-tetrahydropyrimidine-5-carboxamide (I1, RLBN1046, Formula IIf). To a stirred solution of 1,1'-carbonyldiimidazole (191 mg, 1.18 mmol) and imidazole (6.0 mg, 0.084 mmol) in DMSO (1 mL), under a nitrogen atmosphere, was added compound E4 (135 mg, 0.842 mmol) in anhydrous DMSO (1 mL) dropwise over 10 min. The reaction mixture was then stirred at ambient temperature for 10 min to provide a solution of compound E5 in DMSO which was used directly in the subsequent step.

In a separate flask, to a suspension of 6-hydroxy-2-thioxo-2,3-dihydropyrimidin-4(1H)-one H1 (121 mg, 0.839 mmol) in anhydrous 1,4-dioxane (3 mL), at 55° C. and under a nitrogen atmosphere, was added triethylamine (0.12 mL, 0.84 mmol). After the addition was complete the mixture was stirred for 20 min. Then, to this mixture was added the compound E5 solution in DMSO dropwise over 20 min. The resulting mixture was heated to 80° C. for 0.5 h. After this time, the reaction mixture was cooled to ambient temperature and concentrated under reduced pressure to remove the 1,4-dioxane. The resulting solution was added dropwise to rapidly stirring 0.5 N HCl (80 mL) The solid was then stirred in water (2 mL) and 1 N HCl (0.25 mL) at 50° C. for 0.5 h. The solid was collected, rinsed with water (20 mL) and acetonitrile (20 mL). The solid was triturated in 0.25 N HCl at 85° C. and the solid was collected while the suspension was still hot by vacuum filtration. The solid was rinsed with water and then dried in vacuo at 50° C. to afford I1 (44 mg, 30%) as an off-white solid: $^1$H NMR (500 MHz, TFA-d) δ 8.84 (s, 1H), 8.14-8.01 (m, 4H); ESI MS m/z 329 [M−H]$^-$.

Example 16: Bioactivity Assays

The biological activities of compounds having structures represented by Formula (I), Formula (II), and Formula (III) were evaluated in two assays: xanthine oxidase activity and URAT1 activity.

Xanthine oxidase inhibition was determined using a standard fluorescence-based assay for xanthine oxidase activity (McHale A, Grimes H, Coughlan M P: Int J Biochem. 10:317-9, 1979) with minor variations. The procedure was internally standardized using allopurinol and DPI as controls for all experiments after determination of their optimal inhibitory concentrations. Experiments on test compounds were performed in triplicate in multi-well plates using 10 concentrations of each compound that ranged over a 3-fold dilution.

URAT1 (SLC22A12) activity was evaluated in a cellular uptake assay using a 96-well plate with stably transfected URAT-1/CHO cells. $^3$H-orotate was used as the test transport agent, which was measured in a liquid scintillation counter, using benzbromarone as a positive control, and DMSO and non-transfected CHO cells as negative controls (Solvo Biotechnology, Boston, Mass.). Generally determined over 7 concentrations (range, 0.01 to 150 µM), a semi-log plot (percent relative transport of oratate vs. time) was generated to determine the concentration at which 50% inhibition was observed (i.e., the IC50).

The results of these assays are shown in the following Table:

| Compound | URAT1 IC50 (µM) | Xanthine Oxidase IC50 (µM) |
|---|---|---|
| Formula (I$_a$) | ND | ≥300 |
| Formula (I$_b$) | ND | 87 |
| Formula (I$_c$) | ND | 201 |
| Formula (I$_d$) | 7.26 | 3.66 |
| Formula (II$_a$) | 9.54 | 0.68 |
| Formula (II$_b$) | 147 | 0.39 |
| Formula (II$_c$) | ND | 20.68 |
| Formula (III$_a$) | 1.34 | 8.93 |
| Formula (II$_f$) | 11.1 | 0.06 |
|  |  | 0.09 |
| Formula (II$_e$) | 0.69 | 1.24 |
|  |  | 1.14 |
| Formula (I$_g$) | >150 | 3.29 |
|  |  | 8.01 |
| Formula (I$_f$) | 7.6 | 4.81 |
|  |  | 7.74 |
| Allopurinol | >300$^\dagger$ | 2.0 to 5.0 |
| Lesinurad | 18.61* | >300$^\dagger$ |
|  | 52.5 ± 5.9$^{\dagger*}$ |  |

$^\dagger$Presentation estimate; Proc. EULAR Abstract #THU0357, 2008
*URAT1 assay as described herein With the exception of Formula (I$_d$), the Formula (I) compounds were relatively weak inhibitors of XO and thus were not tested against URAT1, since such compounds could not be considered highly potent bifunctional inhibitors. However, Formula (I$_d$) proved to be a highly potent bifunctional compound, inhibiting both URAT1 and XO with an IC50 of less than 10 µM. In contrast, most of the Formula II and Formula III compounds (except Formula (II$_c$)) were shown to be potent bifunctional inhibitors of both XO and URAT1.

The Formula (I$_g$) and Formula (I$_f$) compounds differ in structure, respectively, only by the sulfur and oxygen moieties at C2. The Formula (I$_g$) compound is a poor URAT1 inhibitor and an acceptable XO inhibitor, but the Formula (I$_f$) compound is active against both targets. This suggests that, like membrane, the sulfur-containing compound may be metabolized to a bifunctional oxygen-containing compound.

The Formula (II$_f$) and Formula (II$_e$) compounds (C2 sulfur and oxygen, respectively) were particularly potent, with nanomolar inhibition of both XO and URAT1. These compounds are 2 to 30 times more potent than lesinurad against URAT1, and 3 to 50 times more potent than allopurinol. The XO inhibition of the Formula (II$_f$) compound is comparable to febuxostat, and the URAT1 inhibition is comparable to benzbromarone.

While most Formula II and III compounds were potent as defined herein, the relative variability of inhibition for each enzyme was different. Such variability allows the intelligent selection of a pharmaceutically acceptable product that exhibits greater or lesser inhibition of one or the other enzyme target. For example, greater inhibition of XO might be deemed preferable for a patient whose primary metabolic defect was over-production of uric acid. Conversely, greater inhibition of URAT1 might be deemed preferable for a patient whose primary metabolic defect was under-excretion of uric acid. However, it should be noted that almost all patients with hyperuricemia will benefit from reduction in serum uric acid, and bifunctional compounds can be expected to exert a beneficial effect in such patients. The practitioner, guided by the present disclosure, will be able to select particular compounds as appropriate for a specific use based on the level of skill in the art.

By way of comparison, allopurinol has an IC50 for XO ranging from about 2.0 to about 5.0 µM and an IC50 for URAT1 of >300 µM. Lesinurad has an IC50 for XO of >300 µM and an IC50 for URAT1 ranging from 18 to 53 µM. Thus, neither of these compounds is considered bifunctional, since both are selective inhibitors of only one enzyme that affects either production or excretion of uric acid. In contrast, the compounds of the invention are not only bifunctional, but several of the compounds are substantially more potent inhibitors of both XO and URAT1.

While in many clinical situations it is desirable to treat hyperuricemia with a drug that is highly potent against both XO and URAT1, it is also contemplated that selection of a particular compound of the invention for treatment of hyperuricemia may be based on the phenotype of the hyperuricemic patient being treated (i.e., the relative contributions of over-production of uric acid and under-excretion of uric acid to the patient's specific disease). Where over-production of uric acid predominates, use of compounds according to the invention that are substantially more potent against XO than URAT1 may be appropriate (e.g., Formula (II$_a$)). Where under-excretion of uric acid predominates, use of compounds according to the invention that are substantially more potent against URAT1 than XO may be appropriate (e.g., Formula (III$_a$). Although the genetics of these two pathways are not completely understood, chemical testing to determine the extent to which each contributes to the hyperuricemia of a particular patient has been published, and is expected to be useful to determine the patient's disease phenotype for selection of an appropriate drug.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A compound selected from the group consisting of
a) compounds having a structure represented by Formula (I):

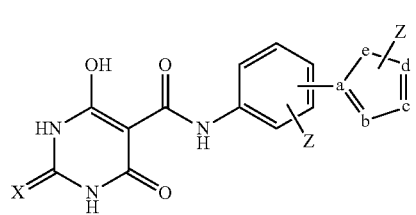

Formula (I)

wherein

X is O or S;

W is present or absent, and if present is one or more hydroxyl moieties, $R^1OH$, or at least one hydroxyl moiety and $R^1OH$; and Z is present or absent, and if present is $SO_2N(R^2)_2$, $-R_1CO_2H$,

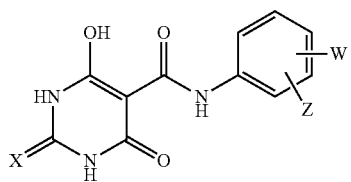

$-NR^2SO_2R^3$, $-NR^2SO_2N(R^2)_2$, or $-NR^2C(O)N(R^2)_2$;

wherein $R^1$ is alkyl;

wherein each $R^2$ is independently H, alkyl or aryl, each optionally substituted with one or more halogen atoms or $OR^2$;

wherein each $R^3$ is independently alkyl or aryl, each optionally substituted with one or more halogen atoms or $OR^2$; and wherein each $X^a$ is independently selected from either O or S, provided that at least one of W and Z is present, and if W is present and Z is absent, W is not 4'-hydroxy;

b) compounds having a structure represented by Formula (II):

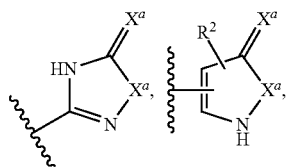

Formula (II)

wherein

X is O or S; and each Z is independently present or absent and, if present, is independently selected from one or more halogen atoms, $-CN$, $-CF_3$, $-OR^2$, $-C(O)R^2$, $SR^2$, $-S(O)_fR^3$ where f is 1 or 2, $-N(R^2)_2$, $-NO_2$, $-CO_2R^2$, $-OCO_2R^3$, $OC(O)R^2$, $-CON(R^2)_2$, $-NR^2C(O)R^2$, $-SO_2(NR^2)_2$, $-NR^2SO_2R^3$, $-NR^2SO_2N(R^2)_2$, $-NR^2C(O)N(R^2)_2$, alkyl, aryl, alkenyl and alkynyl;

wherein each $R^2$ is independently H, alkyl or aryl;

wherein each $R^3$ is independently alkyl or aryl, optionally substituted with one or more halogen atoms or $OR^2$; and wherein a, b, c, d, and e are each independently carbon or nitrogen, with the proviso that at least one of a, b, c, d and e is nitrogen and Z is not connected directly to a nitrogen, except that Z may optionally be connected to a nitrogen at a, b, c, d, or e by replacement of the hydrogen of an NH group when Z is $-C(O)R^2$, $-S(O)_fR^3$, $-CO_2R^3$, $-CON(R^2)_2$, $-SO_2N(R^2)_2$, alkyl, aryl, alkenyl or alkynyl;

c) compounds having a structure represented by Formula (III):

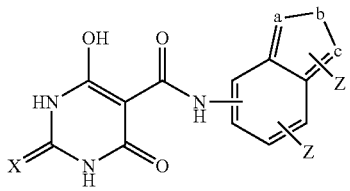

Formula (III)

wherein

X is O or S; and each Z is independently present or absent and, if present, is independently selected from one or more halogen atoms, $-CN$, $-CF_3$, $-OR^2$, $-C(O)R^2$, $SR^2$, $-S(O)_fR^3$ where f is 1 or 2, $-N(R^2)_2$, $-NO_2$, $-CO_2R^2$, $-OCO_2R^3$, $OC(O)R^2$, $-CON(R^2)_2$, $-NR^2C(O)R^2$, $-SO_2(NR^2)_2$, $-NR^2SO_2R^3$, $-NR^2SO_2N(R^2)_2$, $-NR^2C(O)N(R^2)_2$, alkyl, aryl, alkenyl and alkynyl;

wherein each $R^2$ is independently H, alkyl or aryl;

wherein each $R^3$ is independently alkyl or aryl, optionally substituted with one or more halogen atoms or $OR^2$; and wherein a, b, and c, are each independently carbon or nitrogen, with the proviso that at least one of a, b, and c is nitrogen and Z is not connected directly to a nitrogen, except that Z may optionally be connected to a nitrogen at a, b, or c by replacement of the hydrogen of an NH group when Z is —C(O)R², —S(O)ⱼR³, —CO₂R², —CON(R²)₂, —SO₂N(R²)₂, alkyl, aryl, alkenyl or alkynyl; and d) tautomers of any of the foregoing compounds.

2. The compound according to claim 1 having a structure represented by Formula (II), wherein X is O or S; both Z are absent; c and d are N; e is NH; and, a and b are C; or a tautomer thereof.

3. The compound according to claim 1, which is selected from the group consisting of compounds having a structure represented by:

Formula (Iₐ)
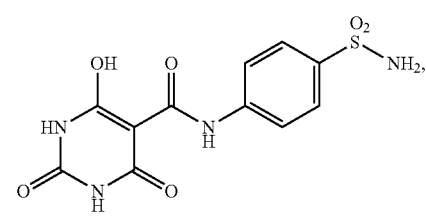

Formula (I_b)
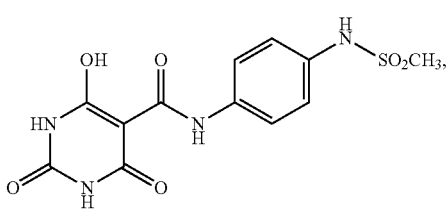

Formula (I_c)
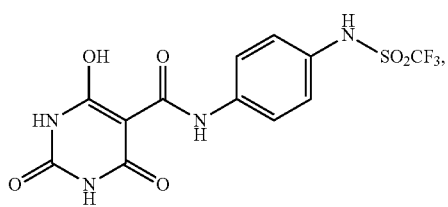

Formula (I_d)
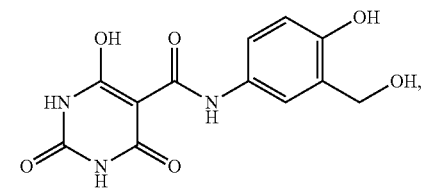

Formula (I_e)
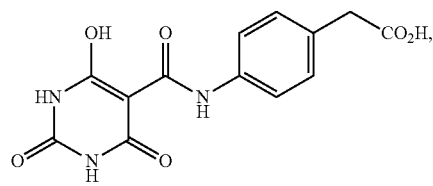

Formula (I_f)
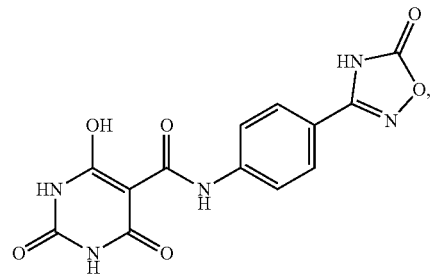

Formula (I_g)
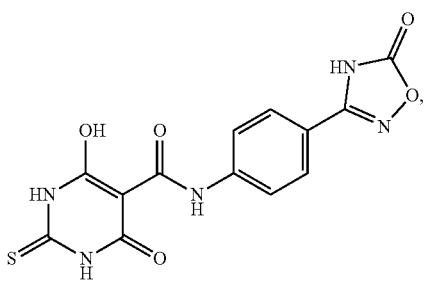

Formula (I_h)
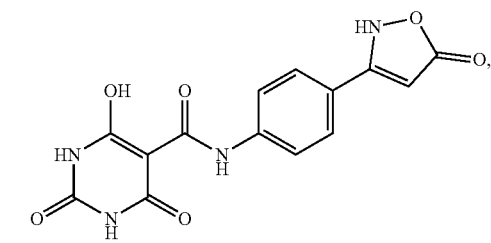

Formula (IIₐ)
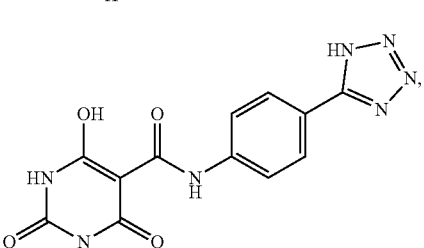

Formula (II_b)
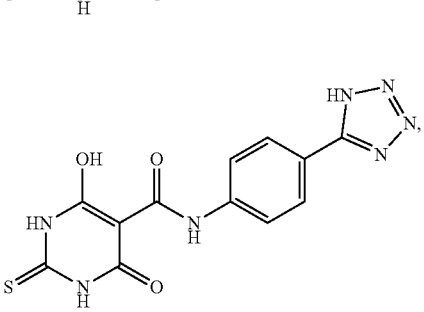

Formula (II_c)
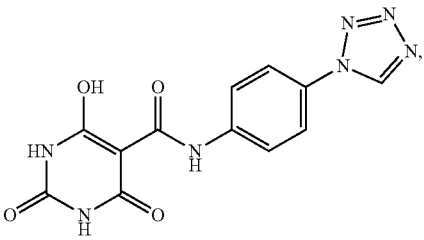

Formula (II_d)
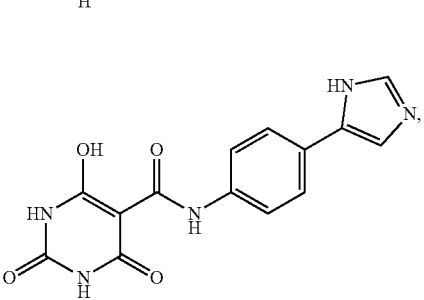

-continued

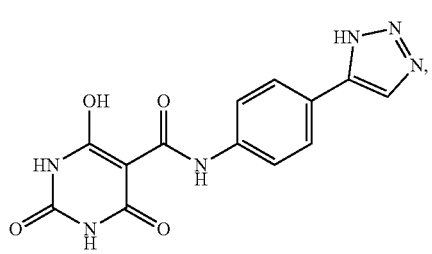
Formula (II$_e$)

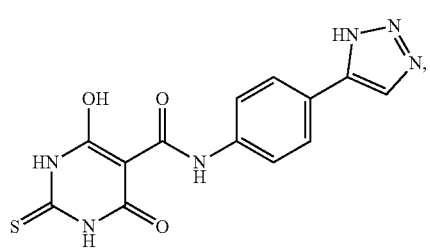
Formula (II$_f$)

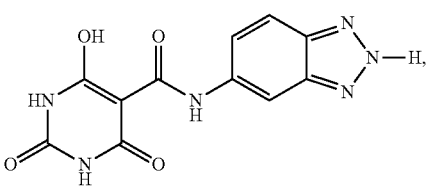
Formula (III$_a$)

and
tautomers thereof.

4. The compound according to claim 3 having the structure represented by:

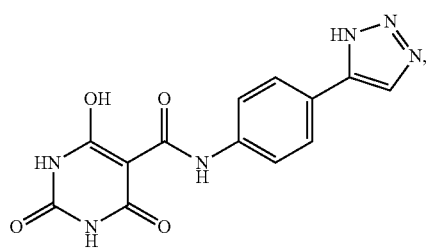
Formula (II$_e$)

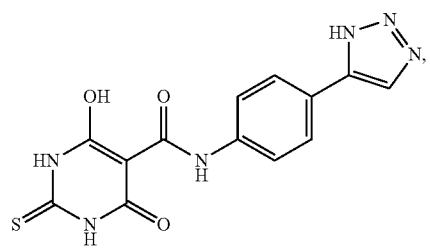
Formula (II$_f$)

a tautomer of Formula (II$_e$) or a tautomer of Formula (II$_f$).

5. A pharmaceutical composition comprising a compound according to claim 1; a tautomer thereof, or a combination thereof, and a pharmaceutically acceptable carrier.

6. The pharmaceutical composition according to claim 5 which is formulated for controlled or extended release of the compound or combination thereof.

7. The pharmaceutical composition according to claim 5, which comprises a compound having a structure represented by:

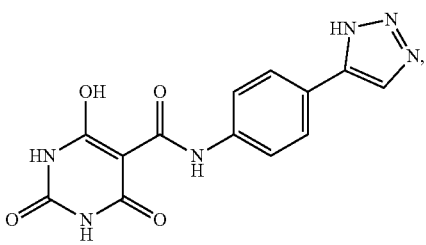
Formula (II$_e$)

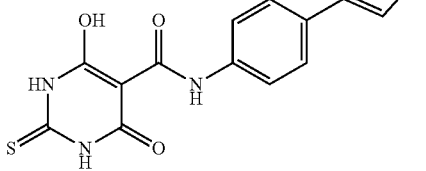
Formula (II$_f$)

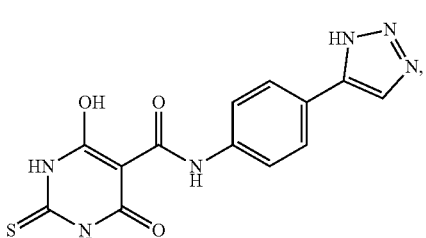

a tautomer of Formula (II$_e$), a tautomer of Formula (II$_f$), or a combination thereof.

8. The pharmaceutical composition according to claim 5, wherein the pharmaceutically acceptable carrier is selected from the group consisting of water or saline, a solvent, a dispersing agent, a coating, a surfactant, a preservative, an emulsion, an alcohol, a polyol, and an isotonic agent.

9. A method for reducing uric acid levels in blood or serum of a subject comprising administering to a subject in need thereof a compound according to claim 1; a tautomer thereof; or a combination thereof, in an amount effective to reduce blood or serum uric acid levels.

10. The method according to claim 9, wherein administering the compound treats a disorder of uric acid metabolism caused by, or associated with, hyperuricemia.

11. The method of claim 10 wherein the disorder of uric acid metabolism is selected from the group consisting of gout, hyperuricemia, tumor lysis syndrome, kidney disease, arthritis, kidney stones, kidney failure, urolithiasis, plumbism, hyperparathyroidism, psoriasis, inborn genetic errors of metabolism, sarcoidosis or cardiovascular disease.

12. The method according to claim 11, wherein the disorder of uric acid metabolism is gout.

13. The method according to claim 9, wherein a daily dose of about 20 to about 1,500 mg/m$^2$/day is administered.

14. The method according to claim 13, wherein a daily dose of about 20 to about 150 mg/m$^2$/day is administered.

15. The method according to claim 9, wherein the compound or combination thereof is administered by injection, infusion, or oral administration.

16. The method according to claim 15, wherein the compound or combination thereof is administered by intravenous infusion or bolus injection.

17. The method according to claim 9, which comprises administration of a compound having a structure represented by:

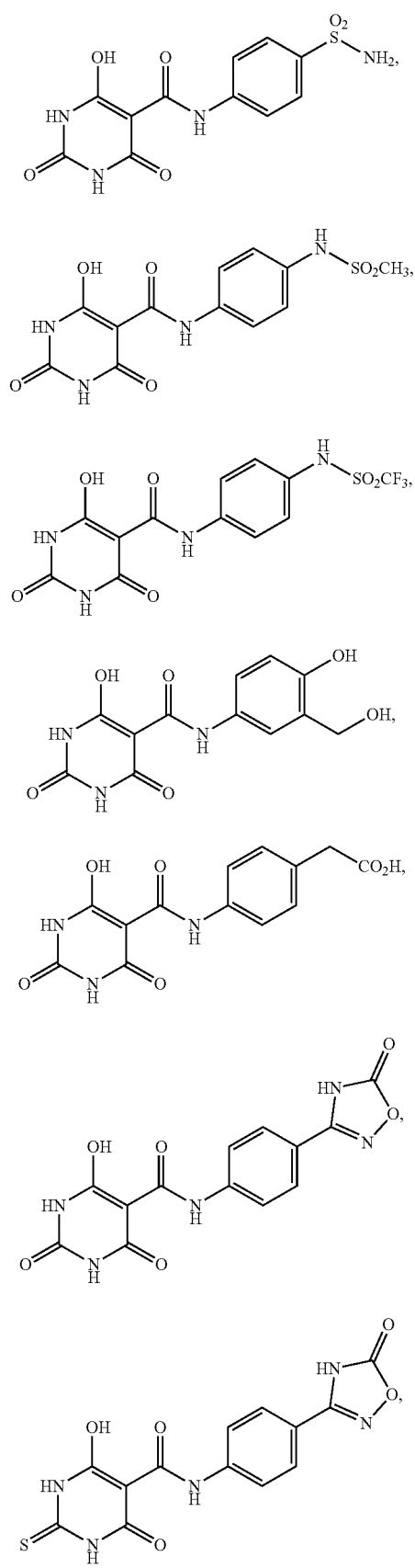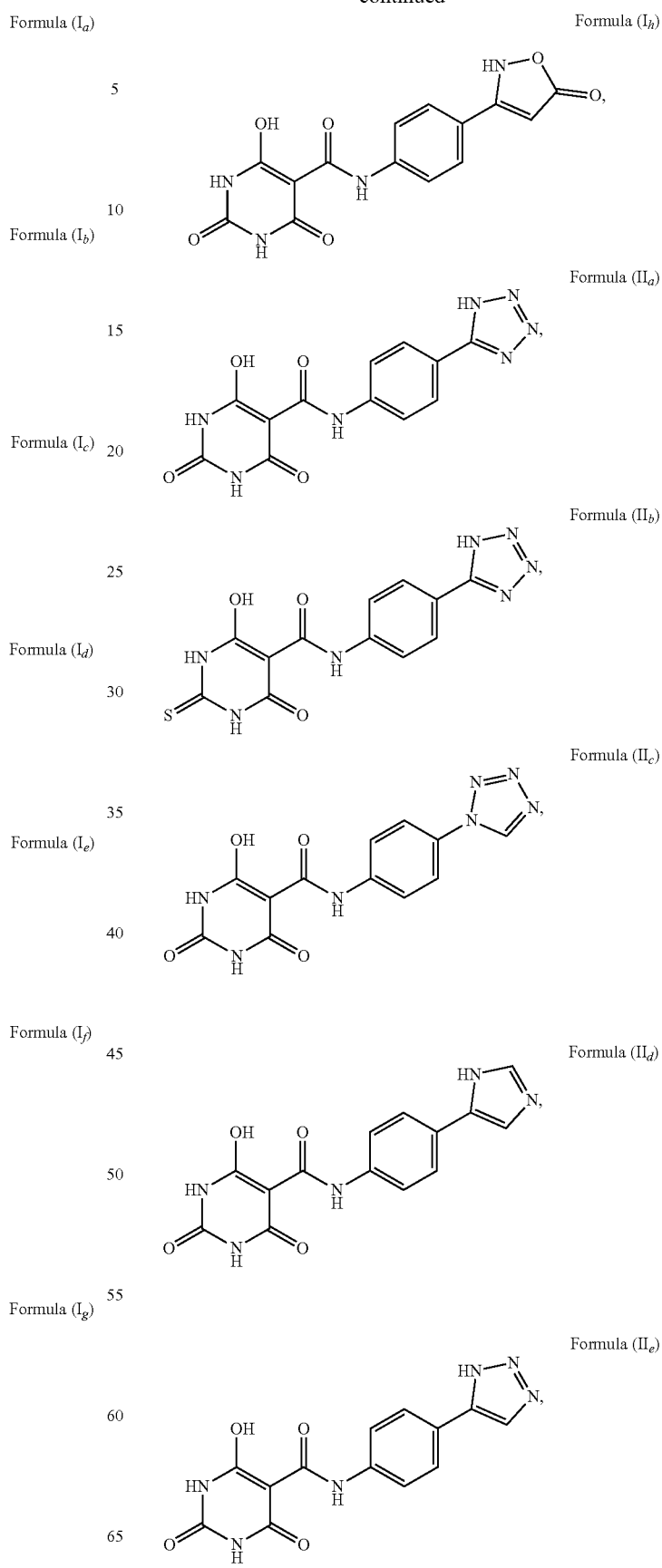

-continued
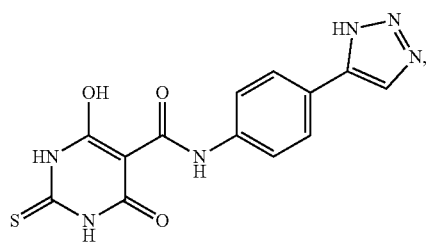
Formula (II_f)
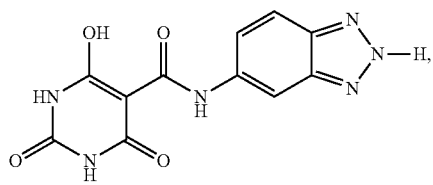
Formula (III_a)
a tautomer of any of the foregoing, or a combination thereof.
* * * * *